(12) United States Patent
Biro et al.

(10) Patent No.: US 11,369,965 B2
(45) Date of Patent: Jun. 28, 2022

(54) LIGHT-MEDIATED POLYMERASE CHAIN REACTION AMPLIFICATION AND PRODUCT DETECTION SYSTEM AND METHODS OF USE

(71) Applicant: PIONEER HI-BRED INTERNATIONAL, INC., Johnston, IA (US)

(72) Inventors: Ronald L. Biro, Clive, IA (US); Beau Hunt, Ankeny, IA (US)

(73) Assignee: PIONEER HI-BRED INTERNATIONAL, INC.

( * ) Notice: Subject to any disclaimer, the term of this patent is extended or adjusted under 35 U.S.C. 154(b) by 0 days.

(21) Appl. No.: 16/061,590

(22) PCT Filed: Mar. 8, 2017

(86) PCT No.: PCT/US2017/021359
§ 371 (c)(1),
(2) Date: Jun. 12, 2018

(87) PCT Pub. No.: WO2017/156126
PCT Pub. Date: Sep. 14, 2017

(65) Prior Publication Data
US 2018/0361379 A1   Dec. 20, 2018

Related U.S. Application Data

(60) Provisional application No. 62/306,432, filed on Mar. 10, 2016.

(51) Int. Cl.
*C12Q 1/686* (2018.01)
*B01L 3/00* (2006.01)
(Continued)

(52) U.S. Cl.
CPC .......... *B01L 3/50851* (2013.01); *B01L 7/52* (2013.01); *C12Q 1/686* (2013.01);
(Continued)

(58) Field of Classification Search
CPC .......... B01L 2200/142; B01L 3/50851; B01L 2300/1872; B01L 7/52; B01L 2300/0819;
(Continued)

(56) References Cited

U.S. PATENT DOCUMENTS 5,972,667 A * 10/1999 Conia .................. C12N 13/00
                                                    435/173.1
6,783,993 B1 * 8/2004 Malmquist .......... B01F 9/0003
                                                    422/401
(Continued)

FOREIGN PATENT DOCUMENTS

EP         1 541 237 A2     6/2005
EP         1 964 610 A2     9/2008
WO         1996/041864 A1  12/1996

OTHER PUBLICATIONS

Son et al "Ultrafast photonic PCR", Light: Science & Applications, 2015, 4, e280, pp. 1-7 (Year: 2015).*
(Continued)

*Primary Examiner* — Young J Kim

(57) ABSTRACT

A PCR amplification and product detection system is disclosed. The system utilizes a uniform and direct photonic heating subsystem to mediate reaction-by-reaction, high-throughput PCR amplification detectable by a fluorescence detection subsystem. Reaction-by-reaction temperature monitoring for dynamic feedback heat regulation is also disclosed. Also disclosed are methods for using the same.

21 Claims, 19 Drawing Sheets

(51) Int. Cl.
  *B01L 7/00* (2006.01)
  *G01N 21/64* (2006.01)
  *G01N 35/02* (2006.01)

(52) U.S. Cl.
  CPC ..... *G01N 21/6428* (2013.01); *G01N 21/6452* (2013.01); *B01L 2200/0673* (2013.01); *B01L 2200/142* (2013.01); *B01L 2300/0812* (2013.01); *B01L 2300/1822* (2013.01); *B01L 2300/1844* (2013.01); *B01L 2300/1872* (2013.01); *G01N 35/021* (2013.01); *G01N 2021/6484* (2013.01); *G01N 2201/0826* (2013.01); *G01N 2201/0833* (2013.01)

(58) Field of Classification Search
  CPC ....... B01L 2300/0829; B01L 2300/087; B01L 2200/0605; B01L 7/5255; B01L 2200/0673; B01L 2300/0812; B01L 2300/1822; B01L 2300/1844; G01N 2021/6484; G01N 21/6428; G01N 21/6452; G01N 35/021; G01N 21/0332; G01N 21/253; G01N 35/04; C12Q 1/686; C12Q 2563/107; C12Q 2563/159; C12Q 1/6825; C12Q 2565/629
  See application file for complete search history.

(56) References Cited

U.S. PATENT DOCUMENTS

| | | | |
|---|---|---|---|
| 7,081,226 | B1 | 7/2006 | Wittwer et al. |
| 2002/0001848 | A1* | 1/2002 | Bedingham .......... B01L 3/5025 436/45 |
| 2003/0231878 | A1* | 12/2003 | Shigeura .................. B01L 7/52 392/407 |
| 2004/0071599 | A1* | 4/2004 | Rusch .................. B01L 3/5085 422/552 |
| 2004/0208792 | A1* | 10/2004 | Linton .................... B01L 3/508 422/552 |
| 2005/0133724 | A1 | 6/2005 | Hsieh et al. |
| 2008/0176290 | A1* | 7/2008 | Joseph .................. C12Q 1/686 435/91.2 |
| 2009/0325164 | A1* | 12/2009 | Vossenaar .......... B01L 3/50851 435/6.11 |
| 2011/0256532 | A1* | 10/2011 | Sano .................... G01N 35/025 435/6.1 |
| 2012/0045765 | A1 | 2/2012 | Curran et al. |

OTHER PUBLICATIONS

International Search Report and Written Opinion, International Application No. PCT/US2017/021359 dated Aug. 14, 2017.

* cited by examiner

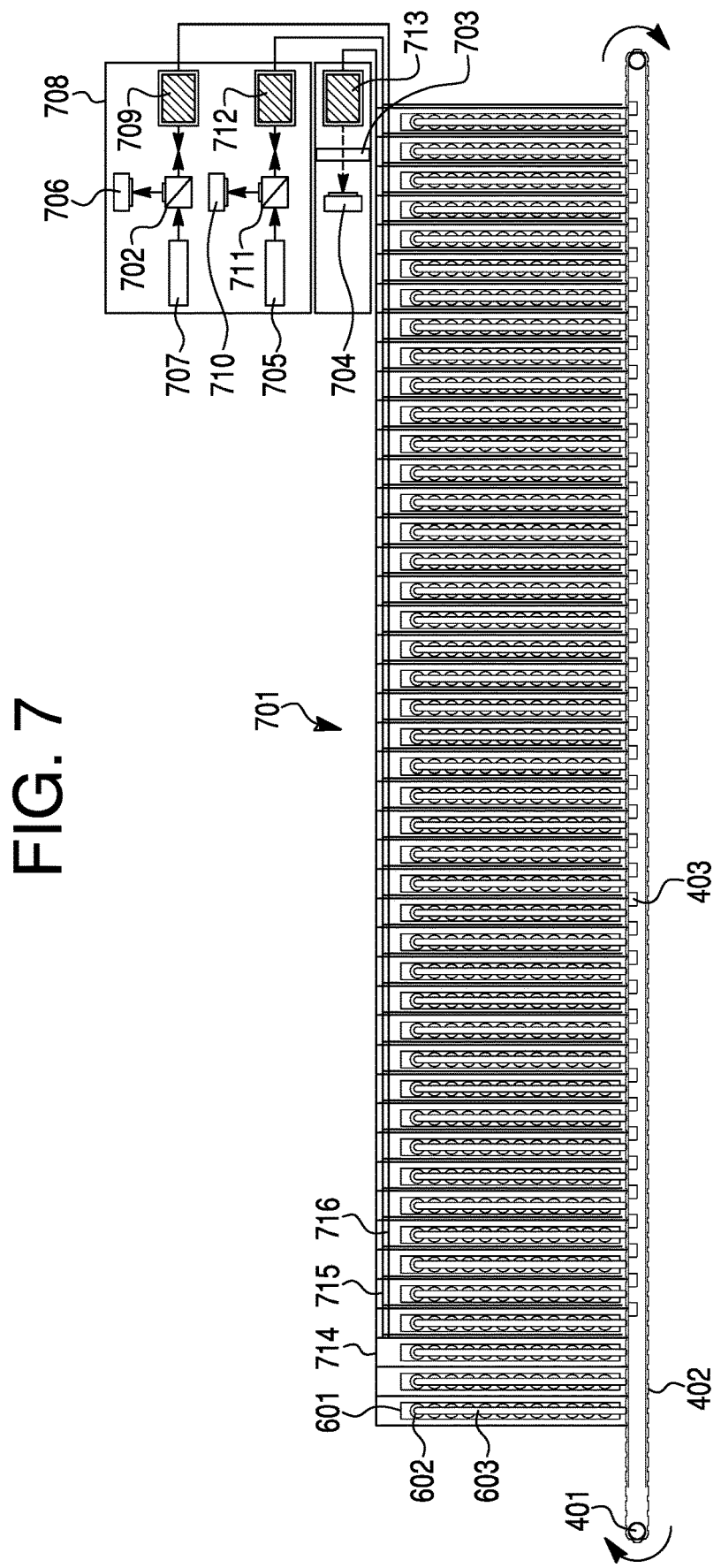

Electronics And Software Control Sub-Systems Functional Block Diagram For Complete Beginning-To-End Integrated System Embodiment

LIGHT-MEDIATED POLYMERASE CHAIN REACTION AMPLIFICATION AND PRODUCT DETECTION SYSTEM AND METHODS OF USE

FIELD

This disclosure relates to a high-throughput, light-mediated polymerase chain reaction (PCR) amplification and product detection system and methods of using the same. The system allows for reaction-by-reaction, rapid and uniform photonic heating of an aqueous oil matrix and combines temperature monitoring and PCR product detection in an integrated high-throughput system.

BACKGROUND

Amplification of DNA by polymerase chain reaction (PCR) is a technique fundamental to molecular biology. Nucleic acid analysis by PCR requires sample preparation, amplification, and product analysis. Although these steps are usually performed sequentially, amplification and analysis can occur simultaneously. DNA dyes or fluorescent probes can be added to the PCR mixture before amplification and used to analyze PCR products during amplification. Sample analysis occurs concurrently with amplification in the same tube within the same instrument. This combined approach decreases sample handling, saves time, and greatly reduces the risk of product contamination for subsequent reactions, as there is no need to remove the samples from their closed containers for further analysis. The concept of combining amplification with product analysis has become known as "real time" PCR. See, e.g., U.S. Pat. No. 6,174,670.

Currently, the processing of polynucleotide samples in high-throughput PCR assays has a number of key drawbacks. These include the volume size resulting in high reagent costs, high consumable costs, and labor-intensive protocols and processes which are highly susceptible to contamination. Some of these issues can be resolved by encapsulating an aqueous droplet, which contains the PCR reaction reagents, polynucleotide sample, primers and probes, in one or more non-miscible oils. The generation of these aqueous oil matrices decreases volume size and risk of contamination. The formation of aqueous oil matrices has been described in the patent literature, for example, in U.S. Pat. No. 8,465,707.

Available systems employing constant temperature zones for subjecting aqueous oil matrices to PCR thermocycling have shown significant problems in providing uniform heating temperatures and may suffer from slow heat transfer from a relatively remote heating source to the samples. Other systems using flowing rivers of carrier oil to transport the aqueous oil matrices through the system show significant problems with the control of the flow rate and depth of the carrier oil. Other methods use miniaturized high-throughput-based PCR chips that incorporate a heater and/or temperature sensor inside the substrate. However, this technique requires complex design and fabrication of the chips.

Thus, there remains a need for systems and methods for PCR amplifying samples that are high-throughput, reduces cost, provides greater analysis flexibility, reduces turnaround time, and improves data quality.

BRIEF SUMMARY

One aspect of the disclosure features a polymerase chain reaction (PCR) amplification and product detection system, comprising an assembly subsystem that includes a plurality of vessels and one or more liquid dispensing members configured to assemble a collection of aqueous oil matrices, each aqueous oil matrix comprising: 1) an aqueous reaction mix comprising a volume of polynucleotide sample and reagents; and 2) one or two non-miscible oils selected from the group consisting of an encapsulation oil, a carrier oil, and both an encapsulation oil and a carrier oil. As such, components of the aqueous reaction mix do not mix with the one or two non-miscible oils. In this embodiment, each aqueous oil matrix is dispensed by the one or more liquid dispensing members into a vessel for PCR amplification and product detection.

The system also comprises a plurality of heating positions, temperature monitoring positions, and PCR product detection positions. In addition, the system includes a reaction-by-reaction, light-driven photonic heating subsystem comprising a plurality of electromagnetic radiation sources, wherein each vessel is in optical communication with an electromagnetic radiation source when that vessel is in a heating position, and the electromagnetic radiation source emits electromagnetic radiation to that vessel; a reaction-by-reaction temperature monitoring subsystem comprising a plurality of thermal detection devices, wherein each vessel corresponds to a thermal detection device when that vessel is in a temperature monitoring position, and wherein detection device is configured to provide a measuring signal dependent on the temperature of the aqueous oil matrix when the vessel is in the temperature monitoring position; a microcontroller temperature feedback and light source control subsystem communicatively connected to both the photonic heating subsystem and the temperature monitoring subsystem, wherein the microcontroller temperature feedback and light source control subsystem is configured to regulate energy input required for output control and duration of the electromagnetic energy emitted by the electromagnetic radiation source through a cycle of reaction temperatures; and a fluorescence detection subsystem. Further, the fluorescence detection subsystem comprises: i) one or more fluorescence excitation light sources; ii) one or more fluorescence emission light sensing devices; iii) a plurality of first optical members in optical communication with the one or more fluorescence excitation light sources, wherein each first optical member is configured to provide an optical path for fluorescence excitation light having a first spectral wavelength from the one or more fluorescence excitation light sources to one of said vessels containing the aqueous oil matrix when the vessel is in a PCR product detection position, wherein the volume of the aqueous reaction mix comprises a first reagent capable of excitation by the fluorescence excitation light having the first spectral wavelength when the first reagent hybridizes to the polynucleotide sample, and wherein each first optical member is further configured to provide an optical path for fluorescence emission light from the aqueous reaction mix to the one or more fluorescence emission light sensing devices; and iv) an active or passive cooling mechanism at the PCR product detection position whereby each of the vessels in the PCR product detection position are cooled.

Also provided is a mechanical and electronic control system communicatively connected to a positioning device and to the assembly subsystem, wherein mechanical and electronic control system causes the assembly subsystem to assemble the aqueous oil matrices in the plurality of vessels, and wherein the mechanical and electronic control system causes the positioning device to move the plurality of vessels from the assembly subsystem to each of the heating positions, temperature monitoring positions, and PCR product detection positions.

In another aspect, provided herein is a method for light-mediated PCR amplification and product detection utilizing the PCR amplification and product detection system. In this aspect, the method comprises assembling a collection of aqueous oil matrices by aspirating the one or more non-miscible oils, the aspirating step comprising: (i) aspirating the encapsulation oil from an encapsulation oil input; (ii) aspirating the carrier oil from a carrier oil input; or (iii) aspirating the encapsulation oil from an encapsulation oil input and aspirating the carrier oil from a carrier oil input. The method also includes aspirating a volume of polynucleotide sample from a polynucleotide sample input; aspirating a volume of reagents from a PCR reagent mix input; dispensing the volume of polynucleotide sample, the volume of reagents, and the one or more non-miscible oils into the plurality of vessels, wherein the volume of polynucleotide sample and volume of reagents form an aqueous reaction mix, and wherein components of the aqueous reaction mix do not mix with the one or more non-miscible oils; wherein steps 1), 2), and 3) are performed in any order or simultaneously, and wherein steps 1), 2), and 3) are performed prior to step 4). The method also comprises uniformly heating each volume of the aqueous oil matrix, wherein the heating comprises: 1) positioning the electromagnetic radiation source in optical communication with each vessel containing the aqueous oil matrix; 2) heating the volume of the aqueous oil matrix until it reaches a temperature in the range of about 50° C. to about 65° C.; 3) further heating the volume of the a aqueous oil matrix until it reaches a temperature in the range of about 65° C. to about 75° C.; and 4) further heating the volume of the aqueous oil matrix until it reaches a temperature in the range of about 90° C. to about 99° C. In this embodiment, an additional step in the method comprise cooling each aqueous oil matrix by positioning each of the vessels in close proximity to the cooling mechanism until the aqueous oil matrix reaches a temperature in the range of about 55° C. to about 65° C.

Further steps include measuring the fluorescence emission from each vessel containing the aqueous oil matrix, wherein the measuring comprises: 1) positioning a first optical member in optical communication with each vessel containing the aqueous oil matrix, wherein each first optical member is configured to provide an optical path for fluorescence excitation light having a first spectral wavelength from the one or more fluorescence excitation light sources to one of said vessels containing the aqueous oil matrix when the vessel is in a PCR product detection position, wherein the volume of the aqueous reaction mix comprises a first reagent capable of excitation by the fluorescence excitation light having the first spectral wavelength when the first reagent hybridizes to the polynucleotide sample, and wherein each first optical member is further configured to provide an optical path for fluorescence emission light from the aqueous reaction mix to the one or more fluorescence emission light sensing devices; and 2) measuring the signal produced by the one or more fluorescence emission light sensing devices from at least one aqueous reaction mix. In a particular aspect, the heating, cooling, and measuring the fluorescence steps are repeated for a predetermined number of additional cycles.

BRIEF DESCRIPTION OF THE DRAWINGS

FIG. 7 depicts a side view of an embodiment of a photonic heating subsystem and a moving belt.

DETAILED DESCRIPTION

Figure 1:
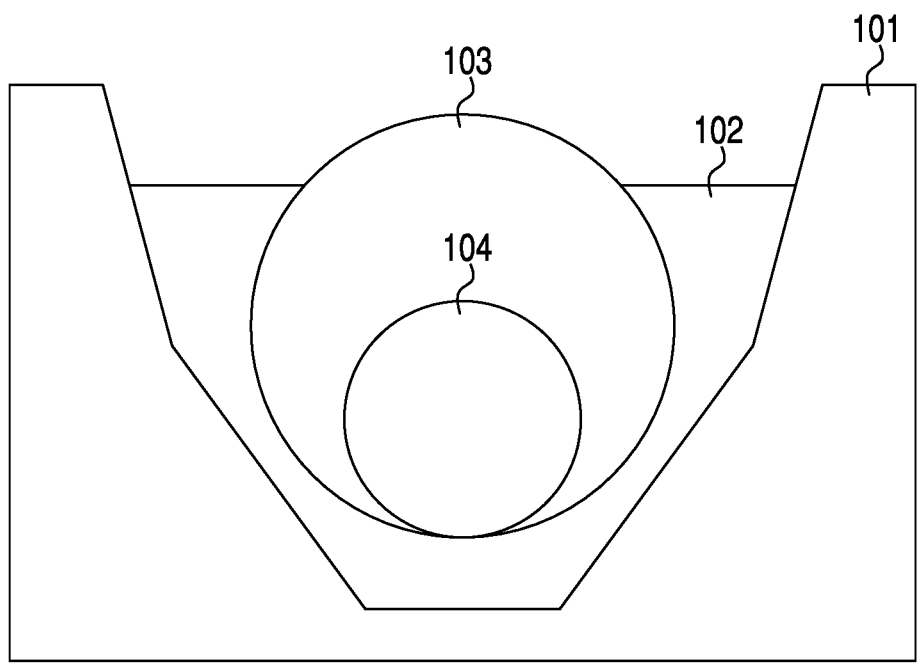
FIG. 1 depicts a cross-section view of an embodiment of a two oil aqueous oil matrix.

The disclosures herein will be described more fully hereinafter with reference to the accompanying drawings, in which some, but not all possible embodiments are shown. Indeed, disclosures may be embodied in many different forms and should not be construed as limited to the embodiments set forth herein; rather, these embodiments are provided so that this disclosure will satisfy applicable legal requirements.

Many modifications and other embodiments disclosed herein will come to mind to one skilled in the art to which the disclosed devices, systems, and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. Although specific terms are employed herein, they are used in a generic and descriptive sense only and not for purposes of limitation.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

It is also to be understood that the terminology used herein is for the purpose of describing particular aspects only and is not intended to be limiting. As used in the specification and in the claims, the term "comprising" is to be interpreted as specifying the presence of the stated features, integers, steps, or components as referred to, but does not preclude the presence or addition of one or more features, integers, steps, or components, or groups thereof. Thus, for example, aqueous reaction mix volume comprising one pair of nucleic acid primers may have two or more pairs of nucleic acid primers. Additionally, the term "comprising" is intended to include embodiments encompassed by the terms "consisting essentially of" and "consisting of." Similarly, the term "consisting essentially of" is intended to include embodiments encompassed by the term "consisting of."

Unless defined otherwise, all technical and scientific terms used herein have the same meaning as commonly understood by one of ordinary skill in the art to which the disclosed compositions and methods belong. In this specification and in the claims which follow, reference will be made to a number of terms which shall be defined herein.

The term "about" refers to the variation in the numerical value of a measurement, e.g., temperature, length, width, height, wavelength, etc., due to typical error rates of the device used to obtain that measure. In one embodiment, the term "about" means within 5% of the reported numerical value.

Provided herein are systems and methods for light-mediated polymerase chain reaction (PCR) amplification and product detection in which direct, uniform heating is applied to an aqueous reaction mix volume comprising a polynucleotide sample and PCR reagents, primers, and probes. Preferably, the aqueous reaction mix volume is positioned within (i.e., encapsulated) a non-miscible oil and, in some embodiments, additionally positioned on a free surface of a second non-miscible oil. In particular embodiments, the aqueous reaction mix volume does not mix with the non-miscible oils, and the combination of the aqueous reaction mix volume with one non-miscible oil or two non-miscible oils will form an arrangement referred to herein as an "assembled aqueous oil matrix" or "aqueous oil matrix" (see FIG. 1). The aqueous oil matrix enables efficient heating of very small aqueous reaction mix volumes without causing water evaporation. Aqueous reaction mix volumes suitable for use with the present methods and systems can be as little as 10 μL or less, and in some cases, an aqueous reaction mix volume as little as 5 nL can be used. What is more, the addition of one or two non-miscible oils provides a contamination barrier allowing reuse of microtiter dishes and other container vessels with little risk of polynucleotide cross-contamination between experiments.

In particular aspects, light-mediated heating is applied directly to the aqueous reaction mix volume, the aqueous oil matrix, or the vessel containing the aqueous oil matrix, using a plurality of energy sources that emit electromagnetic radiation in a process sometimes referred to herein as "photonic heating". Suitable energy sources include halogen lamps, lasers, and other light emitting devices. In a particular embodiment, uniform heating is applied directly to the aqueous reaction mix volume using a plurality of energy sources that emit infrared light having a spectral wavelength from about 1,300 nm to about 2,200 nm. Infrared light over this range of wavelengths is highly absorbed by the water molecules in the aqueous reaction mix volume and causes the temperature of the aqueous reaction mix reaction volume to rise rapidly. In another embodiment, direct and uniform heating is accomplished using plasmonic photothermal light-to-heat conversion via photon-electron-photon coupling (see Ho Son et al., 2015, Light: Science Appl. 4:e280, the content of which is incorporated herein by reference in its entirety). In such an embodiment, ultraviolet or visible light having a spectral wavelength from about 100 nm to about 500 nm is directly applied to a plasmonic excitable metal, such a thin gold film, which, in turn conducts heat to the aqueous oil matrix and/or the aqueous reaction mix volume. Thus, the present systems and methods allow for efficient and uniform heating of large numbers of PCR reactions with very small aqueous volumes thereby conserving energy, biological material, and PCR reagents.

Provided herein is a partially or fully automated and controlled system, and methods for using the same. In a particular aspect, the system comprises multiple integrated subsystems that perform one or more functions for carrying out PCR amplification of DNA samples and the detection of the resulting PCR products. In such aspects, the system comprises an assembly subsystem for dispensing the aqueous oil matrices in vessels or containers suitable for PCR processing; a reaction by reaction light-driven, or photonic, heating subsystem comprising multiple light sources configured to emit electromagnetic radiation to individual vessels; a reaction-by-reaction temperature monitoring subsystem configured to monitor the temperature of the aqueous oil matrix and/or the aqueous reaction mix volume in each vessel; a temperature feedback subsystem (e.g., via microcontroller) that controls the energy output of each individual light-driven heating source in response to temperature readings of each individual vessel; a fluorescence detection subsystem configured to detect the fluorescence light emission produced by the PCR products; and a mechanical, electrical, and software control system configured to control the assembly system and move the vessels containing the aqueous oil matrices through the various subsystems and vessel stations of the system via a positioning device, such as on a moving belt comprised of dimples or wells that serve as the vessels. The temperature feedback subsystem and the mechanical, electrical, and software control system are sometimes collectively referred to herein as the "control system." In some embodiments, the present system may include a laboratory information management system (LIMS) for tracking the vessels, polynucleotide sample data, PCR reagents data, and for converting fluorescence data into genetic information.

Assembly of the Aqueous Oil Matrices

In certain aspects, the present system includes an assembly subsystem or fluid handling station for dispersing the aqueous reaction mix volumes and non-miscible oils in the vessels that will be moved from the assembly subsystem to the photonic heating, temperature monitoring, and fluorescence detection subsystems. In one embodiment, a biological sample comprising isolated nucleic acids (e.g., genomic DNA, cDNA, and mRNA) is analyzed in the present system and methods. In some embodiments, the sample comprises isolated genomic DNA extracted from, e.g., biological tissue, using any suitable extraction technique known in the art and is admixed with PCR reagents that include one or more nucleic acid probes designed to specifically hybridize to a target DNA sequence. For instance, it may be desired to determine the presence of a particular polymorphic allele. In such aspects, allele specific probes can be used to detect the presence of the particular allele of the polymorphism, wherein each allele specific probe specifically hybridizes to one of the polymorphic alleles under stringent hybridization conditions. Typically, this detection method may comprise isolating the genomic DNA, amplifying the genomic DNA encompassing the polymorphic locus, and detecting the amplified polymorphic allele. PCR, RT-PCR, and LCR are common amplification and amplification-detection methods for amplifying the nucleic acids of interest. Details regarding these use of these and other amplification methods are well known in the art and can be found in a variety of standard texts and numerous references, such as Mullis et al. (1987) U.S. Pat. No. 4,683,202; Arnheim & Levinson (1990) C&EN 36-47; Kwoh et al. (1989) Proc Natl Acad Sci USA 86:1173; Guatelli et al. (1990) Proc Natl Acad Sci USA 87:1874; Lomell et al. (1989) J Clin Chem 35:1826; Landegren et al. (1988) Science 241:1077-1080; Van Brunt (1990) Biotechnology 8:291-294; Wu & Wallace (1989) Gene 4:560; Barringer et al. (1990) Gene 89:117; and Sooknanan & Malek (1995) Biotechnology 13:563-564.

In certain embodiments, each aqueous reaction mix volume includes a polynucleotide sample and a PCR reagent mixture. In such embodiments, the PCR reagents will include one or more nucleic acid probes and one or more nucleic acid primers. In a preferred embodiments, the PCR reagent mixture includes at least two different nucleic acid probes designed that specifically hybridize to different polymorphic alleles, i.e., probes designed to specifically hybridized to sequences containing different alleles. Further, allele-specific nucleic acid probes may be conjugated or covalently linked to different detectable labels capable of being distinguished using detection techniques available in the art. Detectable labels suitable for use with nucleic acid probes include, for example, any composition detectable by fluorescence emission light sensing devices. Labeling strategies for labeling nucleic acids and their corresponding detection strategies can be found, e.g., in Haugland (1996) *Handbook of Fluorescent Probes and Research Chemicals Sixth Edition* by Molecular Probes, Inc. (Eugene, Oreg.); or Haugland (2001) *Handbook of Fluorescent Probes and Research Chemicals Eighth Edition* by Molecular Probes, Inc. (Eugene, Oreg.). In a preferred embodiment, reagents (e.g., nucleic acid probes) are provided, wherein each reagent is covalently linked to a fluorophore.

In preferred embodiments, the detectable labels may also include reporter-quencher pairs, such as are employed in Molecular Beacon and TAQMAN® probes. The reporter may be a fluorescent organic dye modified with a suitable linking group for attachment to the oligonucleotide, such as to the terminal 3' carbon or terminal 5' carbon. The quencher may also be an organic dye, which may or may not be fluorescent. Generally, whether the quencher is fluorescent or simply releases the transferred energy from the reporter by nonradiative decay, the absorption band of the quencher should at least substantially overlap the fluorescent emission band of the reporter to optimize the quenching. Non-fluorescent quenchers or dark quenchers typically function by absorbing energy from excited reporters, but do not release the energy radiatively.

Selection of appropriate reporter-quencher pairs for particular probes may be undertaken in accordance with known techniques. Fluorescent and dark quenchers and their relevant optical properties from which exemplary reporter-quencher pairs may be selected are listed and described, for example, in Berlman, *Handbook of Fluorescence Spectra of Aromatic Molecules,* 2nd ed., Academic Press, New York, 1971, the content of which is incorporated herein by reference. Examples of modifying reporters and quenchers for covalent attachment via common reactive groups that can be added to an oligonucleotide in the present invention may be found, for example, in Haugland (2001) *Handbook of Fluorescent Probes and Research Chemicals Eighth Edition* by Molecular Probes, Inc. (Eugene, Oreg.), the content of which is incorporated herein by reference.

Suitable examples of reporters, such as fluorophores, may be selected from dyes such as SYBR green, 5-carboxyfluorescein (5-FAM™ available from Applied Biosystems of Foster City, Calif.), 6-carboxyfluorescein (6-FAM), tetrachloro-6-carboxyfluorescein (TET), 2,7-dimethoxy-4,5-dichloro-6-carboxyfluorescein, hexachloro-6-carboxyfluorescein (HEX), 6-carboxy-2',4,7,7'-tetrachlorofluorescein (6-TET™ available from Applied Biosystems), carboxy-X-rhodamine (ROX), 6-carboxy-4',5'-dichloro-2',7'-dimethoxyfluorescein (6-JOE™ available from Applied Biosystems), VIC™ dye products available from Molecular Probes, Inc., NED™ dye products available from available from Applied Biosystems, and the like. Suitable examples of quenchers may be selected from 6-carboxy-tetramethylrhodamine, 4-(4-dimethylaminophenylazo) benzoic acid (DABYL), tetramethylrhodamine (TAMRA), BHQ-0™, BHQ-1™, BHQ-2™, and BHQ-3™, each of which are available from Biosearch Technologies, Inc. of Novato, Calif., QSY-7™, QSY-9™, QSY-21™ and QSY-35™, each of which are available from Molecular Probes, Inc., and the like.

In certain aspects, the aqueous reaction mix is positioned within a non-miscible oil, such as an encapsulation oil or carrier oil. It being understood that the aqueous reaction volume will have a density that is different than the encapsulation oil and/or the carrier oil. In one embodiment, the aqueous reaction mix and an encapsulation oil are dispersed within a vessel, wherein the aqueous reaction mix will have a density range within the values of about 900 kg/m$^3$ to about 1,200 kg/m$^3$ (e.g., an aqueous based solution of isolated DNA sample and PCR reagents having a total density of approximately 1,000 kg/m$^3$), whereas the encapsulation oil will have a density range within the values of about 700 kg/m$^3$ to about 990 kg/m$^3$, provided that the densities of the aqueous reaction mix and the encapsulation liquid do not overlap. A suitable encapsulation liquid includes, but is not limited to, phenylmethylpolysiloxane (silicone oil) having a density of approximately 920 kg/m$^3$. In another embodiment, the aqueous reaction mix volume and a carrier oil are dispersed within a vessel, wherein the aqueous reaction mix volume will have a density range within the values of about 900 kg/m$^3$ to about 1,200 kg/m$^3$ (e.g., an aqueous based solution of isolated DNA sample and PCR reagents having a total density of approximately 1,000 kg/m$^3$), whereas the carrier oil will have a density range within the values of about 1,300 kg/m$^3$ to about 2,000 kg/m$^3$. In some embodiments, the carrier oil is a fluorocarbonated oil (e.g., FLUORINERT™ FC-40) having a density of approximately 1,900 kg/m³ or a perfluorinated amine oil. In yet another embodiment, the aqueous reaction mix is positioned within a non-miscible encapsulation oil (e.g., a silicone oil with a density slightly greater than or equal to water but less than the carrier oil) and further positioned on a free surface of a mutually immiscible carrier oil (e.g., FLUORINERT™ FC-40). In a preferred embodiment, the aqueous reaction mix comprises an aqueous solution of sample polynucleotides and PCR reagents having a density between that of the carrier oil and the encapsulation oil. Suitable densities for the fluids range within the values from about 1,300 kg/m³ to about 2,000 kg/m³ for the carrier oil, about 700 kg/m³ to about 990 kg/m³ for the encapsulation oil, and about 900 kg/m³ to about 1,200 kg/m³ for the aqueous reaction mix. Suitable carrier oils include, but are not limited to, FLUORINERT FC-40™, FLUORINERT FC-70™, FLUORIDROP 40™, FLUORIDROP 7500™, KRYTOX GLP-100™, KRYTOX GLP-104™, and KRYTOX GLP-105™. The densities of carrier oils suitable for use with the present systems and methods may vary depending on formulation and temperature but are generally between 1,700 kg/m³ and 1,900 kg/m³. Suitable encapsulation oils are often pure silicone oils (polydimethylsiloxane [PDMS]) and include, but are not limited to, SigmaAldrich Silicone Oil (5, 10, 100 or 1000 cSt), CLEARCO PSF-20cSt™, DOW CORNING 200™, XIAMETER PMX-200™, GE SF96™, SHIN-ETSU KF-96™, MICROLUBROL MLT8™, and SUPERLUBE 56104™. The densities of encapsulation oils suitable for use with the present systems and methods may vary depending on formulation and temperature but are generally between 700 kg/m³ and 1100 kg/m³.

In certain embodiments, the sample and the encapsulation oil and/or carrier oil will be dispensed into a vessel or well of suitable volume (e.g., having a diameter of 1, 2, 3, 4, 5, 6, 7, 8, 9, 10, 11, 12, 13, 14, 15 mm, or more), such as in a PCR tube or tube-strip, standard microtiter plate (e.g., 96-, 192-, and 384-well microtiter plate), or ARRAY TAPE® continuous polymer strips and the like made from glass or plastic. In such an arrangement, very small aqueous reaction mix volumes may be heated without significant evaporation of the water molecules and without the need for a lid, coverslip, or other material to cover the opening of the vessel or well. With smaller aqueous reaction mix volumes, the energy required to apply the amount of heat necessary to perform PCR amplification of the polynucleotide sample can be decreased. While aqueous reaction mix volumes greater than 10 μL can be used with the present systems and methods, aqueous volumes suitable for use with the present systems and methods can be as small as 10, 9, 8, 7, 6, 5, 4, 3, 2, 1, 0.9, 0.8, 0.7, 0.6, 0.5, 0.4, 0.3, 0.2, 0.1 μL, or less. Such small aqueous reaction mix volumes can be dispersed within the vessels of the present disclosure via standard micro pipetting devices. In addition, aqueous reaction mix volumes as small as 100, 90, 80, 70, 60, 50, 40, 30, 20, 10, 9, 8, 7, 6, and 5 nL can be dispersed within the vessels of the present disclosure using acoustic droplet injection, such as that described in Ellson et al. (2003) JALA 8:29-34, the content of which is incorporated herein by reference in its entirety.

As shown in FIG. 1, the different densities of the fluids will enable the formation of a an exemplary aqueous oil matrix. In FIG. 1, a vessel 101 contains an aqueous oil matrix that includes a carrier oil (e.g., a fluorocarbonated oil) 102, an encapsulation oil (e.g., a silicone oil), and an aqueous reaction mix volume 104 (e.g., an aqueous volume containing isolated polynucleotides, primers, probes, and other PCR reagents). As shown therein, the aqueous reaction mix volume 104 is positioned within the encapsulation oil 103. In addition, the aqueous reaction mix-in-encapsulation oil is positioned on a free surface of carrier oil 102. As a result of the aqueous oil matrix formation, the aqueous reaction mix volume 104 is centered in the vessel 101. The carrier oil 102 and encapsulation oil 103 prevent evaporation of water molecules in aqueous reaction mix volume 104, even when a small aqueous reaction mix volume (e.g., less than or equal to 10 μL) is subject to direct heating. The aqueous oil matrix configuration also prevents contamination of the vessel 101 as the aqueous reaction mix containing, e.g., nucleic acids, is unlikely to ever come into contact with the walls of vessel 101 due to the properties of the carrier oil 102 and encapsulation oil 103 and the surface tensions involved. In a preferred embodiment, the entire aqueous oil matrix can be aspirated from the vessel 101 thereby allowing reuse of vessel 101 with little risk of cross-contamination. Since the aqueous oil matrix centers the aqueous reaction mix volume 104, the ability to facilitate physical manipulations and to observe the aqueous reaction mix volume 104 for purposes such as fluorescence detection is greatly improved.

In another embodiment, a polysorbate additive is added to the encapsulation oil. In such embodiment, the polysorbate additive has a hydrophilic-lipophilic balance number in the range of 2 to 8. Exemplary polysorbate additives suitable for use in the present systems and methods, include, but are not limited to, SPAN® 80, SPAN® 65, and TWEEN® 20 (polysorbate-20). These additives within the encapsulation oil range from about 0.001% to about 10% of the mixture.

As noted above, the encapsulation oil and/or carrier oil of the present disclosure allow the use of very small aqueous reaction mix volumes (e.g., less than or equal to 10 μL). As a result, heat can be applied in the form of electromagnetic radiation to rapidly and uniformly raise the temperature of the aqueous reaction mix volume without requiring large energy inputs. For instance, the energy needed to raise the temperature of a 1 μL volume of water requires only milliWatts (mW) of laser output.

Also provided herein are fluid discharge members (e.g., micropipettors, acoustic droplet injectors) configured to discharge or dispense the aqueous reaction mix volume and the one or two non-miscible oils in a vessel or well for PCR amplification. In a preferred embodiment, an assembly subsystem is provided wherein one or more fluid discharge members are fully automated and programmed to dispense the desired volume of liquids. Automated pipetting and other similar liquid handling systems are well known in the art and perform programmed transfers of liquid between preselected collections of containers or vessels. In some embodiments, the assembly subsystem comprises one or more liquid discharge members for dispensing one or more of the aqueous reaction mix volume, encapsulation oil, and carrier oil into the vessels. In one embodiment, a collection of aqueous oil matrices range from 2-1,000 aqueous oil matrices, or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 48, 60, 72, 84, 96, 108, 120, 132, 144, 156, 168, 180, 192, 204, 216, 228, 240, 252, 264, 276, 288, 300, 312, 324, 336, 348, 260, 372, 384, 396, 408, 420, 432, 444, 456, 458, 460, 472, 484, 496, 508, 520, 532, etc.) are assembled in vessels for PCR amplification and detection. For high-throughput liquid handling, it may be desirable to configure the system to assemble and process the vessels using international configuration standards comprising loading and processing the vessels containing the aqueous oil matrices in rows of 12, however, the present systems and methods can be readily adapted to accommodate other desired configurations (e.g., rows of 2, 3, 4, 5, 6, 7, 8, 19, 10, 11, 13, 14, 15, 16, 17, 18, 19, 20, 21, 22, 23, 24, 25, 26, 27, 28, 29, 30, or more vessels). In some embodiments, one or more of the liquid discharge members comprise a pipetting head (e.g., a multichannel or single channel pipetting head) for liquid transfer. In some embodiments, one or more pipetting heads are placed on an automated axis system based on servo motors or stepper motors, wherein the one or more pipetting heads can be positioned over containers containing input fluids for aspirating the fluids and then positioned over vessels for dispensing the drawn input fluids into the vessels. The liquid discharge members can be configured for bulk dispensing of liquids or fitting with disposable tips for single or multi-channel dispensing of liquids.

In one particular embodiment, a set of liquid discharge members is configured to aspirate an encapsulation oil from an encapsulation input container and then automatically positioned over a row of vessels, wherein the set of liquid discharge members dispense the encapsulation oil into the vessels. In another embodiment, a set of liquid discharge members is configured to aspirate a carrier oil from a carrier input container and then automatically positioned over a row of vessels, wherein the set of liquid discharge members dispense the carrier oil into the vessels. In yet another embodiment, a set of liquid discharge members is configured to aspirate a polynucleotide sample (e.g., DNA sample of interest) from a sample input container and then automatically positioned over a row of vessels, wherein the set of liquid discharge members dispense the polynucleotide sample into the vessels. In still other embodiments, a set of liquid discharge members is configured to aspirate a volume of PCR reagents (e.g., salts, buffers, enzymes, dNTPs) from a PCR reagent input container and then automatically positioned over a row of vessels for dispensing the reagents into the wells. In such embodiments, suitable amplification primers and allele-specific nucleic acid probes can also be included in the PCR reagent input. In others, another set of liquid discharge members is configured for aspirating and dispensing the primers and probes. It being understood that the components of the aqueous reaction mix volume (i.e., polynucleotide sample, primers, probes, and PCR reagents) can be pre-mixed, aspirated and dispensed by the same or different liquid discharge members and in any order. In addition, the polynucleotide sample can be pre-mixed with the primers, probes, and PCR reagent and then aspirated by the liquid discharge members for dispensing in one or more vessels. Alternatively, the liquid discharge members can be configured to dispense the polynucleotide samples and primers/probes/PCR reagents separately. The assembly subsystem of the present disclosure can be programmed to assemble the aqueous oil matrices in any order and for any combination of polynucleotide samples and primer/probes/PCR reagents, e.g., for PCR amplification and detection on one or more polynucleotides samples using one or more distinct sets of primer/probe combinations. Adapting automated pipetting and other liquid handling systems to a workspace for any number of programmable liquid assembly operations is well within the skill of the ordinary artisan, and such liquid handling systems are available from original equipment manufacturer (OEM), commercial product, and automation/integration providers including, but not limited to, 3Dispense, Accel Biotech, Inc., Agilent Technologies, Inc., Apricot Designs, AsysTek, Aurora Biomed, Beckman Coulter, Biohit (Sartorius), BioNex Solutions, BioTek, CyBio (Analytic Jena), Dispendix, Dynamic Devices, FluidX, Formulatrix, Gilson, Hamilton, HTZ, Hudson Robotics, Integra Biosciences, Kawator, Labcyte, Nanoscreen, Perkin Elmer, Rainin, Scineon, Seyonic, Synchron, Tecan, Xantus, Xiril (SIAS), and Zinsser North America.

In a particular embodiment, primers, probes, and PCR reagents are optimized for detection of a particular polymorphic marker and combined in a single input. In such an embodiment, four sets of liquid discharge members are arranged such that the carrier oil and encapsulation oil are bulk dispensed into a row of vessels, followed by the dispensing of the polynucleotide samples and then the PCR reagents required for a particular marker detection (see, e.g., FIG. 9). While one or two non-miscible oils, polynucleotide sample volume, primers, probes, and PCR reagents can be dispensed into the vessels in any order, it is preferable to dispense the one or more non-miscible oils into the vessels prior to dispensing the polynucleotides to prevent contamination of the vessels. In some embodiments, multiple sets of discharge members are configured to match the number of vessels in a row, e.g., liquid discharge members configured with 12 pipetting tips at a spacing equal to that of the vessels in each row.

Suitable vessels used to contain the aqueous oil matrices include, but are not limited to, 96-well microtiter plates with workable volumes ranging from about 15 µL to about 100 µL and diameters of about 3 mm to about 6 mm, 384-well microtiter plates with volumes ranging from about 2 µL to about 40 µL and diameters of about 2 mm to about 4 mm, 384-well or 1536-well Array Tape® with vessel volumes ranging from about 0.5 µL to about 2 µL and diameters of about 0.5 mm to about 3 mm, or a dimpled-well belt or chain on a track assembly with vessel volumes ranging from about 1 µL to about 20 µL and diameters of about 0.5 mm to about 4 mm (see FIGS. 4A and 4B), and the like. It is preferred that the vessels for use herein be transparent and made from plastic or glass.

Photonic Heating Subsystem

In certain aspects of the disclosure, reaction-by-reaction light-mediated heating, or photonic heating, is applied to each vessel and/or directly to each aqueous reaction mix volume to raise the temperature of the aqueous reaction mix volume according to the timing and temperatures required for a particular PCR temperature cycle, it being understood that the term "reaction-by-reaction" refers to the application of electromagnetic radiation (and temperature measurement) to each individual aqueous reaction mix volume and/or aqueous oil matrix as opposed to a system utilizing constant temperature zones or photonic heating of multiple reactions simultaneously by a single light source under single control. It is well known in the art that PCR amplification of double stranded DNA requires an initial denaturing of the DNA ("hot start") following by multiple cycles of annealing, elongation, and denaturation. Suitable temperatures for the denaturation step are in the temperature range from about 90° C. to about 99° C., e.g., about 90° C., 91° C., 92° C., 93° C., 94° C., 95° C., 96° C., 97° C., 98° C., or 99° C. Preferably, the denaturation temperature is about 95° C. After denaturation of the DNA, the temperature is lowered, e.g., via a heat sink or application of cool air, to an annealing temperature optimized for the hybridization of the primers and labeled probes to the target polynucleotide strand. In a preferred embodiment, the probes are covalently linked to a fluorophore capable of excitation by electromagnetic radiation having a certain spectral wavelength. The annealing temperature is typically optimized based upon the length and nucleic acid composition of the primers and/or probes using techniques well known in the art. For instance, the thermal melting point (Tm) can be approximated from the equation of Meinkoth et al., *Anal. Biochem.* 138:267-284 (1984): Tm=81.5° C.+16.6 (log M) 4−0.41 (% GC)−0.61 (% form)−500/L; where M is the molarity of monovalent cations, % GC is the percentage of guano sine and cytosine nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, Tm hybridization conditions can be adjusted to hybridize to sequences of the desired identity. For example, if sequences with >90% identity are sought, the Tm can be decreased 10° C. Generally, stringent conditions are selected to be about 5° C. lower than Tm for the specific sequence and its complement at a defined ionic strength and pH.

Suitable temperatures for the annealing step are in the temperature range from about 50° C. to about 70° C., e.g., about 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., or 70° C. Preferably the annealing temperature is in the range from about 50° C. to about 65° C. More preferably the annealing temperature is in the range from about 55° C. to about 65° C. After the primers and probes have annealed to their target polynucleotide sequence, the temperature is raised to allow for elongation of new polynucleotide strands from the hybridized primers. Suitable temperatures for the elongation step are in the range from about 65° C. to about 75° C., e.g., 65° C., 66° C., 67° C., 68° C., 69° C., 70° C., 71° C., 72° C., 73° C., 74° C., or 75° C. Preferably, the elongation step is carried out at about 70° C. After an initial denaturation step (i.e., a "hot start"), the systems and methods of the present disclosure comprise a plurality of PCR temperature cycles, ranging from 2 to 60, or more, e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, or more cycles, wherein each PCR temperature cycle comprises an annealing step, an elongation step, and a denaturation step. After each PCR temperature cycle, the temperature of each aqueous oil matrix is cooled to a temperature range from about 55° C. to about 65° C., e.g., 55° C., 56° C., 57° C., 58° C., 59° C., 60° C., 61° C., 62° C., 63° C., 64° C., or 65° C., prior to beginning the next annealing step. The aqueous oil matrices can be cooled by an active or passive cooling mechanism, such as a passive metal heat sink, actively circulating air currents, passively circulating air currents, a Peltier device, a circulating liquid or any combination thereof.

It is an aspect of this disclosure to provide for aqueous reaction mix volumes small enough (e.g., 10 µL or less) to allow for efficient and direct heating via an electromagnetic radiation source such that only a few seconds are required to achieve the annealing, elongation, and denaturation temperatures for each cycle. In some embodiments, a PCR cycle requires the application of electromagnetic radiation for a period of 20, 19, 18, 17, 16, 15, 14, 13, 12, 11, 10, 9, 8, 7, 6, 5, 4, 3, 2, 1 seconds or less.

Depending on the type of electromagnetic radiation emitted, the radiation heats the aqueous reaction mix volume by heat absorption of the water molecules in the aqueous reaction mix volume or by the heat absorption of heat absorptive pigments, thermochromic dyes, plasmon-excitable materials, or a combination thereof. It being understood that the heat absorptive pigments, thermochromic dyes, and/or plasmon-excitable materials may be disposed on the walls of the vessel or dispersed within the vessel and/or within the aqueous reaction mix volume. Exemplary electromagnetic radiation sources suitable for use with the present systems and methods include lasers, halogen lamps, laser diodes, and light emitted-diodes. The position of the vessel containing the aqueous oil matrix, wherein electromagnetic radiation is applied by a electromagnetic radiation source, is sometimes referred to herein as a "heating position." In some embodiments, the electromagnetic radiation source emits ultraviolet radiation having a spectral wavelength in the range from about 100 nm to about 350 nm. In other embodiments, the electromagnetic radiation source emits visible light having a spectral wavelength in the range from about 380 nm to about 700 nm. In a preferred embodiment, the electromagnetic radiation source emits blue light having a spectral wavelength in the range from about 350 nm to about 500 nm. In a more preferred embodiment, the electromagnetic radiation source emits blue light having a spectral wavelength in the range from about 350 nm to about 450 nm. In an even more preferred embodiment, the electromagnetic radiation source emits blue light having a spectral wavelength of about 450 nm. In yet other embodiments, the electromagnetic radiation source emits infrared radiation having a spectral wavelength in the range from about 1,200 nm to about 2,200 nm. In a preferred aspect, the electromagnetic radiation source emits infrared radiation having a spectral wavelength in the range from about 1,450 nm to about 1,600 nm (e.g., about 1,550 nm). Thus, an electromagnetic radiation source suitable for use in the present systems and methods will have a spectral wavelength ranging from about 100 nm to about 2,200 nm.

In some embodiments, the electromagnetic radiation sources are laser diodes. Laser diodes are relatively inexpensive, small, and reliable with a very long service life. Solid-state laser diodes suitable for use with the present systems and methods are similar to those found in many common electronic devices such as compact disc and digital versatile disc players or in optical fiber communication. The energy output from such a laser diode can be focused on a very small area (e.g., via a collimating lens), and laser diodes are commercially available in a wide variety of spectral output wavelengths and wattages. In addition, the energy needed to raise the temperature of a aqueous reaction mix having a very small volume, e.g., approximately 5 µL, 1 µl, or less, is very small. Therefore, the energy output required for the laser diodes suitable for use with the present system is very small, e.g., from about 10 mW to about 500 mW, depending on the thermal mass of the vessel and oil matrix volume. In one aspect, an electromagnetic radiation source, e.g., a laser diode, is provided for emitting infrared radiation having a spectral wavelength in the range from about 1,200 nm to about 2,200 nm to a vessel containing an aqueous oil matrix, wherein a volume of the aqueous reaction mix comprises a polynucleotide sample to be analyzed by PCR genotyping (e.g., for end-stage PCR product detection or real-time PCR product detection). By selecting a spectral wavelength that is preferentially absorbed by the water molecules in the aqueous reaction mix volume rather than by the encapsulation and/or carrier oil and/or the vessel material (e.g., glass or plastic), the energy output can be concentrated on the aqueous reaction mix volume in the aqueous oil matrix.

In a preferred embodiment, the aqueous reaction mix volume is centered within an aqueous oil matrix, and the spectral wavelength of the infrared radiation is about 1,550 nm. In such an aspects, a laser diode for emitting the infrared radiation may be positioned above the vessel or below the vessel. It is known in the art that infrared radiation is readily absorbed by water molecules. Therefore, the infrared radiation may be focused directly on the aqueous reaction mix volume wherein heat is readily absorbed by the water molecules within to directly heat the aqueous reaction mix. It is to be understood that the laser diode is placed within close proximity to the vessel at a distance that may vary depending on how the infrared light is focused. An exemplary laser diode configured for the emission of infrared radiation will comprise a power source and an optional lens or an optional collimator for adjusting the focus of the infrared beam. In some embodiments, the laser diode may comprise one or more optical fibers or light pipes for providing an optical pathway for the infrared radiation and allowing for flexibility in positioning of the laser diode in relation to the vessel. For direct heating of the aqueous reaction mix volume, the laser diode may be placed at a distance of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 cm, or more from either the top of the vessel or the bottom of the vessel, and the lens or collimator may be used to focus the infrared radiation on the aqueous reaction mix volume. For uniform and efficient heating of the aqueous reaction mix, the infrared beam will be focused such that the size of the beam is approximately equivalent to the size of the aqueous reaction mix volume.

The amount of time needed to heat the sample for each PCR cycle can be calculated based on the specific heat of water (i.e., 4.184 J/g° C.) and the power output used for the laser and the heat dissipation rate of the materials and vessels. For instance, depending on specific total thermal mass and heat dissipation properties, a 1550 nm laser diode powered by 50 mW may be focused on the aqueous reaction mix having a volume of about 1 µL. Thus, the temperature of the aqueous reaction mix, can be heated from ambient, or room temperature, to about 60° C. in approximately 1 second, and then to about 70° C. in another 0.8 seconds, and then to about 95° C. in as little as 2 seconds. Therefore, a laser diode can be used to emit infrared radiation to heat the volume of the aqueous reaction mix through one PCR temperature cycle in about 3.3 seconds. Each individual PCR temperature cycle can be performed on an aqueous reaction mix volume with one laser diode. However, with larger aqueous reaction mix volumes (e.g., 5 µl) and an infrared light-emitting laser diode using a low energy input (e.g., about 80 to about 200 mW), inefficiencies occur in the absorption of infrared light by water and the heat conducted into the surrounding encapsulation fluid and/or carrier fluid and even into the vessel walls. At this point, the heat being conducted into the oil and glass from the aqueous reaction mix volume may balance the energy being put into the aqueous reaction mix volume by the laser diode and results in inhibition of temperature elevation. However, it being understood that it is well within the skill of the ordinary artisan to optimize the system for use depending on the materials selected for the encapsulation fluid or carrier fluid, the volume of the aqueous reaction mix, and the power output of the laser. For instance, the volume of the aqueous reaction mix can be reduced by about 2-fold to about 100 fold, or more (e.g., 1,000-fold via an acoustic transfer), the power of the laser diode can be increased to transfer energy into the vessel at a rate greater than the rate of loss, and/or the absorption of available light energy for the conversion to heat can be improved such that heat is conducted to the aqueous reaction mix volume increased rate compared to the rate of heat loss. In an embodiment, heat absorption is improved using heat absorbing dyes and particles, and/or aqueous oil matrices are used to enable the use of smaller volumes of aqueous reaction mix (e.g., less than 5 µL).

Figure 2:
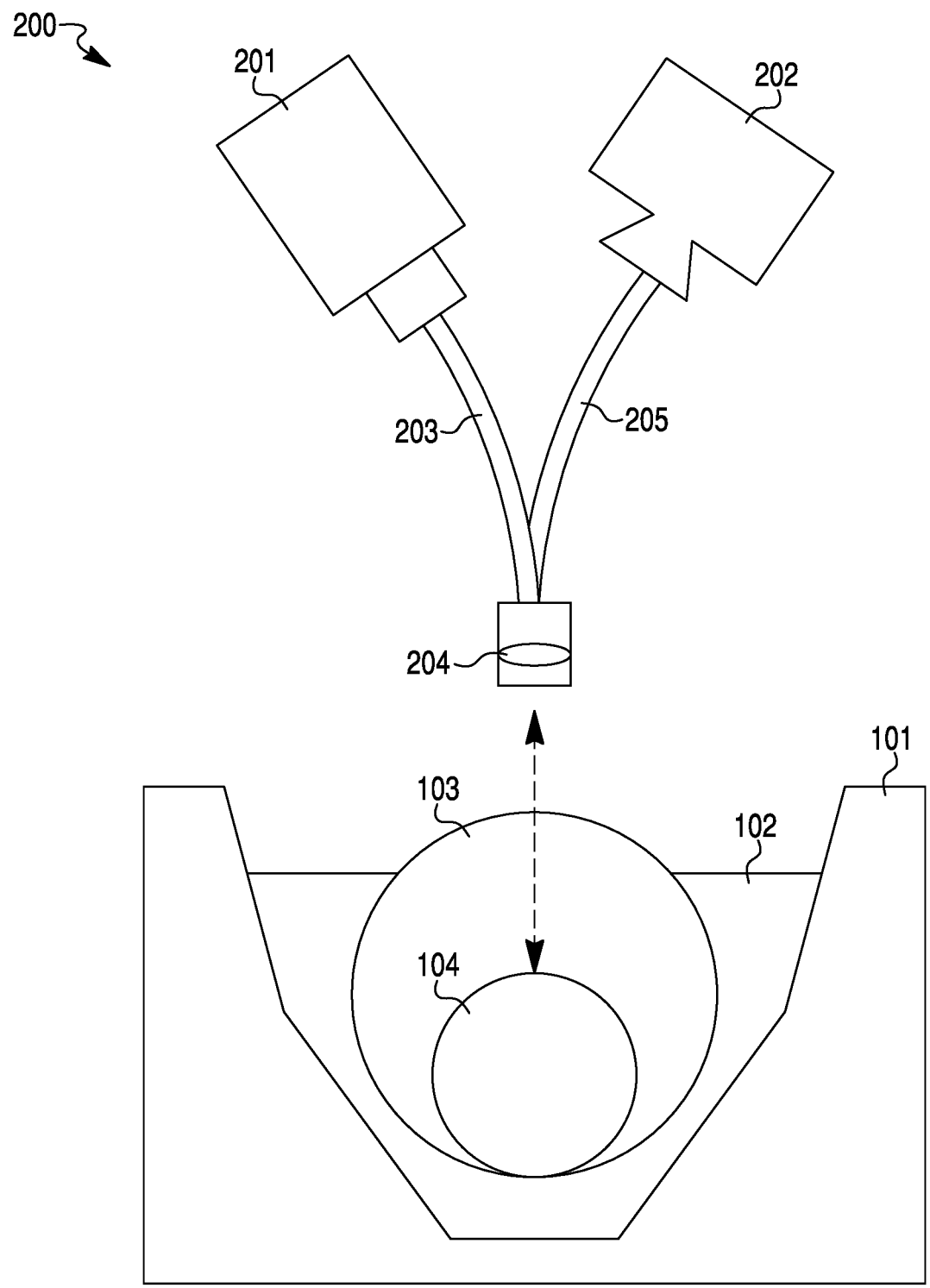
FIG. 2 depicts a cross-section view illustrating an exemplary configuration where the electromagnetic radiation source and at least one detector is located in the same position at the top of a vessel.

Depicted in FIG. 2 is an exemplary configuration of the present system. In this embodiment, the electromagnetic radiation source 201, e.g., a laser diode emitting infrared radiation, is positioned at the top of vessel 101. Electromagnetic radiation is carried, or conducted, along an optical path by an optical fiber or light pipe 203 and focused on the aqueous reaction mix volume 104 via a collimator lens 204.

In an alternative embodiment, an electromagnetic radiation source, e.g., light-emitting diode (LED), is provided for emitting blue light having a spectral wavelength in the range from about 350 nm to about 450 nm (or ultraviolet or violet light having a spectral wavelength from about 100 nm to about 350 nm) to a vessel containing an aqueous oil matrix, wherein the aqueous reaction mixture volume comprises a polynucleotide sample to be analyzed by PCR genotyping. In a preferred embodiment, the aqueous reaction mixture volume is positioned within two non-miscible oils, such as the exemplary aqueous oil matrix depicted in FIG. 1. In such an embodiment, and LED is positioned within optical communication with vessel and emits electromagnetic radiation having a spectral wavelength of about 450 nm (i.e., blue light). In such an aspects, an LED for emitting the blue light may be positioned above the vessel or at the bottom of the vessel. While water molecules do not readily absorb blue light radiation, the aqueous reaction mix volume can be uniformly heated by the LED light source using plasmon excitable particles in the aqueous reaction mix volume. Plasmon excitable materials that readily absorb blue light can emit heat by a process known in the art as photothermal light-to-heat conversion via photon-electron-phonon coupling. Suitable plasmon excitable particles for absorbing blue light radiation are known in the art and include, but are not limited to particles comprising gold, silver, nickel, platinum, or a combination thereof. Preferably, the plasmon excitable material is gold. The use of gold in photonic PCR is described in detail in Ho Son et al. (2015), the content of which is incorporated by reference herein in its entirety. Alternatively, selected walls of the vessels may be coated in plasmon excitable material (e.g., gold particles) by electrolysis or vapor-deposition. In a preferred embodiment, a thin film or layer comprising plasmon excitable material is dispersed in the vessel at or near the bottom of the vessel such that the thin film or layer is within the aqueous oil matrix, but within or underneath the aqueous reaction mix (see, e.g., FIG. 3). In a more preferred embodiment, a thin film or layer of gold is placed inside the vessel and at the bottom of the vessel such that the thin film or layer is in intimate contact with the aqueous oil matrix and between the aqueous reaction mixture and the bottom of the vessel. In some aspects, a Mylar disk comprising the thin layer of gold is placed in the vessel and at the bottom of the vessel. In other aspects, a gold-coated aluminum foil disk is placed in the vessel at the bottom of the vessel. The thickness of the thin film or layer of plasmon excitable material is in the range from about 10 nm to about 100 nm, e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 91, 91, 92, 93, 94, 95, 96, 97, 98, 99, or 100 nm. In other embodiments, the thickness of the thin film or layer of plasmon excitable material is in the range from about 50 nm to about 500 nm, e.g., 50 nm, 60 nm, 70 nm, 80 nm, 90 nm, 100 nm, 200 nm, 300 nm, 400 nm, or 500 nm. Thicker films or layers of metallic material, up to about 1 mm thick or more, can absorb light and convert the light energy to heat, but surface plasmonic resonance is reduced which slows heating. In other embodiments, the material coated with the then layer of gold (e.g., Mylar, glass, aluminum foil, or various other plastics) may constitute the bottom of the vessel or may be positioned on the bottom of the vessel wall. In some embodiments, the LED is positioned at the top or the bottom of the vessel and focused (e.g., by a lens or collimator) to emit blue light radiation on the gold layer for conduction of heat into the aqueous droplet.

It is to be understood that the LED is placed within close proximity to the vessel at a distance that may vary depending on how the blue light is focused. An exemplary LED configured for the emission of blue light radiation will comprise a power source and a lens or a collimator for adjusting the focus of the light beam. In some embodiments, the LED may comprise one or more optical fibers or light pipes for providing an optical pathway for the LED and allowing for flexibility in positioning of the laser in relation to the vessel containing the sample. In other embodiments, the LED housing has a physical diameter less than the distance between the reaction vessels and is positioned directly beneath the vessel. In such embodiments, the small LED will be linked to the power source using conventional circuitry, and the LED will comprise a collimator to allow for beam focusing. For uniform heating of the aqueous droplet, the LEDs of the present disclosure may be placed at a distance of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 mm, or more from either the top of the vessel or the bottom of the vessel, and the optional lens or collimator may be used to focus the light beam on a thin layer of plasmon excitable material, such as gold. For uniform and efficient heating of the aqueous reaction volume, the blue light bean will be focused on the plasmonic excitable material such that the size of the beam is approximately equivalent to the surface area of the plasmonic excitable material. In a preferred embodiment, a Mylar disk comprising a thin layer of gold (e.g., between about 10 nm and 0.2 mm thickness) is placed in the vessel, and the blue light radiation emitted from the LED is focused such that the size of the beam is approximately equivalent to the size of the Mylar or aluminum foil disk and thin layer of gold.

Figure 3:
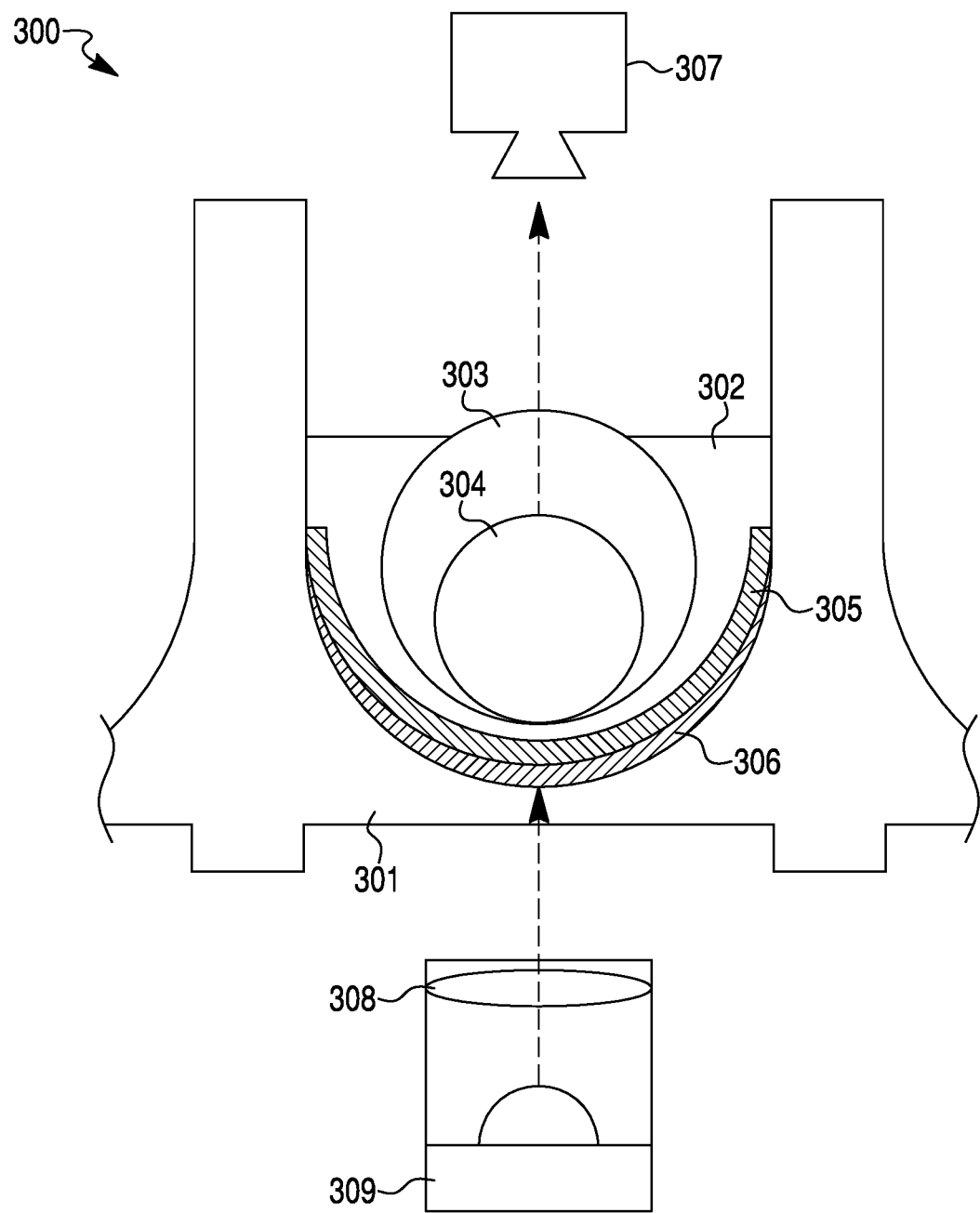
FIG. 3 depicts a cross-section view illustrating an exemplary configuration where the electromagnetic radiation source and at least one detector is located in the same position, wherein the electromagnetic radiation source is positioned at the bottom of a vessel and at least one detector is positioned at the top of the vessel.

Depicted in FIG. 3 is an embodiment of the disclosure comprising a electromagnetic radiation source for the emission of visible light (e.g., an LED emitting blue light). An aqueous oil matrix comprising an aqueous reaction mix volume 304 positioned within an encapsulation oil 303 and a carrier oil 302. In this exemplary embodiment, the electromagnetic radiation source 309 (e.g., an LED emitting blue light) is positioned in optical communication with the bottom of vessel 301 (e.g., a transparent plastic vessel). A thin layer of plasmonic excitable material 306 is dispersed in vessel 301 such that the plasmonic excitable material is positioned at the bottom of vessel 301 within or in contact with the carrier oil 302, but beneath the encapsulation oil 303 and aqueous reaction mix volume 304. As discussed herein, the plasmonic excitable material may be gold. Optionally, a passivation layer 305 made from any suitable material used in the art (e.g., plastic, dimethylsiloxane, or silicon dioxide) is disposed over the plasmonic excitable material 306 to prevent the PCR reaction components in the aqueous reaction mix volume 304 from reacting with the plasmonic excitable material 306. However, the aqueous oil matrix creates separation between the aqueous reaction mix volume 304 and the plasmonic excitable material 306 and decreases the likelihood that the PCR reaction components will react with the plasmonic excitable material. Depending on size and proximity of the LED to the plasmonic surface, an optional collimator lens 308 enables focusing of the light beam (dotted line) on plasmonic excitable material 306, which then converts the light energy to heat that is uniformly conducted to the aqueous reaction mix volume 304. In some embodiments, a detector 307 is positioned in optical communication with the top of vessel 301. The detector 307 may comprise any suitable detection device for the detection of thermal radiation (e.g., black body infrared radiation) and/or fluorescence emitted from the aqueous reaction mix volume (dotted line), as will be discussed in greater detail elsewhere herein.

The Belt Positioning Device

In certain aspects, the present systems and methods comprise a positioning device for discretely moving the vessels (e.g., step-by-step as opposed to continuous movement) containing the aqueous oil matrices through the various subsystems and vessel stations of the system. In one embodiment, the positioning device is a moving belt comprised of a plurality vessels (e.g., wells or dimples), wherein the vessels will contain the assembled aqueous oil matrices. The belt may be constructed of flexible plastic, thermoplastic polymers (e.g., polypropylene, polystyrene, or polycarbonate) or other materials similar to that used for ARRAY TAPE®. In some embodiments, the vessels are stamped into the belt material to form dimples. The volume of each well ranges from 0.2 μl to about 20 μl with a diameter of each vessel ranging from about 0.5 mm to about 4 mm depending on the desired design parameters. The belt, and the vessels within the belt, may be fabricated from one continuous material or may be fabricated in small segments, wherein each segment comprises a configured set of reaction vessels, and where the segments are attached, or chained together, by any suitable technique in the art, to constitute the belt. In such an embodiment, the segments can be interchanged or replaced as needed to simplify creation of optimal configurations for various vessels volumes and/or to support maintenance and/or repair. In a preferred embodiment, the belts will be joined end-to-end to form a loop structure and will operate via a motorized track communicatively connected to a mechanical and electronic control system, which will actuate the belt to move the vessels in discrete steps from the assembly subsystem through each of the heating positions, temperature monitoring positions, PCR product detection positions. In some embodiments, the belt will move the vessels to a waste disposal subsystem after completion of the PCR amplification and PCR detection cycles. Each actuation of the belt is followed by a stop (e.g., step-by-step movement) to position each row of vessels at the appropriate vessel station. The term "vessel station" as used herein refers to a particular physical location of a row or array of vessels in the system.

In some embodiments, vessel stations comprise: 1) assembly of the aqueous oil matrices via the assembly subsystem; 2) a heating position via the photonic heating subsystem; 3) a temperature monitoring position via the temperature monitoring subsystem; 4) a PCR product detection position via the fluorescence detection subsystem; and 5) optionally, waste disposal via the waste disposal subsystem. In other embodiments, vessel stations comprise: 1) assembly of the aqueous oil matrices via the assembly subsystem; 2) a heating position via the photonic heating subsystem, a temperature monitoring position via the temperature monitoring subsystem, and a PCR product detection position via the fluorescence detection subsystem; and 3) optionally, waste disposal via the waste disposal subsystem. In yet other embodiments, vessel stations comprise: 1) assembly of the aqueous oil matrices via the assembly subsystem; 2) a heating position via the photonic heating subsystem; 3) a temperature monitoring position via the temperature monitoring subsystem and a PCR product detection position via the fluorescence detection subsystem; and 4) optionally, waste disposal via the waste disposal subsystem. In a preferred embodiment, vessel stations comprise: 1) assembly of the aqueous oil matrices via the assembly subsystem; 2) a heating position via the photonic heating subsystem and a temperature monitoring position via the temperature monitoring subsystem; 3) a PCR product detection position via the fluorescence detection subsystem; and 4) optionally, waste disposal via the waste disposal subsystem. In yet other embodiments, addition vessel stations may be included in the system, such as vessel stations comprising a cooling position via an active or passive heat sink and a hot start position or positions via photonic heating.

Figure 4A:
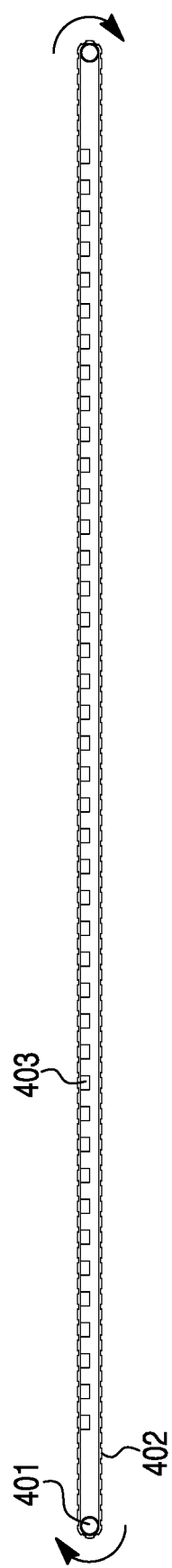
FIG. 4A depicts a side view of an exemplary belt device.
Figure 4B:
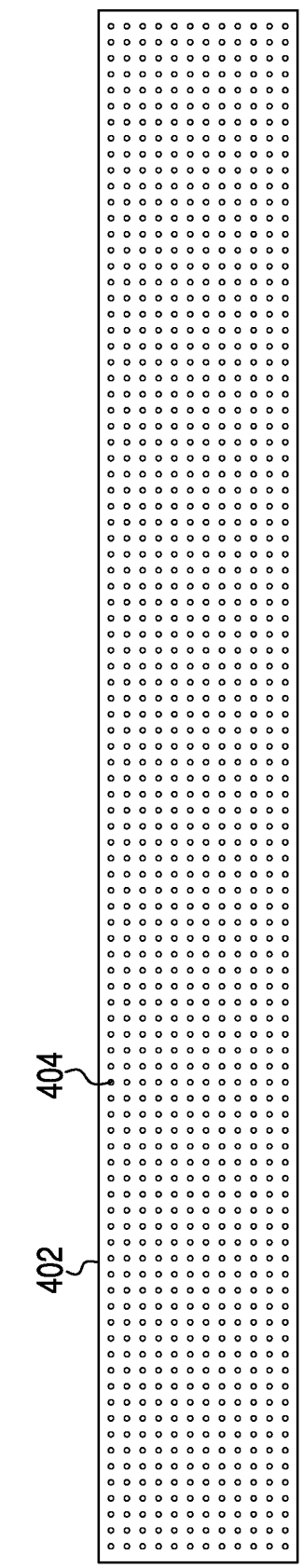
FIG. 4B depicts a top view of an exemplary belt device.

Depicted in FIGS. 4A and 4B are exemplary embodiments of a belt design suitable for use with the present system and methods. In this embodiment, a belt 402 is disposed on drive gears 401 at each end. In this embodiment, the mechanical and electronic control system will cause rotation of the drive gears 401 (indicated by arrow) to enable the belt to move each row of vessels in discrete steps through each vessel station. The belt 402 comprises a plurality of vessels 404 suitable for containing an aqueous oil matrix. Any variation of vessels spacing can be utilized. In a preferred embodiment, vessel spacing can be from about 1 mm to about 10 mm or more, e.g., 1 mm, 1.5 mm, 2 mm, 2.5 mm, 3 mm, 3.5 mm, 4 mm, 4.5 mm, 5 mm, 5.5 mm, 6 mm, 6.5 mm, 7 mm, 7.5 mm, 8 mm, 8.5 mm, 9 mm, 9.5 mm, 10 mm, or more. In a more preferred embodiment vessel spacing is in a range from about 8 mm to about 10 mm. In a most preferred embodiment, spacing of the vessels is about 9 mm to fit with international standards for well spacing in microtiter plates and standard tip spacing in multi-tip pipettors. In certain aspects, the belt will comprise rows of vessels, wherein each row will include any number of vessels ranging from 2 to 100 vessels, or more in each row. More preferably, the number of vessels in each row is 2, 3, 4, 5, 6, 7, 8, 19, 10, 11, 13, 12, 14, 15, 16, 17, 18, 19, 20, 21, 22, 23, 24, 25, 26, 27, 28, 29, 30, or more vessels. Shown in FIG. 4B is the most preferred embodiment, wherein each row of vessels in belt 402 comprises 12 vessels. The size and shape of each vessel can be designed based on the encapsulation oil volume such that the encapsulation oil is substantially stationary when positioned within the carrier oil thus maintaining the aqueous reaction mix volume substantially centered in the well. In this embodiment, a flexible belt 402 is disposed on drive gears 401 at each end. In this embodiment, the mechanical and electronic control system will cause rotation of the drive gears 401 in the direction of the arrow to enable the belt to move each row of vessels in discrete steps through each vessel station.

In some embodiments, the vessels of the belt may be coated (e.g., via electrolysis, vapor deposition, or emulsion painting) with a plasmonic excitable material, such as gold. In some embodiments the plasmonic excitable material is inserted into each vessel as a coated disk of Mylar, aluminum foil, or other suitable thin material carrier. Also shown in FIG. 4A is a plurality of passive heat sink metals 403 for cooling each row of vessels when at a vessel station in close proximity to a passive heat sink metal 403.

Temperature Monitoring Subsystem

While many traditional PCR systems comprise constant temperature zones for PCR thermocycling, the present systems and methods provide for direct heating and temperature monitoring of each vessel enabling the optimization and regulation of the PCR thermocycling conditions for each vessel. In addition, the present systems and methods can be programmed to run a plurality of different PCR thermocycling conditions to amplify and detect PCR products using a plurality of different polynucleotide samples with different primers, probes, and PCR reagents. Since the temperatures of the aqueous oil matrices in the vessels must be monitored to enable the present system to regulate the amount of energy to provide from the lasers to change the temperature of the vessel to the values desired for efficient PCR thermocycling, provided herein is a temperature monitoring subsystem. In some embodiments, the temperature monitoring subsystem collects temperature data from each of the vessels during, simultaneously with, or after each PCR temperature cycle that can be used to aid in quality control. In other embodiments, the temperature monitoring subsystem collects temperature data from each of the vessels during each PCR temperature cycle that can be used to determine a baseline temperature for optimization of the next heating cycle or, alternatively, for normalization of temperature-sensitive fluorophores. Aqueous oil matrices (or aqueous reaction mix volumes) that do not change temperature as expected can indicate incorrect volume dispensing of the assembly subsystem or instrument malfunction. In certain embodiments, temperature measurement information is available every 15 seconds or less as the system is running. In addition, some embodiments of the system incorporate software functionality that alert laboratory staff of any temperature inaccuracies. Such functionality can include, but is not limited to, alerts based on temperatures out of set limits, failures to detect expected temperature changes within expected time intervals during photonic heating, or temperature changes that are erratic or vary in unexpected ways. Software providing such functionality can be custom-coded or may utilize algorithms publicly or commercially available. The position of the vessel containing the aqueous oil matrix where temperature or thermal information is collected and monitored is sometimes referred to herein as a "temperature monitoring position."

In certain aspects, the temperature monitoring subsystem comprises a plurality of thermal detection devices each of which corresponds to a vessel containing an aqueous oil matrix. Suitable thermal detection devices are known in the art and include, but are not limited to, direct contact thermistors and/or thermocouples, non-contact thermal imagers, discrete thermopile sensors, thermopile arrays, other infrared sensors, or optical fibers and/or fiber optic arrays in optical communication with a non-contact thermal infrared sensing device. In some embodiments, the temperature monitoring subsystem comprises a plurality of thermal detection devices, e.g., thermistors or thermocouples, disposed within each of the vessels containing an aqueous oil matrix and configured to collect and send temperature data to the temperature monitoring subsystem via conventional circuitry or wireless communication. In a preferred embodiment, the temperature monitoring subsystem comprises a plurality of thermal detection devices (e.g., optical fibers or light pipes) in optical communication with a thermal infrared sensing device (e.g., thermal imaging camera or infrared sensor). In such an embodiment, each thermal detection device is in optical communication with each vessel containing an aqueous oil matrix when the vessel is in a temperature monitoring position, and wherein each thermal detection device is configured to provide a measuring signal that is dependent on the intensity of black-body infrared radiation emitted by the aqueous oil matrix as an indication of temperature. Further, each thermal detection device may be configured to provide a thermal radiation path from the volume of the aqueous oil matrix (or the aqueous reaction mix volume) to the thermal infrared sensing device for the collection of temperature data. In a preferred embodiment, the thermal detection devices are optical fibers or light pipes that are not dispersed in the vessels and do not make physical contact with the aqueous oil matrices. In some embodiments, the thermal detection devices, e.g., one or more optical fibers, detect emitted black body infrared radiation from each aqueous oil matrix (or aqueous reaction mix volume), which is then carried via a fiber optic array to a thermal infrared sensing device, such as an infrared-sensitive camera or thermal imager. The thermal infrared sensing device then measures the intensity of black body infrared radiation signal from each vessel and converts the intensity to temperature. In a more preferred embodiment, the black body radiation from each aqueous oil matrix is directly detected by an infrared-sensitive camera or thermal imager positioned in proximity to the reaction volumes such that the infrared radiation of one or more reaction volumes is simultaneously captured in a single image of the camera or imager.

In certain aspects of the present disclosure, a temperature measurement is taken from each vessel containing an aqueous oil matrix when that vessel is in a temperature monitoring position. In some embodiments, the temperature monitoring position is the same position as the heating position. In other words, the thermal detection devices are positioned at the same location (e.g., the same vessel station) as the electromagnetic radiation sources. In such embodiments, the electromagnetic radiation sources and thermal detection devices can be positioned in several suitable arrangements. In some embodiments, the electromagnetic radiation sources and the thermal detection devices can be positioned in proximity to the top of the vessels containing the aqueous oil matrices. Depicted in FIG. 2 is an embodiment of the present system where an electromagnetic radiation source 201 (e.g., laser diode or LED) and a detector 202 are positioned above vessel 101. The detector 202 may be a thermal infrared sensing device and/or a fluorescence detection device. In some embodiments, detector 202 is a combination of the thermal infrared sensing device and the fluorescence detection subsystem. Electromagnetic radiation is emitted from the electromagnetic radiation source 201 to the aqueous reaction mix volume 104 (dotted line) positioned within an aqueous oil matrix comprising an encapsulation oil 103 and a carrier oil 102. In this embodiment, electromagnetic radiation, such as infrared radiation, is carried, or conducted, along an optical path by an optical fiber or light pipe 203 and focused on the aqueous reaction mix volume 104 via a collimator lens 204. As the temperature rises, aqueous reaction mix volume 104 emits black body infrared radiation (dotted line) that is carried to a thermal infrared sensing device of detector 202 by an optical fiber 205. In other embodiments, the black body infrared radiation is carried to a thermal infrared sensing device of detector 202 via a bundle of optical fibers and/or an optical fiber array. However, if electromagnetic radiation source 201 emits infrared radiation, then electromagnetic radiation source 201 and the thermal infrared sensing device of detector 202 cannot operate simultaneously without interference of thermal detection. In such an arrangement, the electromagnetic radiation source 201 must be turned off while the thermal infrared sensing device of detector 202 is turned on. Near real-time temperature measurements can still be accomplished if the system is programmed to "flicker" the electromagnetic radiation source 104 and the thermal imaging device of detector 202. Flickering is well known in the art and comprises a rapid, alternating series of short infrared radiation pulses followed by thermal detection.

In some embodiments, the temperature monitoring position is the same position, e.g., vessel station, as the heating position, and the electromagnetic radiation sources are positioned in proximity to the bottom of the vessel containing the aqueous oil matrices while the thermal detection devices are positioned at the top of the vessel containing the aqueous oil matrices. Shown in FIG. 3, is a configuration where the electromagnetic radiation source 309 is positioned at the bottom of the vessel, and detector 307 is positioned at the top of the vessel. For temperature monitoring, detector 307 may be, e.g., an infrared sensor or an optical fiber(s) for providing a thermal radiation path to a thermal infrared imaging device.

Figure 5:
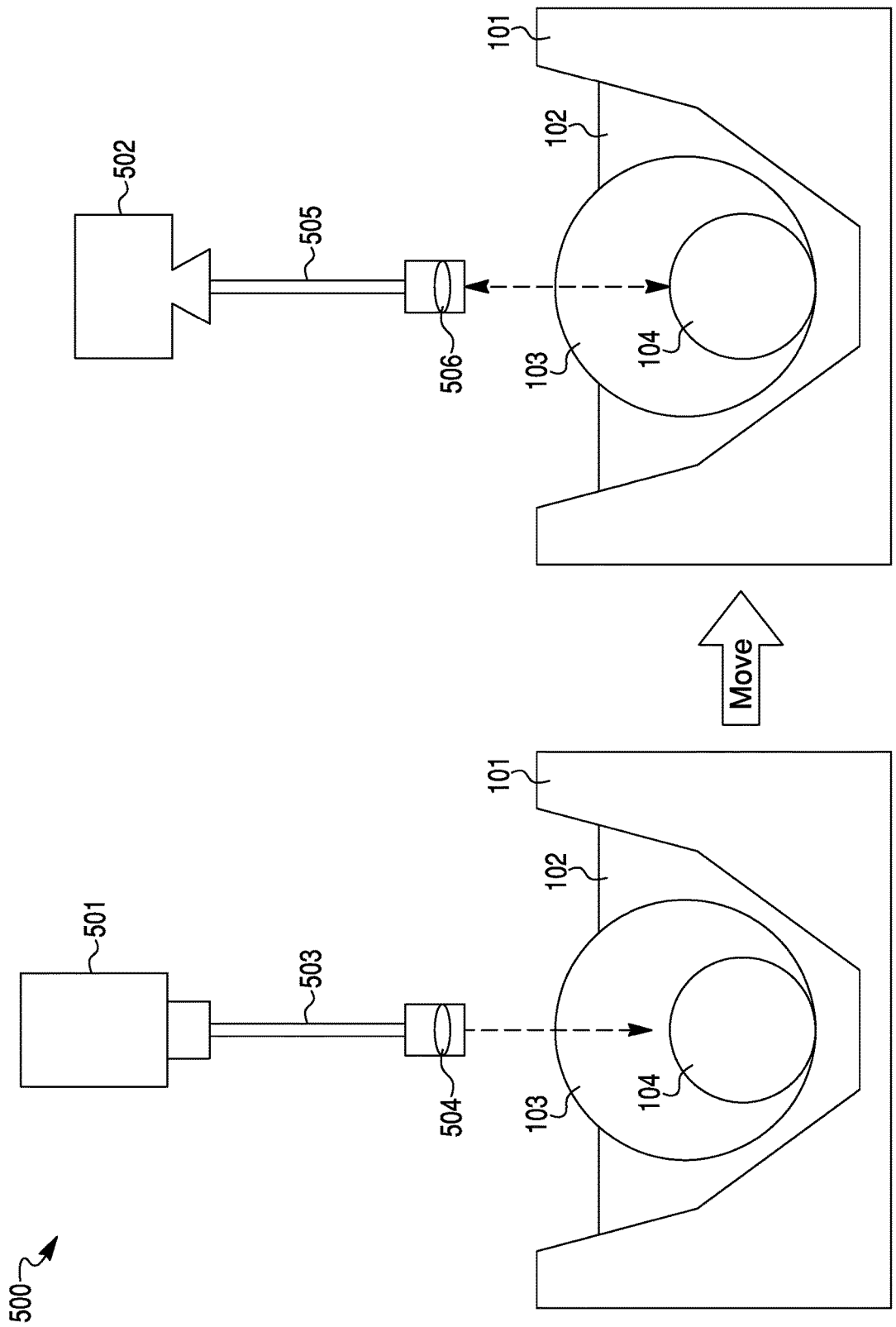
FIG. 5 depicts a cross-section view of an exemplary embodiment illustrating a configuration where the electromagnetic radiation source and at least one detector are at different positions.

In other embodiments, the temperature monitoring position is at a different position, e.g., vessel station, than the heating position. Shown in FIG. 5, is a configuration where an electromagnetic radiation source 501 is positioned at the top of vessel 101 when in the heating position. In this configuration, the vessel 101 is moved to a second vessel location where detector 502 is positioned at the top of the vessel when in the temperature monitoring position. The detector 502 can be a thermal infrared sensing device or a fluorescence detection device. In some embodiments, detector 502 is a combination of a thermal infrared sensing device and the fluorescence detection subsystem. Electromagnetic radiation is emitted from the electromagnetic radiation source 501 to the aqueous reaction mix volume 104 (dotted line) positioned within an aqueous oil matrix comprising an encapsulation oil 103 and a carrier oil 102. In this embodiment, electromagnetic radiation, such as infrared radiation, is carried along an optical path by an optical fiber or light pipe 503 and focused on the aqueous reaction mix volume 104 via a collimator lens 504. Following the heating step, vessel 101 is moved by a positioning device, e.g., a motorized belt-on-a track device, to the next vessel station where a thermal infrared sensing device of detector 502 measures the emission of black body infrared radiation from aqueous reaction mix volume 104. In some embodiments, the black body infrared radiation is carried to the thermal infrared sensing of detector 502 via an optical fiber and/or fiber optic array 505. In other embodiments, the black body infrared radiation is carried to the thermal infrared sensing of detector 502 via a bundle of optical fibers and/or a fiber optic array. In yet other embodiments the black body infrared radiation is detected directly by a non-contact infrared sensor or thermal imaging camera. In these arrangements, the temperature measurements cannot be collected simultaneously with application of photonic heating, but can be used to determine the baseline temperature of the aqueous oil matrices in between PCR cycles such that the system can adjust the amount of energy output needed to heat the aqueous reaction mix volume for the next PCR cycle, e.g., a microcontroller. Alternatively, the temperature measurements can be used to normalize the fluorescence emission of temperature-sensitive fluorophores.

Fluorescence Detection Subsystem

In certain aspects, the present systems and methods comprise a fluorescence detection subsystem configured to emit and detect fluorescence light for the detection of one or more fluorophore-labeled probes that have hybridized to a target polynucleotide sample. In some embodiments, the fluorescence detection subsystem comprises one or more fluorescence excitation light sources, one or more fluorescence emission light sensing devices, and a plurality of one or more optical members configured to provide an optical path for conducting fluorescence excitation light to each vessel in the PCR product detection position and for conducting fluorescence emission light from each vessel to the fluorescence light emission sensing device(s). The optical path, or optical connection, between the fluorescence excitation light source(s) and the corresponding vessel may comprise any one of a variety of optical arrangements and can include a variety of optics of conventional construction. Non-limiting examples of fluorescence emission light sensing devices suitable for use with the present systems and methods include, e.g., charge-coupled device (CCD) cameras, complimentary metal-oxide semiconductor (CMOS) cameras, photomultipliers, and sensor arrays. In addition, any suitable fluorescence excitation light source can be used in the fluorescence detection subsystem and include, but are not limited, to LEDs, laser diodes, argon ion lasers, xenon lamps, and the like. The fluorescence excitation light source can be configured to emit fluorescence light having a suitable spectral wavelength in the range from about 300 nm to about 1,200 nm depending on the particular fluorophore or fluorophores used in the PCR reaction. Fluorophores and other fluorescence-excitable species having a particular excitation/emission wavelength are well known and commercially available. Exemplary fluorophores and fluorescent dyes suitable for use with the present system and methods are provided in Table 1.

TABLE 1

Non-limiting list of commonly used fluorophores.

| Fluorophore | Excitation Wavelength (nm) | Emission Wavelength (nm) |
| --- | --- | --- |
| BIOSEARCH BLUE ™ | 352 | 447 |
| Acridine | 362 | 462 |
| Coumarin | 432 | 472 |
| Rhodamine Green | 503 | 528 |
| FAM | 495 | 520 |
| TET | 521 | 536 |
| CALFLUOR GOLD ™ | 522 | 544 |
| JOE | 529 | 555 |
| VIC | 538 | 554 |
| HEX | 535 | 556 |
| CALFLUOR ORNG ™ | 538 | 559 |
| NED | 546 | 575 |
| TAMRA | 557 | 583 |
| Rhodamine Red | 560 | 580 |
| Cy 3.5 | 581 | 596 |
| ROX | 586 | 610 |
| CalFluor Red | 569 | 591 |
| TEXAS RED ® | 597 | 616 |
| Cy 5 | 646 | 669 |
| QUASAR ™ 670 | 647 | 667 |
| PULSAR ™ 650 | 460 | 650 |
| Cy 5.5 | 675 | 694 |
| QUASAR ™ 705 | 690 | 705 |

The particular arrangement of the optics along each optical path can be adjusted to provide for any reasonable ratio of spacing desired to suit design considerations. Suitable optics for guiding light can include at least one of the following: an optical fiber(s), a fiber optic array, or light pipes; a lens, including a condensing lens, an objected lens, a Fresnel lens, an imaging lens, a positive lens, a field lens, or a collimator lens; a reflector, such as a mirror or a beam splitter; an excitation filter, such as a dichroic filter; and an emissions filter. These optics and other useful optics are well known in the art and are commercially available. Methods of mounting such optics are also well known in the art. In certain embodiments, the flexibility of using optical fibers allows for many different arrangements of the present system. The fluorescence detection subsystem provided herein is configured for continuous or periodic monitoring and measuring of reaction-generated fluorescence during and/or after the PCR temperature cycles performed on each vessel containing an aqueous oil matrix. The position of the vessel containing the aqueous oil matrix where PCR product detection is monitored and measured by the PCR product detection subsystem is sometimes referred to herein as a "PCR product detection position."

In some embodiments, the fluorescence detection occurs at the end of the PCR temperature cycles. In a preferred embodiment, the PCR product detection occurs in real-time, wherein the fluorescence is measured after each PCR temperature cycle. In some embodiments, the fluorescence detection subsystem is configured to detect fluorescence from each individual aqueous reaction mix after each individual PCR temperature cycle, and the data collected from the PCR measurements can be analyzed and scored by automated software algorithms via a laboratory information management system (LIMS).

Many suitable configurations for the fluorescence detection subsystem are suitable for use with the present system and methods. In a preferred embodiments, the aqueous reaction mix comprises two distinct nucleic acid probes conjugated to or covalently linked to a fluorophore capable of excitation by fluorescence excitation light having a particular spectral wavelength or range of spectral wavelengths, wherein each nucleic acid probe is designed to specifically hybridize to a target nucleic acid sequence (e.g., polymorphism) of a polynucleotide sample. In such embodiments, a first nucleic acid probe comprises a first fluorophore capable of excitation by fluorescence excitation light having a first spectral wavelength, and a second nucleic acid probe comprises a second fluorophore capable of excitation by fluorescence excitation light having a second spectral wavelength. It being understood that the first spectral wavelength is a different wavelength than the second spectral wavelength such that the presence of the first nucleic acid probe can be distinguished from the presence of the second nucleic acid probe.

In particular embodiments, each optical member comprises one or more optical fibers capable of providing an optical path for fluorescence excitation light and/or fluorescence emission light between the fluorescence detection subsystem and the aqueous reaction mix volume in each of the vessels when the vessel is in the PCR product detection position. In some embodiments, each optical member comprises a bundle of optical fibers. In other embodiments, each optical member comprises a single optical fiber capable of carrying all light between each vessel and the fluorescence detection subsystem. For instance, fluorescence excitation and fluorescence emission light could be stacked over a single array of fiber optics through sequential excitation filters and emission filters (e.g., dichroic filter blocks) with diagonal optical feeds to direct the fluorescence emissions to the fluorescence emission light sensing devices.

In certain embodiments, each optical member comprises a separate fiber optic array for each fluorescence light wavelength used in the system. In such embodiments, each fiber optic array for fluorescence detection contains an individual optical fiber in optical communication with each vessel containing an aqueous oil matrix when the vessel is in the PCR product detection position, wherein each individual optical fiber comprises one end in close proximity to a vessel containing an aqueous oil matrix and the other end in an ordered tightly bundled array with a flat face presented to a fluorescence excitation light source and a fluorescence light emission sensing device. An excitation filter (e.g., dichroic filter similar to those used on epi-fluorescence microscopes) may be placed in the optical path between the array face and the fluorescence excitation light source, and an emission filter may be placed in the optical path between the array face and the fluorescence emission light sensing device. In some embodiments, a dichotic filter or filter cube comprises both the excitation filter and the emission filter and is placed in the optical path between the fiber optic array face and the fluorescence excitation light source and the fluorescence emission light sensing device (see, e.g., FIG. 8). In a particular embodiment, the fluorescence emission light sensing device is configured to collect an image at the fiber optic array face and measure the signal intensity of each individual fiber.

In another embodiment, the fluorescence detection subsystem may employ a fluorescence excitation light source that is provided by a laser (e.g., an argon-ion laser) to emit fluorescence excitation light having a spectral wavelength ranging from about 350 nm to about 1,100 nm. In this embodiment, a plurality of optical members, such as optical fibers, are used in which each optical fiber is in optical communication with the laser and inserted through a lens positioned over each vessel containing an aqueous oil matrix when in the PCR product detection position to provide an optical path for the conduction of light to and from the vessel. The fluorescence excitation light is directed through the optical fibers to excite the fluorophores in the aqueous reaction mix volume. Emissions from the aqueous reaction mix volume are sent back through the optical fibers to a fluorescence emission light sensing device. Similar fluorescence detection systems are commercially available, such as the ABI PRISM® detection systems (Applied Biosystems). In this embodiment, the laser is capable of emitting fluorescence excitation light having one or more spectral wavelengths for the detection of one or more labeled probes conjugated or covalently linked to different fluorophores having different excitation/emission wavelengths. Alternatively, separate lasers can be used, each emitting a fluorescence excitation light having a different spectral wavelength. In some embodiments, a single optical fiber corresponding to each vessel can be used to direct all fluorescence light to and from each vessel when in the PCR product detection position (i.e., excitation and emission fluorescence light is stacked over the single fiber). In such embodiments, sequential excitation light filters (e.g., dichroic filter blocks) with diagonal optical feeds can be used to direct the fluorescence emissions to the fluorescence emission light sensing devices. In other embodiments, separate optical fibers, which can be configured as an fiber optic array, are used for providing an optical path for each fluorescence excitation wavelength used for detection.

In an embodiment, the fluorescence detection subsystem may employ a plurality of LEDs or laser diodes for the emission of fluorescence excitation light. Since the footprint of an LED or laser diode is very small, multiple LEDs or laser diodes of different wavelengths could be integrated into a single package or multiple packaged LEDs/laser diodes placed very closely to excite a single vessel containing an aqueous oil matrix when in the PCR product detection position. In such an embodiment, the LEDs/laser diodes can be positioned at one or more vessel stations directly beneath the vessels when the vessels are in the PCR product detection position. Fluorescence detection systems having such a configuration are also found in the patent literature, e.g., U.S. Pat. No. 7,122,799, the content of which is incorporated herein by reference in its entirety. In other embodiments, fluorescence excitation light generated by the LEDs/laser diodes can be directed to the vessels by a plurality of optical fibers, wherein each optical fiber is inserted through a lens (e.g., collimator lens) and positioned at the top or bottom of a vessel when the vessel is in the PCR detection position.

In another embodiment, a fluorescence detection subsystem may employ a plurality of LEDs or laser diodes for the generation of fluorescence excitation light, wherein one or more fiber optic arrays for fluorescence detection provide an optical path for the excitation and emission fluorescence light. In a particular embodiment, the fluorescence detection subsystem is configured to monitor and measure fluorescence from two nucleic acid probes, each of which is covalently linked to a different fluorophore (e.g., VIC or FAM). In some embodiments, the excitation and emission fluorescence light suitable for excitation of both nucleic acid probes is stacked over a single array of fibers through sequential excitation/emission filters, e.g., dichroic filter blocks, with diagonal optical fees for the fluorescence emission light sensing devices, e.g., emission imaging sensors or CCD cameras. Alternatively, two fiber optic arrays are used, in which each fiber optic array provides an optical path for excitation and emission fluorescence light suitable for excitation of one of the nucleic acid probes (see, e.g., FIG. 8). In such an embodiment, each fiber optic array comprises a plurality of optical fibers, wherein each optical fiber is in optical communication with a vessel containing an aqueous oil matrix when the vessel is in the PCR product detection position. One end of each individual optical fiber may be positioned over the top of the vessel or the bottom of the vessel depending on the particular design and space requirements. The other end of each individual optical fiber is disposed within an ordered tightly bundled fiber optic array with a flat face in optical communication with both an fluorescence excitation light source (e.g., an LED or laser diode) and an fluorescence emission sensing device (e.g., a monochrome CCD camera). An excitation and/or emission filter, such as a dichroic filter, may be placed within the optical path and in optical communication with the fiber optic array face and the appropriate fluorescence excitation light source and/or fluorescence emission sensing device (see, e.g., FIG. 8). The fluorescence emission sensing device collects the image of the fiber optic array face and measures the intensity of the signal from each individual fiber by examining regions of interest in the image.

In some embodiments, a detection subsystem is provided that comprises both a thermal infrared imaging device and the fluorescence detection subsystem. Such an arrangement by utilize a single optical fiber for carrying all light, i.e., blackbody infrared radiation and fluorescence excitation and emission light between all detectors (i.e., the thermal infrared sensing device and the one or more fluorescence emission light detectors) and a vessel containing an aqueous oil matrix. In other embodiments, separate fiber optic arrays are used for thermal detection and each fluorescence excitation light wavelength.

In certain aspects of the present disclosure, a fluorescence measurement is taken from each vessel containing an aqueous oil matrix when that vessel is in a PCR product detection position. In some embodiments, the PCR product detection position is the same locations, e.g., same vessel stations, as the heating position and the temperature monitoring position. In some embodiments, the electromagnetic radiation sources and the thermal detection devices can be positioned at and/or in optical communication with the top of the vessels containing the aqueous oil matrices. Depicted in FIG. 2 is an embodiment of the present system where an electromagnetic radiation source 201 (e.g., laser diode or LED) and a detector 202 are positioned at and/or in optical communication with the top of vessel 101. In an embodiment, detector 202 is a combination of the thermal infrared sensing device and the fluorescence detection subsystem. Electromagnetic radiation is emitted from the electromagnetic radiation source 201 to the aqueous reaction mix volume 104 (dotted line) positioned within an aqueous oil matrix comprising an encapsulation oil 103 and a carrier oil 102. In this embodiment, electromagnetic radiation, such as infrared radiation, is carried along an optical path by an optical fiber or light pipe 203 and focused on the aqueous reaction mix volume 104 via a collimator lens 204. As the temperature rises, aqueous reaction mix volume 104 emits black body infrared radiation (dotted line) that is carrier to the thermal infrared sensing device of detector 202 by an optical fiber(s) 205. After the heating and temperature monitoring steps are complete, both the electromagnetic radiation source 201 and the thermal infrared sensing device of detector 202 are shut off to allow for fluorescence detection. Fluorescence excitation light is carried from the fluorescence detection subsystem of detector 202 along optical fiber(s) 205 and is focused by lens 204 on the aqueous reaction mix volume 104. Upon absorption of the fluorescence light having the appropriate wavelength, a fluorophore covalently linked to a nucleic acid probe emits fluorescence that is collected and conducted by optical fiber(s) 205 to a fluorescence emission light sensing device of detector 202. In some embodiments, fluorescence excitation light having two different wavelengths is carried between the fluorescence detection subsystem and the aqueous reaction volume 104 by a single optical fiber 205. In other embodiments, fluorescence excitation light having two different wavelengths is carried between the fluorescence detection subsystem and the aqueous reaction volume 104 via a bundle of optical fibers and/or one or two optical fiber array(s).

In other embodiments, the PCR product detection position is at a different location, e.g., vessel station, than the heating position. Shown in FIG. 5 is a configuration where an electromagnetic radiation source 501 is positioned at the top of vessel 101 when in the heating position. Following the heating step, the vessel 101 is moved by the positioning device to the next vessel station where detector 502 is positioned at the top of the vessel 101 when in the PCR detection position. Fluorescence excitation light is carried from the fluorescence detection subsystem of detector 502 along optical fiber(s) 505 and is focused by lens 506 on the aqueous reaction mix volume 104. Upon absorption of the fluorescence light having the appropriate wavelength, a fluorophore covalently linked to a nucleic acid probe emits fluorescence (dotted line) that is collected and conducted by optical fiber(s) 505 to a fluorescence emission light sensing device of detector 502. In some embodiments, fluorescence excitation light having two different wavelengths is carried between the fluorescence detection subsystem and the aqueous reaction volume 104 by a single optical fiber 505. In other embodiments, fluorescence excitation light having two different wavelengths is carried between the fluorescence detection subsystem and the aqueous reaction volume 104 via a bundle of optical fibers and/or one or two optical fiber array(s).

Embodiments Comprising Integrated Subsystems with a Moving Belt Configuration

In some embodiments, the present systems and methods comprise a combination of subsystems for providing reaction-by-reaction, light-driven photonic heating; reaction-by-reaction temperature monitoring; and fluorescence detection of PCR products for PCR amplification and product detection. In some aspects, the present systems and methods additionally comprise a positioning device configured to move a collection of aqueous oil matrices in discrete steps through a plurality of vessels stations, wherein the vessel stations may include one or more of the subsystems. In a preferred embodiment, the positioning device comprises a flexible belt, such as belt 402 depicted in FIGS. 4A and 4B. In this embodiment, the belt 402 comprises a flexible material (e.g., a thermoplastic polymer) forming a loop structure around two or more drive gears 401, and wherein a plurality of vessels 404 are embedded in the belt 402. Drive gears 401 rotate and cause the belt 402 to move the vessels 404 from vessel station to vessel station. The mechanical, electronic, and software systems that control the movement of the drive gear are described in detail elsewhere herein.

Figure 6A:
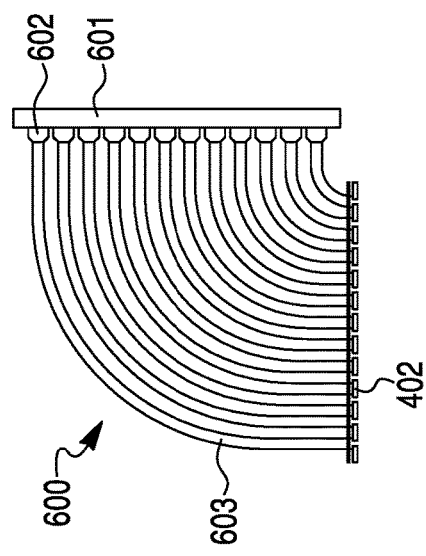
FIG. 6A depicts a front view of an exemplary photonic heating subsystem.
Figure 6B:
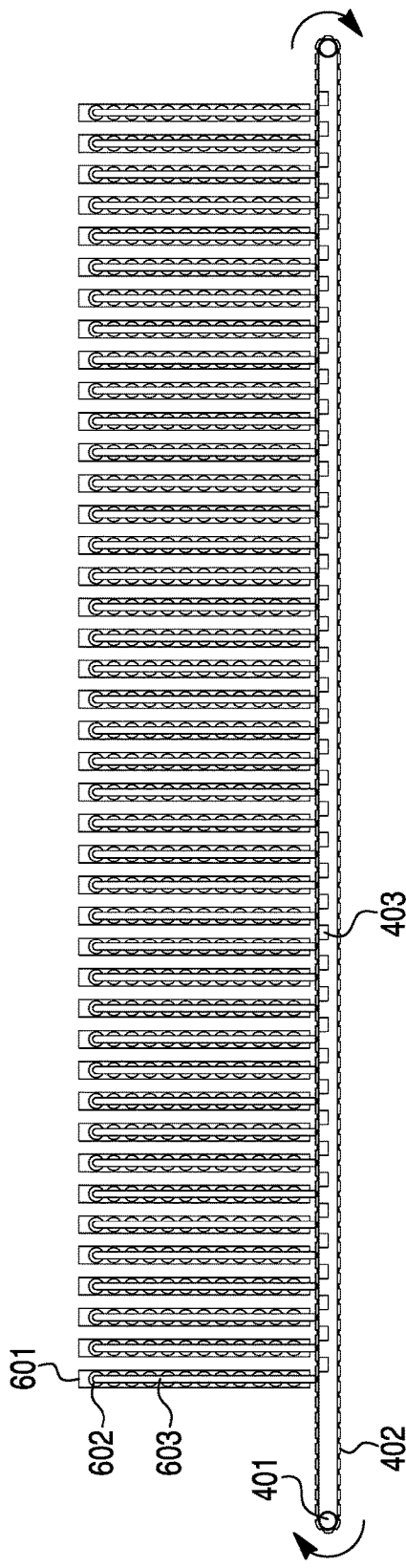
FIG. 6B depicts a side view of an exemplary photonic heating subsystem.
Figure 6C:
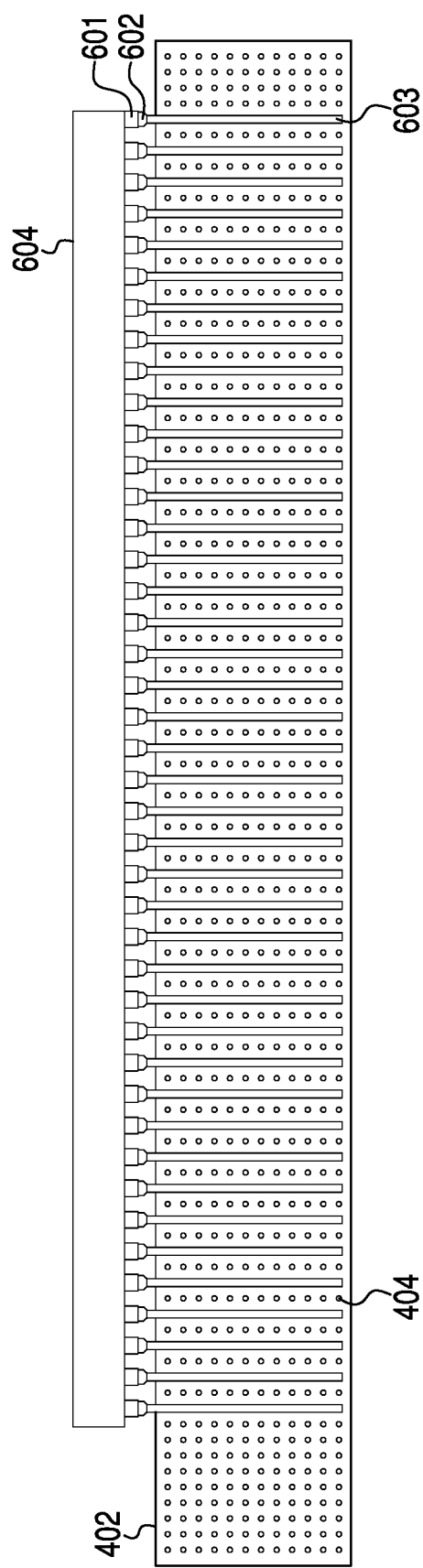
FIG. 6C depicts a top view of an exemplary photonic heating subsystem.

Depicted in FIGS. 6A-6C is one embodiment of a photonic heating subsystem 600 comprising a plurality of electromagnetic radiation sources 602 and a belt 402 as a positioning device for moving the vessels 404 from vessel station to vessel station. The number of electromagnetic radiation sources 602 can vary depending on spacing and design parameters. In addition, the size of the electromagnetic radiation sources and the associated circuitry and/or cabling will determining the particular spatial configuration. While not intending to be limiting, the photonic heating subsystem 600 includes 504 independent electromagnetic radiation sources 602 and a belt 402 wherein the vessels 404 are arranged in rows of 12 vessels per row at 9 mm spacing to fit with international standards for well spacing.

To reduce the footprint of the photonic heating subsystem 600, the electromagnetic radiation sources 602 are stacked vertically on 42 modules 601 positioned to a side of belt 402, with 12 electromagnetic radiation 602 sources in each vertical stack (see FIGS. 6A and 6B). To provide photonic heat directly to each vessel 404 containing an aqueous oil matrix, photonic heating subsystem 600 is further configured such that the arrangement of the electromagnetic radiation sources 602 correspond with the configuration of the vessels 404 on belt 402. As such, each electromagnetic radiation source 602 is in optical communication with an optical fiber or light pipe 602, with each optical fiber or light pipe 603 providing an optical path for guiding the emitted electromagnetic radiation to a corresponding vessel 404 when that vessel is in the heating position. This configuration facilitates easy connections to circuitry and other cabling.

The end of each optical fiber or light pipe 603 that is proximal to the corresponding vessel 404 terminates in a lens configured to focus the beam of electromagnetic radiation on the aqueous reaction mix volume or plasmonic excitable material depending on the particular wavelength of the electromagnetic radiation being used. For instance, when using infrared radiation, the beam is focused on the aqueous reaction mix volume and absorbed by the water molecules to heat the aqueous reaction mix. Alternatively, if visible light, such as blue light, violet light, or ultraviolet light is used, the beam is focused on a plasmonic excitable material, such as a gold layered Mylar or aluminum foil disk, to convert the light energy to heat energy. With this configuration, there are 42 stacks of electromagnetic radiation sources 602 to provide 42 PCR temperature cycle heating positions or, alternatively, two "hot start" heating positions followed by 40 PCR temperature cycle heating positions. As shown in FIG. 6B, each module 601 is positioned adjacent to every other row of vessels 404 to accommodate a cooling and fluorescence detection position between each PCR temperature cycle. The vessels 404 are cooled by an active or passive cooling member 403, such as a passive heat sink metal, positioned under the top side of the loop of belt 402.

In some embodiments, each electromagnetic radiation source 602 operates at a fixed and constant wattage output, wherein each electromagnetic radiation source 602 can be activated for a specific period of time, under computer programmable control, to provide the desired amount of energy needed to heat each aqueous reaction mix through a PCR temperature cycle. In other embodiments, the wattage output of the electromagnetic radiation sources 602 can be varied.

FIG. 6A depicts a front view of the photonic heating subsystem 600 and belt 402, wherein the electromagnetic radiation sources 602 are stacked vertically on module 601, with 12 electromagnetic radiation sources 602 in each vertical stack. Each optical fiber and light pipe 603 extend from the corresponding electromagnetic radiation source 602 to the top of the corresponding vessel 404 of belt 402.

FIG. 6C depicts a top view of the photonic heating subsystem 600 and belt 402. Each electromagnetic radiation source 602 is electronically connected to electronics bay 604.

In some embodiments, vessels 404 are coated with a plasmonic excitable material such as gold to maximize conversion of light (e.g., ultraviolet, violet, or blue light) to heat. In other embodiments, a gold layered Mylar or aluminum foil disk is disposed within each vessel 404 to maximize conversion of light (e.g., ultraviolet, violet, or blue light) to heat.

It is an aspect of this disclosure to provide real-time quantitative PCR data by measuring fluorescence following each PCR temperature cycle. FIG. 7 depicts a side view illustrating an embodiment of the PCR amplification and product detection system. In this configuration, fiber optic arrays 701 translate light between the vessels of the belt 402 and a set of light detectors 708, which include fluorescence emission light detectors and a thermal infrared sensing device. The use of fiber optic arrays 701 allows optical communication between the detectors and vessels spread out over a wide area. For instance, the use of fiber optic arrays 701 provide for the translation of light between vessels spread over a 100 mm by 900 mm area and a small ordered set of fiber end faces occupying an area of only 10 mm by 15 mm, or smaller. Fiber optic arrays are commercially available and are often used to condense optical signals from microtiter plate wells for efficient imaging by CCD cameras, such as described in FiberGuide Industries, "White Paper: 2D Arrays" (available on the FiberGuide Industries website), the content of which is incorporated by reference herein in its entirety.

As illustrated in the exemplary embodiment of FIG. 7, there are 42 stacks of electromagnetic radiation sources 602 to provide two "hot start" heating positions (indicated by "D") followed by 40 PCR temperature cycle heating positions. As shown in FIG. 7, each module 601 is positioned adjacent to every other row of vessels on the belt 402 to accommodate a temperature monitoring position and/or a cooling and fluorescence detection position between each PCR temperature cycle. The vessels are cooled by an active or passive cooling member 403, such as a passive heat sink metal, positioned under the top side of the loop of the belt 402. As illustrated in FIG. 7, the fiber optic arrays 701 provide an optical path to the light detectors 708 from each vessel of the belt 402 when that vessel is in the PCR product detection position and the temperature monitoring position. In this embodiment, the lights detectors 708 include two CCD cameras 706, 710 as the fluorescence emission light detectors and a thermal imager 704 as the thermal infrared sensing device. For illustrative purposes only, included are two fluorescence excitation light sources 705, 707 of different spectral wavelengths.

The fiber optic arrays 701 include three separate fiber optic arrays 714, 715, 716, each in a tightly ordered bundle at one end connected to fiber optic array plates 713, 712, 709, respectively. Two of the fiber optic arrays 715, 716 conduct fluorescence excitation/emission light for fluorescence detection, while the third fiber optic array 714 conducts black body infrared radiation for temperature monitoring. Further, each fiber optic array 715, 716 for fluorescence detection in this exemplary embodiment comprises 480 individual optical fibers with one end of each fiber positioned over a vessel when that vessel is in the PCR product detection position. The fiber optic array 714 for temperature monitoring in this exemplary embodiment comprises 504 individual optical fibers with one end of each optical fiber positioned over a vessel when that vessel is a temperature monitoring position. The first temperature monitoring position provides a baseline temperature reading of a row of vessels (indicated as "I") before the heating process begins. The next two temperature monitoring positions provide temperature readings during the hot start process. The remaining temperature monitoring positions are at the same vessel stations as the passive heat sink metals 403 and the PCR detection positions.

For fluorescence detection, the excitation light source 707 emits fluorescence excitation light through a dichroic filter cube 702 to a fiber optic array plate 709 optically connected to an ordered tightly bundled array configured to provide an optical path along the fiber optic array 716 to each vessel when that vessel is in the PCR product detection position. Further, fluorescence emission light from the aqueous reaction mix volume is conducted from the vessel along the fiber optic array 716 to the fiber optic array plate 709. The fiber optic array plate 709 produces an image array on its face by condensing the optical signals of the fluorescence emission light, and the CCD camera 706 collects the image and measures the intensity of the signal of each individual fiber in the image. In addition, the excitation light source 705 emits fluorescence excitation light through a dichroic filter cube 711 to a fiber optic array plate 712 optically connected to an ordered tightly bundled array configured to provide an optical path along the fiber optic array 715 to each vessel when that vessel is in the PCR product detection position. Further, fluorescence emission light from the aqueous reaction mix volume is conducted from the vessel along the fiber optic array 715 to the fiber optic array plate 712. The fiber optic array plate 712 produces an image array on its face by condensing the optical signals of the fluorescence emission light, and the CCD camera 710 collects the image and measures the intensity of the signal of each individual fiber in the image.

For temperature monitoring, black body infrared radiation emitted from each aqueous oil matrix at the initiation stage "I", following each "hot start" "D", and during each PCR product detection step is conducted along the fiber optic array 714 to a fiber optic plate 713. The infrared image on the face of the fiber optic plate 713 is measured by the thermal imager 704, which measures the intensity of the signal for each vessel and converts the intensity to temperature. In some embodiments, an infrared radiation filter 703 is placed between the face of the fiber optic plate 713 and the thermal imager 704.

Figure 8:
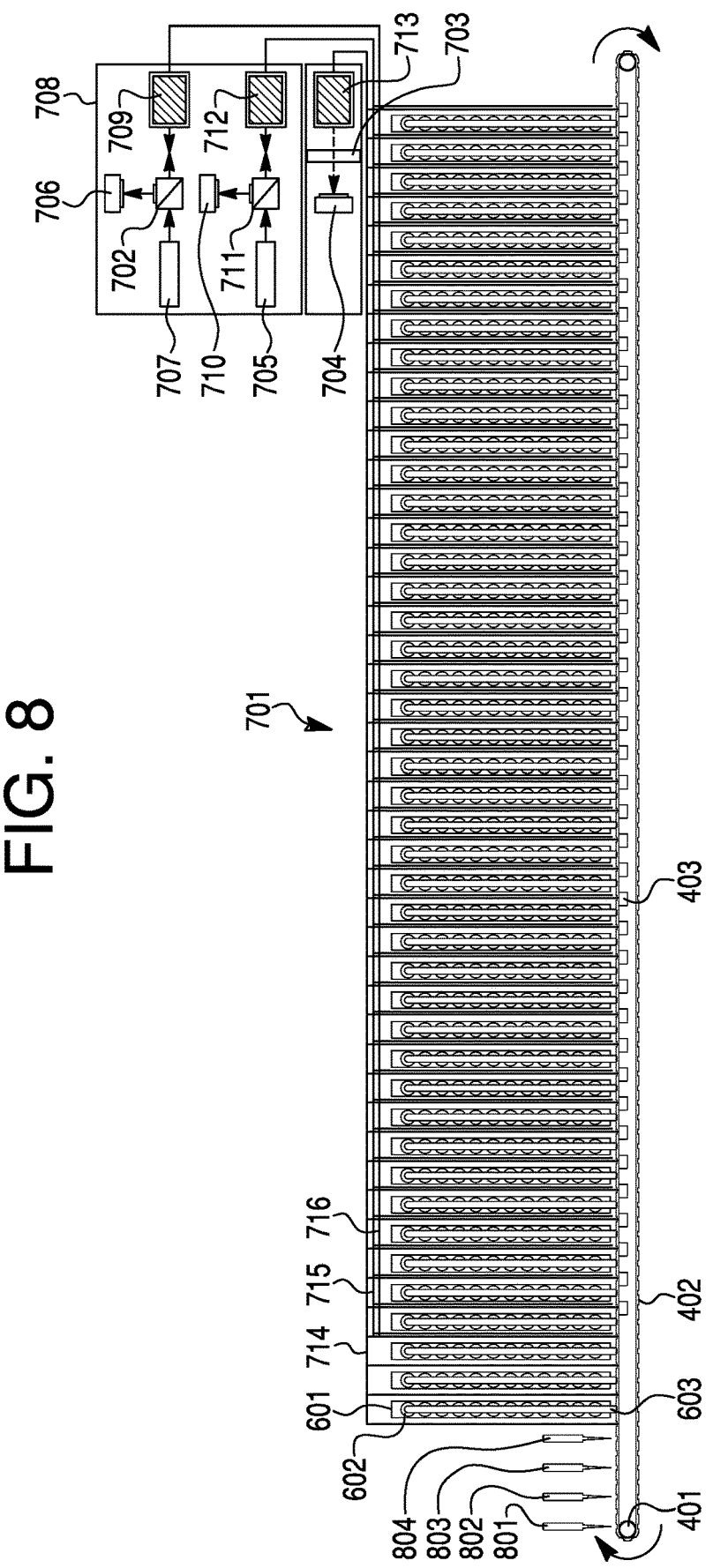
FIG. 8 depicts a side view of an embodiment of the PCR amplification and product detection system.

In another embodiment, the PCR amplification and product detection system additionally comprises an assembly subsystem configured for programmable and automated assembly of collections of aqueous oil matrices. Depicted in FIG. 8 is a side view of an embodiment of the PCR amplification and product detection system. In this embodiment, an assembly subsystem is provided that comprises liquid discharge members 801, 802, 803, 804. In some embodiments, the liquid discharge member 801 is a 12-tip bulk dispenser configured for dispensing carrier oil, the liquid discharge member 802 is a 12-tip bulk dispenser configured for dispensing encapsulation oil, the liquid discharge member 803 is an automated pipettor (e.g., a fixed pipetting head with 12 tips) configured for dispensing an aqueous volume comprising polynucleotide samples, and the liquid discharge member 804 is an automated pipettor (e.g., a single tip, non-contact pipetting head) configured for dispensing an aqueous volume comprising PCR reagents, primers, and/or probes.

Figure 9:
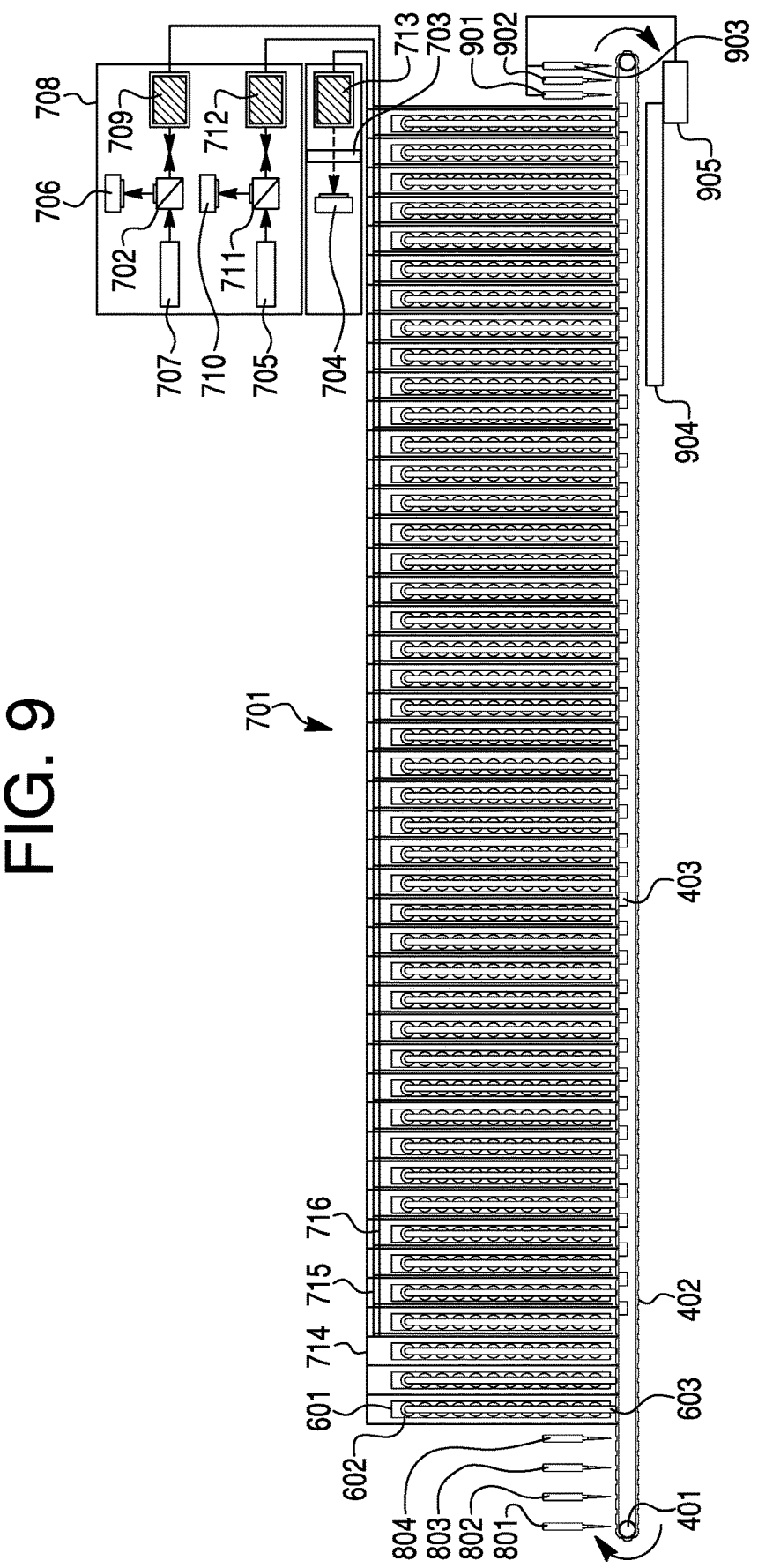
FIG. 9 depicts a side view of an embodiment of the PCR amplification and product detection system.

Depicted in FIG. 9 is a side view of an embodiment of the PCR amplification and product detection system. In the assembly subsystem of FIG. 9, a system control causes the belt 402 to move a row of 12 vessels into an assembly position. Based on the signals from each operational module and the time needed to complete the slowest PCR heating step on the belt 402, the belt 402 advances one step (9 mm) when all operations occurring simultaneous at all vessel stations on belt 402 are complete. For instance, in an embodiment, the PCR temperature cycle with the longest duration is approximately 15 seconds. Therefore, the processes occurring have no more than approximately 15 seconds to complete each process before the belt is programmed to move to the next step. At the first assembly position, a 12-tip bulk pipettor 801 aspirates carrier oil from a carrier oil input and dispenses the carrier oil into the row of vessels. The belt 402 moves the row of vessels to the next assembly position where a 12-tip bulk pipettor 802 aspirates encapsulation oil from an encapsulation oil input and dispenses the encapsulation oil into the row of vessels. The belt 402 moves the row of vessels to the next assembly position, where fixed pipetting heads 803 aspirate an aqueous volume that contains the appropriate polynucleotide sample from, e.g., an input plate comprising a bar code. The assembly station may comprise a bar code reader configured to read the bar code and access, e.g., LIMS software to identify the polynucleotide sample and to determine the appropriate primers and probes for use with each particular polynucleotide sample. The control system then causes the fixed pipetting heads 803 to dispense the polynucleotide sample into as many vessels as needed to accommodate the number of primer/probe reactions to be run. In some cases, the number of runs will require multiple rows of vessels. The fixed pipetting heads 803 have approximately 15 seconds, or less, depending on the timing of the PCR temperature cycles to perform the dispensing step for each row. Furthermore, the fixed pipetting heads 803 may be configured for either automated or manual tip changes to prevent contamination or, alternatively, the fixed pipetting heads 803 may be configured for either automated tip washing.

The belt 402 then moves the row of vessels to the final assembly position, where a single, tip, non-contacting pipetting head 804 aspirates an aqueous volume containing the appropriate PCR reaction mix, primers, and probes in an amount sufficient for all of the polynucleotide samples to be tested with that particular PCR reaction mix, primers, and probes. The assembly substation then causes the single, tip, non-contacting pipetting head 804 to dispense the PCR reaction mix, primers, and probes into the row of vessels containing the appropriate polynucleotide sample. The information necessary to identify the appropriate PCR reaction mix, primers, and probes for a particular PCR genotyping reaction can be provided from a LIMS. In such case, loaded lists of simple queries could provide the assembly software program with the needed information from the LIMS. Similar hardware and software configurations suitable for use with the present system are known in the art. As with all other processes occurring at a given vessel station, the PCR reaction mix, primers, probes dispensing step has approximately 15 seconds to be completed.

After assembly of the reactions in the row of vessels, the belt 402 moves the row to the next vessel station where, optionally, an initial temperature measurement "I" can be taken to provide this information to the system control software for determining the amount of output energy required for hot start denaturation of the polynucleotide samples in each aqueous reaction mix. At this vessel position, an optical fiber from the fiber optic array 714 is positioned above each well and conducts black body infrared radiation emitted by each aqueous oil matrix at this vessel station to the fiber optic array plate 713, which condenses the optical signals for imaging by the thermal imager 704. The thermal imager 704 converts the signal intensity to temperature information that is used by the control system software to adjust the pulse duration of the electromagnetic radiation sources 602 when the vessels are moved forward to the first hot start heating position "D". In this embodiment, two hot start positions are each followed by a temperature monitoring position. The control system software causes the belt 402 to move the row of vessels to the next vessel station, which is the first hot start heating position "D". In this embodiment, each electromagnetic radiation source 602 is a laser diode emitting infrared radiation. As such, laser diodes 602 emit infrared radiation through light pipes 603, wherein the end of each light pipe 603 is positioned at the top of each vessel in the row to apply infrared radiation to the aqueous reaction mix volume contained therein. Preferably, the temperature of each aqueous reaction mix volume is raised to about 90° C. to about 99° C., most preferably to about 95° C., to denature the polynucleotide samples in each aqueous reaction mix volume. After the first hot start heating step, the control software causes the belt to move the row of vessels to the next vessel station, which is a temperature monitoring position. An additional hot start heating position "D" is included in case the needed hot start denaturation requires more than 15 seconds.

After the second hot start heating step, the belt 404 moves the row of vessels to the next vessel station, which is a cooling position and a temperature monitoring position. The cooling position comprises passive heat sink metal 403 positioned proximately underneath the top side of belt 404 as shown in FIG. 9. As the passive heat sink metal blocks 403 come into contact with the bottom of the vessels, heat is transferred from the aqueous oil matrix through the vessels and into the heat sink metal blocks 403 to cool the aqueous oil matrices in the row. Preferably, the temperature of the aqueous oil matrices is decreased to about 60° C. At this vessel station, the temperature of each aqueous oil matrix is measured via the thermal imager 704.

Next, the control system causes the belt 402 to move the row of vessels to the next vessel station to begin PCR temperature cycling. The laser diodes 602 emit infrared radiation to the aqueous reaction mix volume in each vessel in the row, thereby raising the temperature of the aqueous reaction mix volume. Additionally, the control system software enables marker specific PCR conditions by causing the laser diodes to emit appropriate infrared radiation energy and pulse duration to raise the temperature of the aqueous reaction mix volume to the appropriate annealing temperature and elongation temperature. After the heating step is complete, the control system causes the belt 402 to move the row of vessels into the cooling position, PCR product detection position, and temperature monitoring position at the next vessel station. In the cooling position, heat is transferred from each aqueous oil matrix in the row to the passive metal heat sink 403, thereby lowering the temperature of the aqueous oil matrix. Fluorescence excitation light having spectral wavelengths suitable for excitation of the fluorophores present in the PCR reaction mix (e.g., VIC and FAM) are emitted from fluorescence excitation light sources 705, 707 through the fiber optic arrays 715, 716 and to the aqueous reaction mix of each vessel in the row. Fluorescence emission light from the vessels is conducted back through the fiber optic arrays 715, 716 to the CCD cameras 710, 706, which convert the optical signal intensity to raw fluorescence signals for processing by the control system software. At this vessel position, an optical fiber from the fiber optic array 714 is positioned above each well and conducts black body infrared radiation emitted by each aqueous oil matrix at this vessel station to the fiber optic array plate 713, which condenses the optical signals for imaging by the thermal imager 704. The thermal imager 704 converts the signal intensity to temperature information that is used by the control system software to adjust the pulse duration of the electromagnetic radiation sources when the vessels are moved forward to the heating position. This process is repeated up to 40 or more PCR temperature cycles.

In some embodiments, the dichroic filter cubes 706, 711 and the infrared emission filter 703 enable the temperature measurements and the fluorescence measurements to occur simultaneously by preventing crosstalk by the different spectral wavelengths. In other embodiments, the temperature measurements and the fluorescence measurements are performed sequentially within the available timeframe. Temperature monitoring after the heating step is useful for providing the control system software with temperature information necessary to determine the appropriate energy output required for the next heating step. In some embodiments comprising a temperature monitoring step after the photonic heating step, dynamic temperature feedback during the heating steps is not possible due to rapid heat dissipation. For instance, in some embodiments, the aqueous reaction mix volumes dissipate heat rapidly and exhibit a decrease in temperature by about 20° C. per second when the heating source is removed. Therefore, in some embodiments, the heating positions comprise insulation to decrease heat loss. In other embodiments, temperature monitoring at the PCR product detection position is used by the control system software to normalize the raw fluorescence data, because it is known in the art that fluorescence light having certain spectral wavelengths can be affected by temperature. However, embodiments comprising a cooling mechanism at the PCR product detection position lower the temperature of the aqueous reaction mix to allow all fluorescence measurements to be taken at approximately the same temperature.

Alternatively, dynamic temperature feedback during the photonic heating steps can be accomplished by placing the laser diodes and the thermal detectors at the same position. However, as discussed above, thermal imaging cannot be performed simultaneously with the heating if the electromagnetic radiation sources emit significant infrared radiation in the same infrared band used to heat the aqueous reaction mix volumes unless a "flickering" process is used (i.e., rapidly alternating flashing of the infrared heating source with detection sensing of black-body infrared emission). In some embodiments, a thermocouple or a thermistor is used in place of thermal imaging, which enables temperature monitoring to be performed simultaneously with infrared irradiation enabling dynamic temperature feedback during the photonic heating.

Also depicted in FIG. 9 is a waste dispose subsystem comprising aspirators 901, 903, a bulk dispenser 902, an oil separator 905, and a ultraviolet lamp 904. After the aqueous oil matrices have moved through all of the heating positions, temperature monitoring positions, and PCR product detection positions, the aqueous oil matrices may be removed from the vessels and discarded. The control system causes the belt 402 to move the row of vessels from the vessel station comprising the final PCR product detection position to the aspirator 901. In a preferred embodiment, the aspirator 901 is a 12-position pipetting head. The aspirator 901 aspirates the entire aqueous oil matrix from each vessel in the row and passes the aqueous oil matrix to waste. In some embodiments, the aqueous oil matrix is passed through a tubing system that would eliminate the need to move the aspirators 901 to the waste location. The control system then causes the belt 402 to move the row of vessels to the bulk dispenser 902, which dispenses clean oil or water into each vessel of the row. Next, the control system causes the belt 402 to move the row of vessels to the aspirators 903, which aspirate the oil or water from each vessel in the row. As shown in FIG. 9, an embodiment may comprise an oil separator 905 in which the carrier and encapsulation oil are drawn off and reused in the assembly subsystem. After the second aspiration, the control system causes belt 402 to move the wells to the underside of the belt loop, wherein an ultraviolet lamp 904 emits ultraviolet radiation to destroy any remaining polynucleotides in the vessels to prevent polynucleotide contamination of subsequent PCR reactions.

Figure 10:
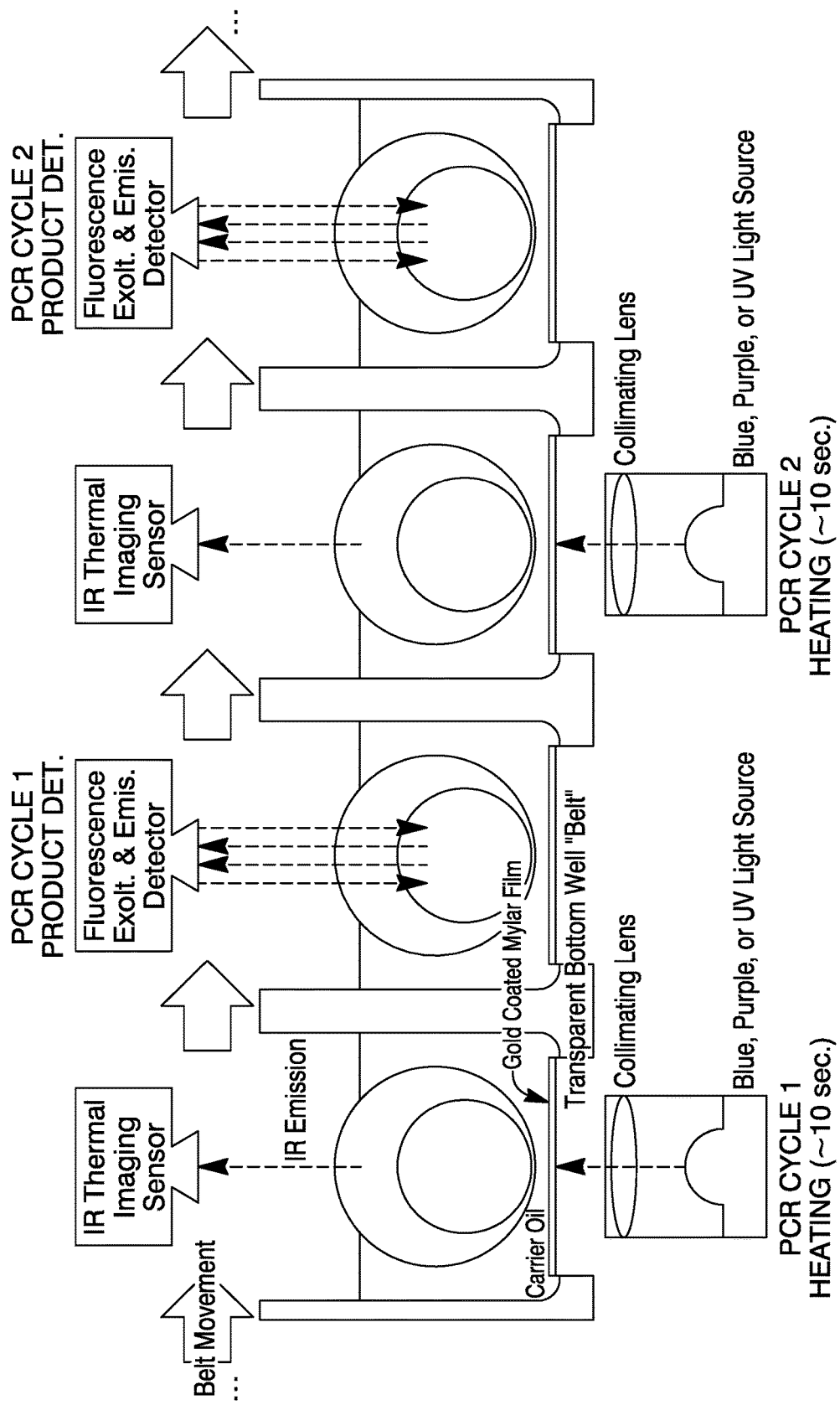
FIG. 10 depicts a side view of an embodiment of the PCR amplification and product detection system.

Depicted in FIG. 10 is a preferred arrangement of the photonic heating position, temperature monitoring position, and PCR product detection position of the PCR amplification and product detection system. In this embodiment, the belt, the assembly subsystem, and the waste disposal subsystem are arranged as shown in FIG. 9. In the embodiment shown in FIG. 10, however, the system comprises heating positions and temperature monitoring positions at the same vessel stations in an alternating configuration with vessel stations comprising the PCR product detection positions (and cooling positions). The belt moves a row of vessels into a heating position, wherein the electromagnetic radiation sources are positioned beneath the vessels. In this embodiment, the electromagnetic radiation sources, e.g., LEDs, are positioned at the bottom of each vessel when the vessel is in a heating position, wherein the LEDs emit electromagnetic radiation having a spectral wavelength in the range from about 100 nm to about 500 nm (i.e., ultraviolet, violet, and blue light wavelengths) (see, e.g., FIG. 3). In a preferred embodiment, LEDs emit blue light. The electromagnetic radiation is focused via a collimating lens on a gold-coated Mylar film disposed between the bottom of the vessel and the encapsulation oil. The light energy is converted to heat energy (as described elsewhere herein) and raises the temperature of the aqueous reaction mix volume. In this embodiment, simultaneous temperature monitoring is performed via a thermal imaging sensor in optical communication with the aqueous oil matrix. In a preferred embodiment, an optical fiber is positioned at the top of each vessels when that vessel is in a temperature monitoring position and conducts black-body infrared radiation emitted from the aqueous oil matrix to the thermal imaging sensor (see, e.g., FIG. 3). In some embodiments, an infrared emission filter is placed in the optical path of the black-body infrared radiation and positioned between the thermal imaging sensor and a flat face of a fiber optic plate (see, e.g., FIG. 9). In this embodiment, each PCR temperature cycle is completed in about ten seconds or less.

After the first PCR temperature cycle is complete, the control system causes the belt to move the row of vessels to the next vessel station, which comprises a PCR product detection position. As illustrated in FIG. 10, fluorescence excitation light having two different spectral wavelengths is generated by the fluorescence excitation light sources of the fluorescence excitation and emission detector and carried, e.g., by one or more optical fibers positioned above each vessel when that vessel is in the PCR product detection position, and transmitted to the aqueous reaction mix volume (shown by dotted arrows). In response thereto, fluorophores in the aqueous reaction mix volume emit fluorescence emission light that is carried back to the fluorescence excitation and emission detector by, e.g., the one or more optical fibers (shown by dotted arrows). The intensity of the fluorescence emission light is then measured by the fluorescence emission light detector (e.g., CCD camera) of the fluorescence excitation and emission detector. In some embodiments, the optical path of each fluorescence excitation light comprises a fluorescence excitation light source, a dichroic filter cube, a fiber optic array plate, a CCD camera, and a fiber optic array (see, e.g., FIG. 9). In some embodiments, the optical path of each fluorescence excitation light is comprised of only a light source (LED or laser) and the fluorescence emission detection is comprised only of an emission filter and a CCD or CMOS camera. Additionally, a passive heat sink may be disposed under the top side of the belt and positioned beneath each vessel when in the PCR detection position (see, e.g., FIG. 9). After the PCR product detection step is completed, the control system causes the belt to move the row of vessels to the next vessel station where the process is repeated for a predetermined number of PCR temperature cycles ranging from 1 to 40.

Mechanical, Electronics, and Software Control Systems

Figure 11:
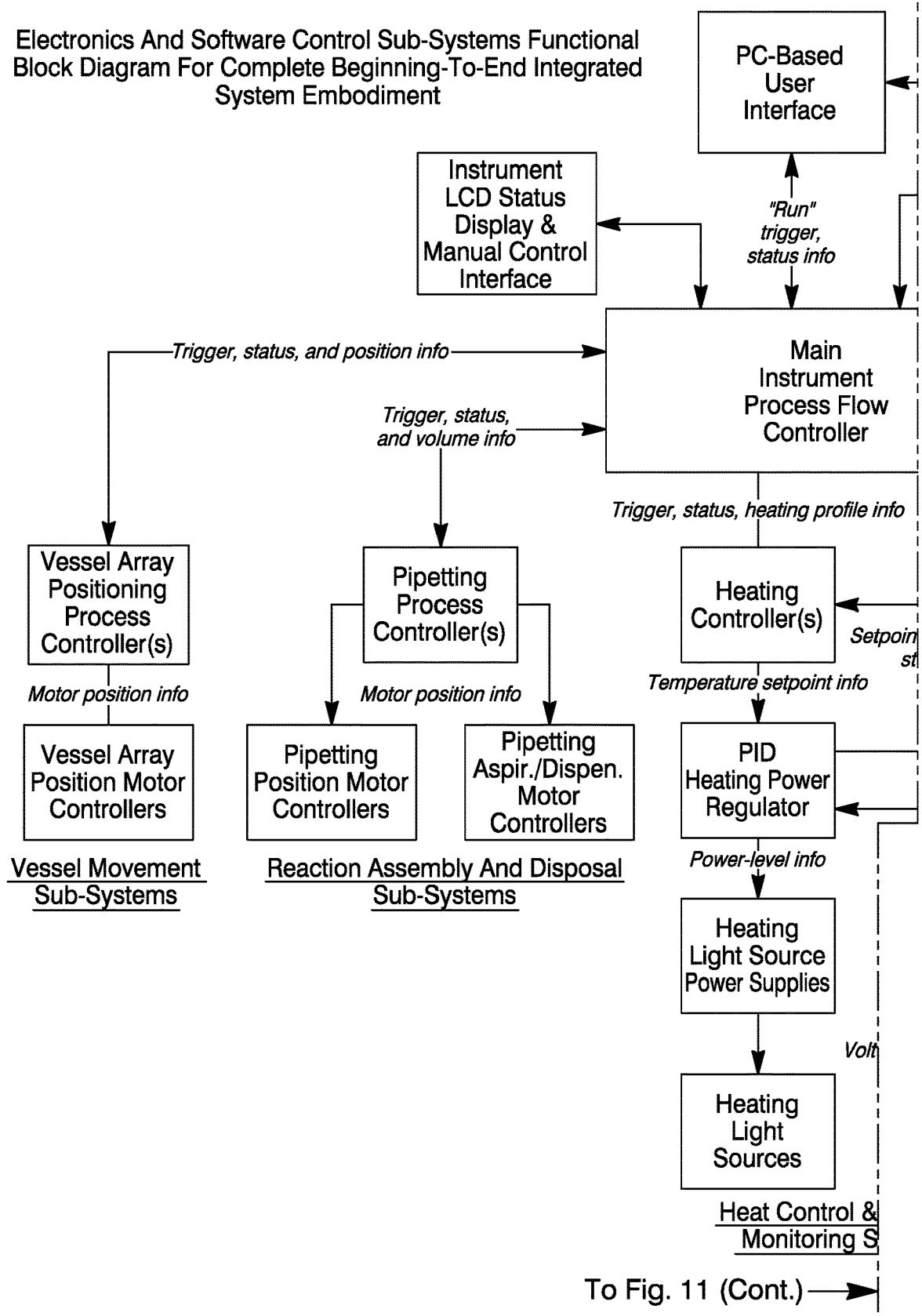
FIG. 11 depicts a block diagram of the mechanical, electronics, and software control system.
Figure 11:
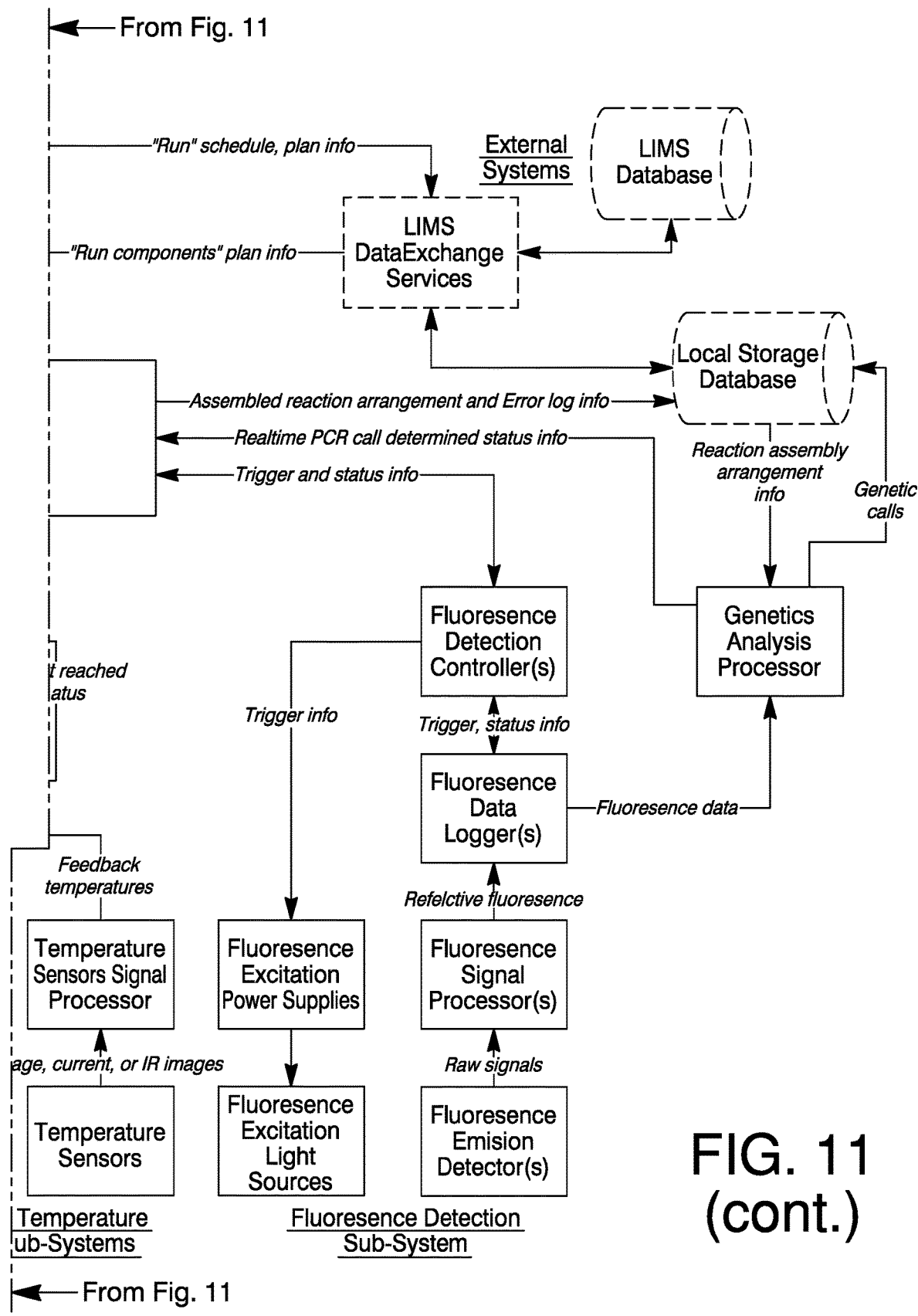

Provided herein are mechanical systems, electronic systems, and software functionality suitable for control of the PCR amplification and product detection system. A wide variety of possible electronic and software configurations are suitable for use in providing a mechanical and electronic control system capable of being incorporated into the present system and are well within the purview of the skilled artisan. Depicted in FIG. 11 is a functional block diagram of a preferred embodiment comprising control functions for a complete beginning-to-end single device embodiment (such as the moving belt embodiments shown in FIGS. 9 and 10). In some embodiments, the present system comprises assembling the reactions in well-plates off-line and/or manually moving an array of vessels to a device configured such that PCR heating and fluorescence detection is accomplished without moving the vessels (i.e., without the need for a moving belt or other automated positioning device). Such embodiments are made possible by co-locating heating and fluorescence detection components on common light paths associated with each vessel. In such a case, reaction assembly and/or vessel positioning is not needed. Heating and detection operations on the device would occur sequentially, rather than simultaneously at separate locations. By performing PCR cycle heating followed, sequentially, by fluorescence detection, complications imposed by possible interference of fluorescence detection by the heating light source and the rapidly changing temperatures are eliminated. However, continuous loading, processing, and unloading is not possible and throughput is more limited.

Depicted in FIG. 11 is a functional block diagram of a preferred embodiment comprising control functions for a complete beginning-to-end single device embodiment. As shown in FIG. 11, the system comprises a Main Instrument Process Flow Controller (PLC or electronic microcontroller) which is programmed to provide functions to initiate and control each action involved in the process flow of a "run" occurring on the instrument. A "run" is defined herein as operations on a set of reactions assembled, processed, and monitored for PCR product fluorescence where the PCR amplification and product detection system runs autonomously without any significant instructional input during the process flow and the PCR amplification and product detection system is not shutdown or reset during the process flow for any bulk loading, unloading, or maintenance operations. As such, all reaction assembly and PCR parameter information needed by the system to support a run is pre-defined and communicated to the system before the run begins. An embodiment that uses such a control system is the microtiter plate-based system. Alternatively, information needed to begin assembly and processing of available samples and reactions is communicated to PCR amplification and product detection system to begin operations, and additional information is subsequently communicated to the PCR amplification and product detection system to augment its instructions and support continued assembly and processing of additional samples that are provided such that the system instrumentation does not completely stop at any time during the run and a process flow is maintained.

Under the control of the Main Instrument Process Flow Controller, individual sub-systems can have their own electronic microcontrollers or may be controlled by sub-routines, multiple processors, and electronic modules of the Main Instrument Process Flow Controller. In either case, the subsystems perform their individual functions in cooperation and coordination such that timing of operations assures proper assembly and processing of all reactions. For instance, the exact time required to perform a particular PCR thermocycling heating and cooling operation for any given reaction assembly volume is not known in advance and is determined, dynamically, through feedback temperature monitoring of the particular reaction assembly volume during the heating process. Therefore, the Main Instrument Process Flow Controller collects and compiles feedback signal status information for every vessel undergoing processing and prevents the next processing step from occurring for any vessels until the previous step is completed for all vessels. Fluorescence detection is not initiated until thermocycling heating is completed. Likewise, on a belt system, wells are not advanced down the belt by the Vessel Array Position Motor Controllers until it is confirmed by the Main Instrument Process Flow Controller that reaction assembly is complete and/or fluorescence detection readings are complete for all wells. Once the reaction assembly, photonic heating, and/or fluorescence detection readings are completed for all wells, the Main Instrument Process Flow Controller informs the Vessel Array Positioning Process Controllers to relay motor positioning information to the Vessel Array Position Motor Controllers to cause the positioning device (e.g., moving belt) to move the vessels to the next vessel station. Therefore, the particular reaction volumes that require the longest time for a given processing step determine the rate of progress of the entire system.

A. Control of the Assembly Subsystem.

As already stated, some embodiments of the system integrate in-line reaction assembly. In such cases, the Main Instrument Process Flow Controller passes commands and needed information, such as sample identification and volume information, to the reaction assembly Pipetting Process Controllers on where to get samples, reagents, and oils. The Pipetting Process Controllers send motor position information to the Pipetting Position Motor Controllers and Pipetting Aspiration/Dispensing Motor Controllers which move liquids to reaction vessels and inform the Main Instrument Process Flow Controller of the arrangement of reactions that have been assembled in the vessels. The Main Instrument Process Flow Controller can, alternatively, command a particular pre-defined arrangement of reactions, but the system works more efficiently if the Pipetting Process Controllers inform the Main Instrument Process Flow Controller of the arrangement of the reactions it can create quickly. The Main Instrument Process Flow Controller can then record the arrangement in a Local Storage Database such that when fluorescence data is collected, the system can determine what particular reaction mix generated what fluorescence.

B. Control of the Photonic Heating Subsystem and the Microcontroller Temperature Feedback and Light Source Control Subsystem.

The photonic heating subsystem employs proportional-integral-derivative (PID) controller hardware or software in combination with custom-developed heating control rule sets to determine the energy needed to drive the light sources. PID parameters and rules are tuned to provide the fastest possible heating without significant overshoot of set point desired temperatures.

As shown in FIG. 11, the Main Instrument Process Flow Controller sends heating profile info, including what temperature set points to achieve and how long to hold the reaction volume at each temperature, to the Heating Controllers and triggers the Heating Controllers to send temperature set point information to the PID Heating Power Regulator. In response, the PID Heating Power Regulator transmits the power-level information to the Heating Light Source Power Supplies, which provide the appropriate energy output to the Heating Light Sources (i.e., the electromagnetic radiation sources). The Heating Light Sources then emit electromagnetic radiation to the vessels. As discussed elsewhere herein, present system comprises a plurality of Temperature Sensors (i.e., thermal detection devices, such as optical fibers in optical communication with a thermal infrared sensing device, thermistors, or thermocouples), which, in some embodiments, provide real-time PCR temperature cycle information. Individual electronic and software sub-systems reduce the load on some main instrument controllers, especially if the Main Instrument Process Flow Controller processor speed is limited. For instance, heating occurs very fast in small volume reactions.

In order to accurately and quickly control the heating process, temperature feedback values are provided approximately every 100 to 200 milliseconds. By employing a separate heating control processor system, the processor is not involved with non-heating control tasks and can handle the quick feedback and control turnaround time required to prevent potential overheating. Thus, a temperature feedback and light source control subsystem is provided wherein the voltage, current, or infrared image information generated by the Temperature Sensors is sent to a Temperature Sensors Signal Processor that provides feedback temperature information to the PID Heating Power Regulator, which, in response thereto, sends the updated power-level information to the Heating Light Source Power Supplies to adjust the energy output for the Heating Light Sources.

Once the temperature set point is reached, the PID Heating Power Regulator transmits this information to the Heating Controllers. At this point, the Heating Controllers will command the PID Heating Power Regulator to provide additional output energy to the Heating Light Sources to raise the temperature of the reaction to the next temperature set point, or, if the PCR temperature cycle is complete, the Heating Controller will command the PID Heating Power Regulator to terminate the energy output thereby turning off the Heating Light Sources. Once the photonic heating subsystem has completed a PCR temperature cycle, the Heating Controllers inform the Main Instrument Process Flow Controller, e.g., by data communication protocols or by digital line states, that the reaction is complete and awaits further instructions.

C. Control of the Fluorescence Detection Subsystem.

The Fluorescence Detection Controllers provide for functionality to turn on and off Fluorescence Excitation Light Sources when initiated by command from the Main Instrument Process Flow Controller. Likewise, initiation of emission light detection by the Fluorescence Emission Detectors is managed by the fluorescence detection subsystem. As shown in FIG. 11, the Main Instrument Process Flow Controller triggers the Fluorescence Detection Controllers that activate the appropriate Fluorescence Excitation Power Supplies resulting in the emission of fluorescence excitation light from one or more Fluorescence Excitation Light Sources. As described elsewhere herein, the fluorescence excitation light may be conducted to each vessel containing an aqueous oil matrix when that vessel is in the PCR product detection position. The fluorophores in the aqueous reaction mix volume respond to the fluorescence excitation light having the appropriate spectral wavelength and emit fluorescence emission light that is carried to a Fluorescence Emission Light Detector. The Fluorescence Emission Light Detector sends raw signal information to the Fluorescence Signal Processors, which collect, process, and report the data as relative fluorescence units to the Fluorescence Data Logger. The Fluorescence Data Logger passes the relative fluorescence unit information to a Local Storage Database and/or a Genetic Analysis Processor configured to run PCR data analysis software, which determines the genetic allele call to report based on the fluorescence data and information provided by the sample and reaction assembly plan information.

In a preferred embodiment, fluorescence data is collected after each PCR temperature cycle. In some aspects, the quality and characteristics of the PCR reactions are such that the PCR data analysis software program informs the Main Instrument Process Flow Controller that a reliable genetic call has been made based on already available information, and the Main Instrument Process Flow Controller can then instruct the Heating Controllers and the Fluorescence Detection Controllers to terminate subsequent processing of the particular aqueous reaction mix volume corresponding to the genetic call data. This additional feedback control saves energy and time.

D. User Interfaces and External Systems.

In the embodiment depicted in FIG. 11, the system employs an LCD or video image display to provide status information about the instrument (i.e., the Instrument LCD Status Display). There is also a Manual Control Interface which allow functions, such as manually starting, pausing, or aborting instrument operations. Also shown in FIG. 11 is a PC-Based User Interface which can be a separate PC-based application or web-site user interface. Such an interface would allow multiple users the ability to send information to an instrument to setup and begin a run or to load additional reactions into a run that has already begun.

Laboratory Information Management Services (LIMS) are well known in the art and are software-based laboratory and information management systems with features, such as workflow and data tracking support, flexible architecture, and data exchange interfaces, that support a laboratory's operations. Thus, in some embodiments, the present system comprises a LIMS program. Shown in FIG. 11 are external systems that include a LIMS Data Exchange Services communicatively connected to the LIMS Database and the Local Storage Database and configured to send "run schedule" and plan information to the PC-Based User Interface and "run components" plan information to the Main Instrument Process Flow Controller.

A number of variations on the components of the system of the invention may be used, as exemplified below.

Containers

Many commercially available microtiter plates, tubes, vials, and multi-chamber liquid holding devices were examined in an attempt to find a suitable container to support the liquid volume while accommodating light-mediated heating. The liquid volume is flexible depending on specific needs, and smaller volumes can generally be heated faster with less light energy input. However, for convenience and simplicity in the prototype systems, a 3 microliter aqueous droplet in 5 microliters of oil was routinely used. Size, shape, and wall thickness were all factors that made examined commercially available containers poor choices for supporting rapid and controlled light-mediated heating of the selected liquid volume. Some containers did not have a bottom suitable for a sufficient area of gold metal. Many others had a wall thickness that created a thermal mass and heat dissipation rate that was too large to be practical with the desired light sources. High wattage lasers were often required to provide sufficient light energy to heat even small volumes of liquid in some containers. Some container shapes and sizes produced uneven heating of the liquid that resulted in poor thermo-cycling. Some containers melted, delaminated, or deformed under the heat generated by the gold. Ultimately, thin-walled, vacuum-formed plastic containers were fabricated and these proved to work very well. Such vacuum-formed arrays of wells are relatively inexpensive, potentially disposable if desired, and are adaptable to all of the examined embodiments of the system. Vacuum-forming molds were constructed, utilizing stainless steel pins, that produce uniform thin-wall container arrays in any desired arrangement and configuration of one or more well.

Figure 14:
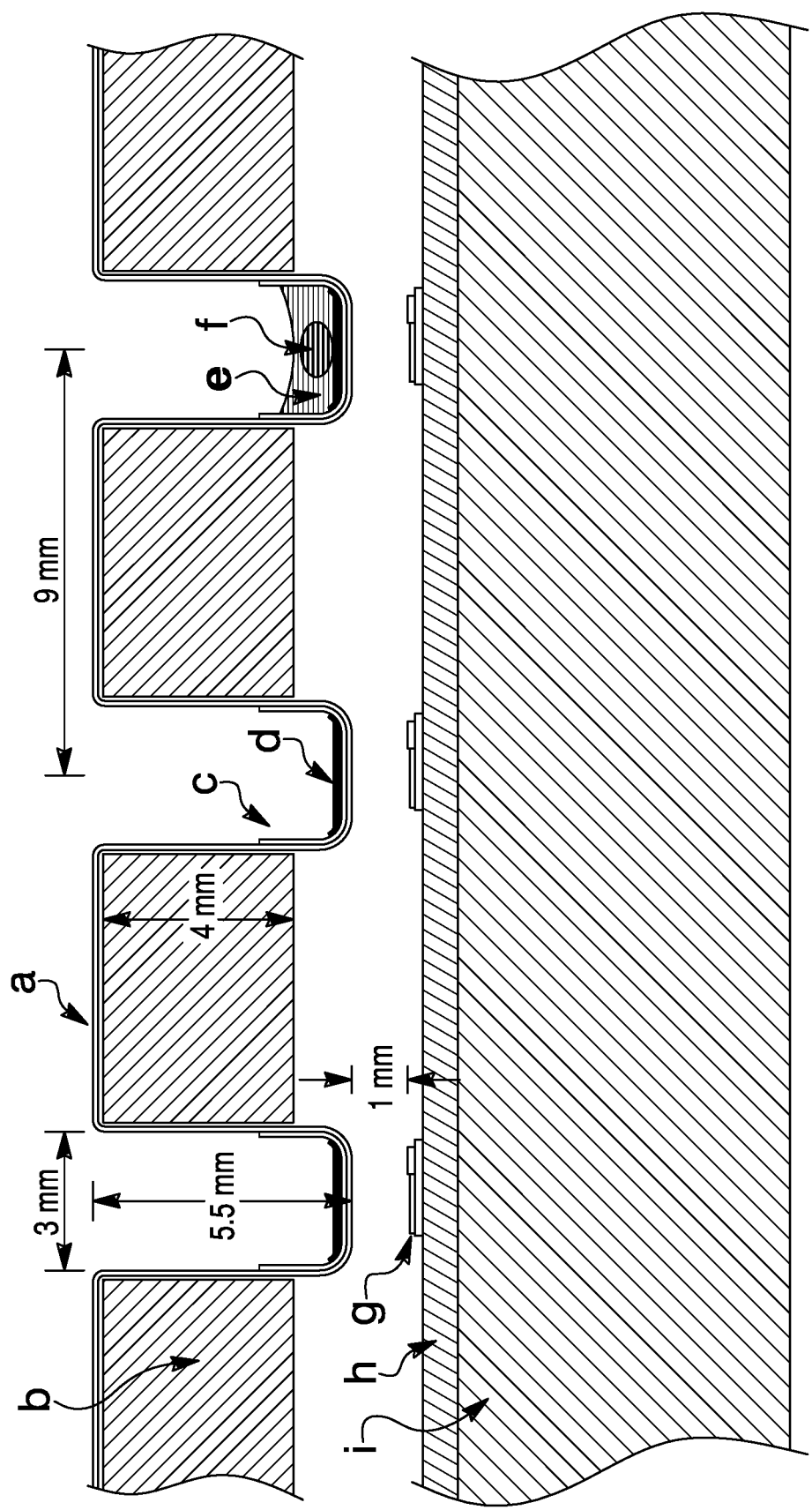
FIG. 14 shows the structure of a multi-well plate and surface mounted LEDs in an embodiment of the invention.

Single well containers, strips of wells, and arrays of rows and columns of wells can easily be produced. Most multi-well arrays are fabricated with a 9 millimeter center to center spacing of the wells to support industry standard laboratory multi-tip pipetting technologies. However, any spacing or desired arrangement is feasible. Several plastic sheet materials available for vacuum-forming/thermos-forming were tested for this purpose. Several were functional. However, clear, transparent PETG (Polyethylene Terephthlate Glycol-Modified) sheet with a thickness of 0.04 inches was selected and employed for most container arrays. As illustrated in FIG. 14, for most prototype and test systems, arrays of flat-bottom wells (a) with an internal diameter of 3 millimeters and depth of 5.5 millimeters were fabricated. Since these thin-walled well arrays lacked the rigidity of many thicker-walled containers, large arrays of wells required a support structure (b) to prevent bending, sagging and warping of the array. Support was provided by a 0.125 inch (4 millimeter) thick acrylic sheet which was laser-cut to have an arrangement of holes matching the positions and diameters of the wells in the PETG vacuum-formed array of wells. The vacuum-formed well containers were inserted into the holes in the support plate. This resulted in a device with arrays of wells protruding approximately 1.5 mm below the support plate. The support plate provides not only support for the array of wells but also provides precise alignment of the wells over the light sources.

Light/Heat Conversion Materials

Figure 13:
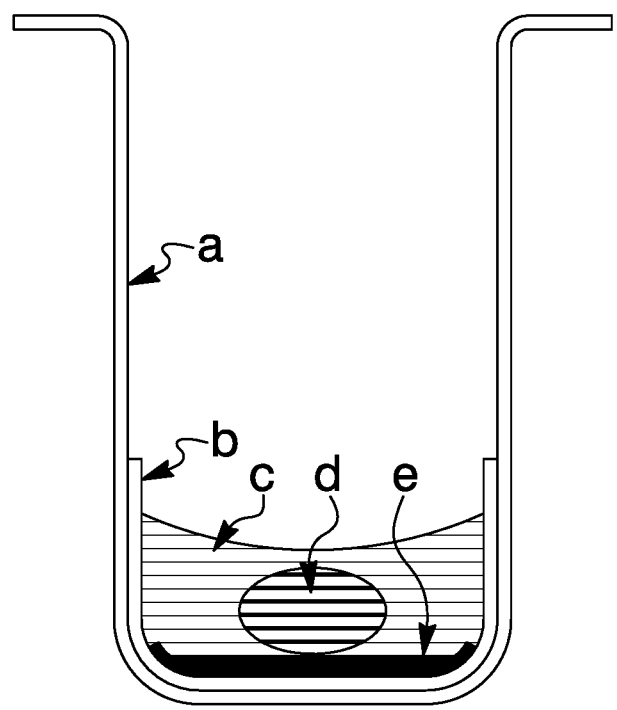
FIG. 13 shows the components of a well in an embodiment of the invention.

To absorb the routinely employed blue wavelength light and convert it to heat to drive thermo-cycling, a gold metal film is needed on the bottom of the reaction well (FIG. 13). Ideally, vapor-deposited or electro-plated gold, applied directly to the bottom of the well, could be used. However vapor-deposition and electro-plating processes are inconvenient and impractical for most prototype testing. An alternative is to employ gold-coated foil or film disks (e in FIG. 13) inserted into the bottom of the wells. These disks are punched from commercially available sheet stock of gold-coated Mylar film or gold-coated aluminum foil. Most early prototype testing was performed with gold-coated Mylar film. However, it was found that the Mylar could melt, shrink, or lose its gold coating under certain circumstances. Also, it was difficult to keep the Mylar film from floating in some liquids, especially when the temperature of the liquid is rapidly changed and gas bubbles are possible in the liquid volume. Commonly available aluminum foil proved to be too thick to work effectively. However, a very thin, gold-coated, aluminum foil, normally used as a candy wrapper, (CK Products/Oasis Supply 4×4 inch gold foil candy wrappers 89-44G) was found that worked very well. A punch was fashioned from a sharpened steel rod and steel plates with a matching diameter hole that allowed 3 mm foil disks to be generated. These disks were inserted with a small diameter vacuum tip pick up pen, gold side down, in the wells of the vacuum-formed containers. The disks were sized to fit tightly in the bottom of the wells.

Oil Matrices

As previously mentioned, two oils can be used to support the aqueous droplet, a silicone encapsulation oil and a perfluorocarbon carrier oil, and this has certain advantages for centering and contamination control. However, it was found that the use of two oils could result, under some circumstances, in a "lava lamp" effect when the liquids are rapidly heated and cooled by the light. Observations made with a small video camera positioned to the side of a single well container showed that employing some perfluorocarbon oils caused the entire volume of liquid to churn, roil, and split into smaller droplets during rapid heating and cooling. Removing the perfluorocarbon oil and only using a silicone oil (c in FIG. 13) eliminated this churning. There are still thermally-induced currents established in the oil, as indicated by studies of videos of small particles that can be added to the oil. However, these currents did not significantly move the aqueous droplet (d in FIG. 13) which tended to rest in the center of the oil just above the gold foil on the bottom of the well. In fact, these small currents promote a more uniform temperature throughout the total liquid volume making temperature monitoring and control easier. The chosen volumes of the aqueous droplet and the volume of the oil was determined by the size and shape of the container and provided for a layer of oil over the aqueous droplet approximately 0.5 to 1 millimeter deep. This oil covering prevented evaporation of the aqueous droplet.

Hydrophobic Coating

To provide the centering and contamination control offered by the perfluorocarbon carrier oil, a simple alternative was found that does not require the carrier oil in the liquid volume. The bottom half of each well in the vacuum-formed arrays of wells are treated with a super-hydrophobic coating (HydroFoe™ from LotusLeaf Coatings, Inc.) (b in FIG. 13). Many prototype system embodiments incorporate this coating. The coating greatly enhances the centering of the aqueous droplet in the silicone oil and repels any contact between the walls of the well and the aqueous reaction mixture. In prototype systems each well is treated for 5 minutes with 20 microliters of HydroFoe™. Without the hydrophobic coating, the aqueous droplets could sometimes stick to the walls of the well which proved detrimental to IR thermal imaging and fluorescence detection and allowed for potential cross-contamination issues if the well is used again for subsequent PCR reactions. The super-hydrophobic coating is fairly durable and the well can be used multiple times after one treatment supporting several PCR reactions. Replacing the perfluorocarbon oil with a hydrophobic coating simplifies assembly of reaction volumes, reduces costs, and eliminates potentially hazardous perfluorocarbon waste liquids. While HydroFoe™ is currently used in the prototype systems, there are many other commercially available hydrophobic treatment coatings that would work equally well.

Light Source

Many laser and LED light sources have been examined as possible energy sources to drive heating. Many commonly available blue LEDs did not provide the necessary energy output to rapidly heat the desired reaction liquid volumes. Some lasers and LEDs were relatively expensive. Some were large and bulky and not well suited to being positioned under wells that could be close together in an array of wells. Some required expensive and complicated lens systems to focus the light. Some lasers produced an intense, small diameter, collimated light source that could easily be positioned to illuminate only the gold metal surface at the bottom of the reaction well. These lasers could be used to very rapidly heat most tested liquid volumes. However, these lasers are generally considered potential eye hazards which were considered undesirable. LEDS were found that were small, inexpensive, and provided the needed light intensity. Furthermore, the selected LEDs could be positioned very close to the bottoms of the wells in the thin-walled vacuum-formed containers (FIG. 14) such that most of the light emitted by the LEDs would intersect the gold metal layer in the bottom of the wells. This makes these selected LEDs energy efficient and eliminate the need for a focusing lens. The Luxeon Rebel ES 1 W 700 mA royal blue LEDs (Lumileds Holding B.V.) worked well if the dome is removed from the LED. The Luxeon Z Series ES 700 mA LEDs also worked well and are "naked die" LED devices without a protective dome. Removing the dome allows the die to be positioned very close (within 1 millimeter) to the bottom of the vacuum-formed well, improving energy transfer efficiency. These LEDs are available as surface-mount devices on tiny pads with contacts allowing them to be easily mounted to a printed circuit board.

Light Source Positioning

Figure 16:
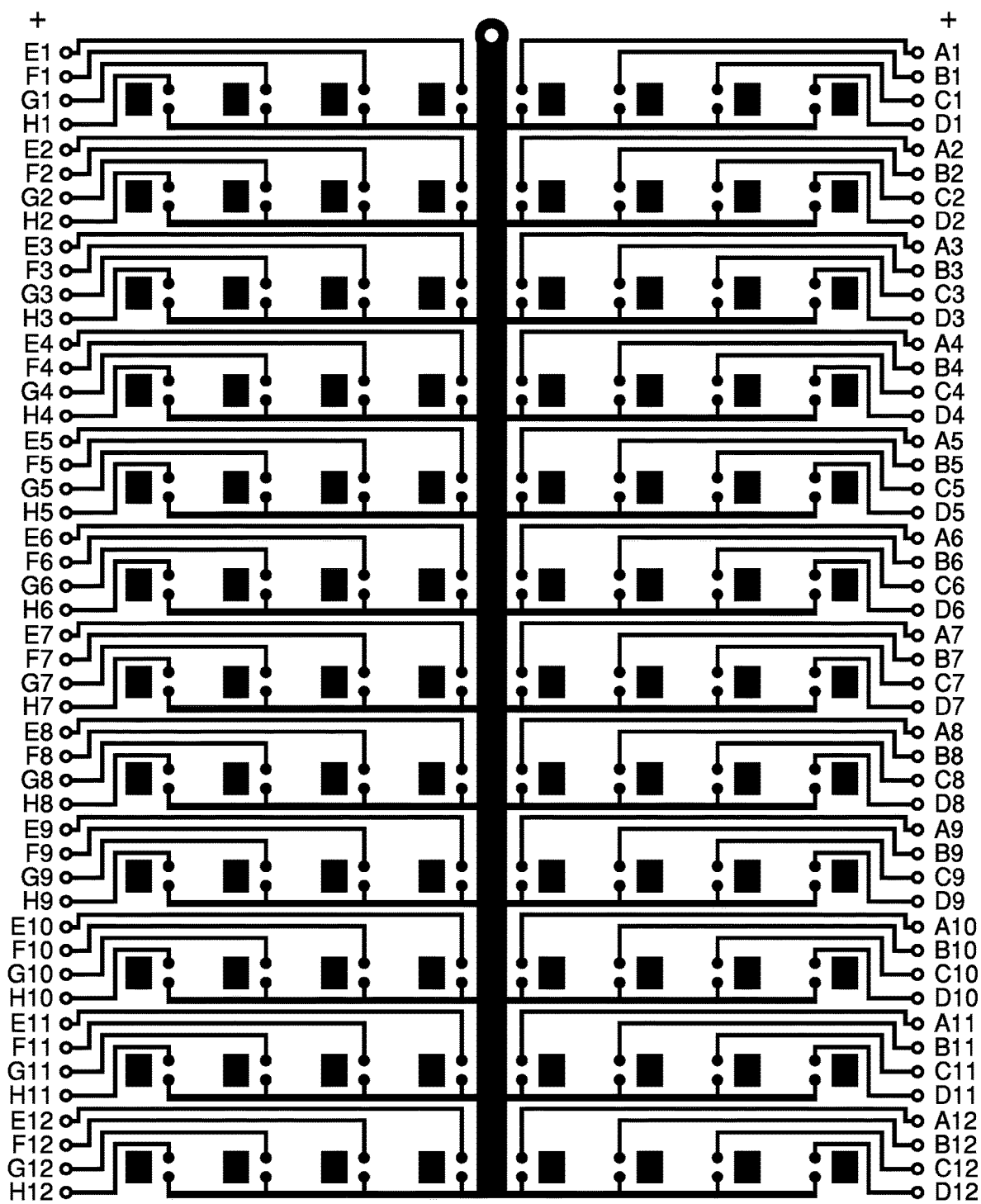
FIG. 16 shows a schematic for a printed circuit board for independent control of 96 LEDs in an embodiment of the invention.

For a prototype device a printed circuit board was designed allowing for independent control of 96 LEDs positioned with a 9 millimeter spacing (FIG. 16). This particular design supports a commonly used embodiment of the system that utilizes multi-tip pipetting technologies designed for the international standard layout and footprint of wells in a 96 well microtiter plate. Similar printed circuit boards for any other arrangement of LEDs are feasible.

Not all input electrical energy is converted to light. A significant amount of heat is generated by an LED. To maintain stability and prolong the life of the LED, the LED may be mounted on a heatsink to allow this heat to be dissipated. In prototype systems fans are positioned to carry this heat away from the LEDs and the wells above the LEDs. Additional fans are positioned to provide an airflow across the bottoms to the wells. These fans are powered on and off automatically by microcontroller software to promote more rapid cooling of the wells when desired.

Light Source Drivers

Figure 15:
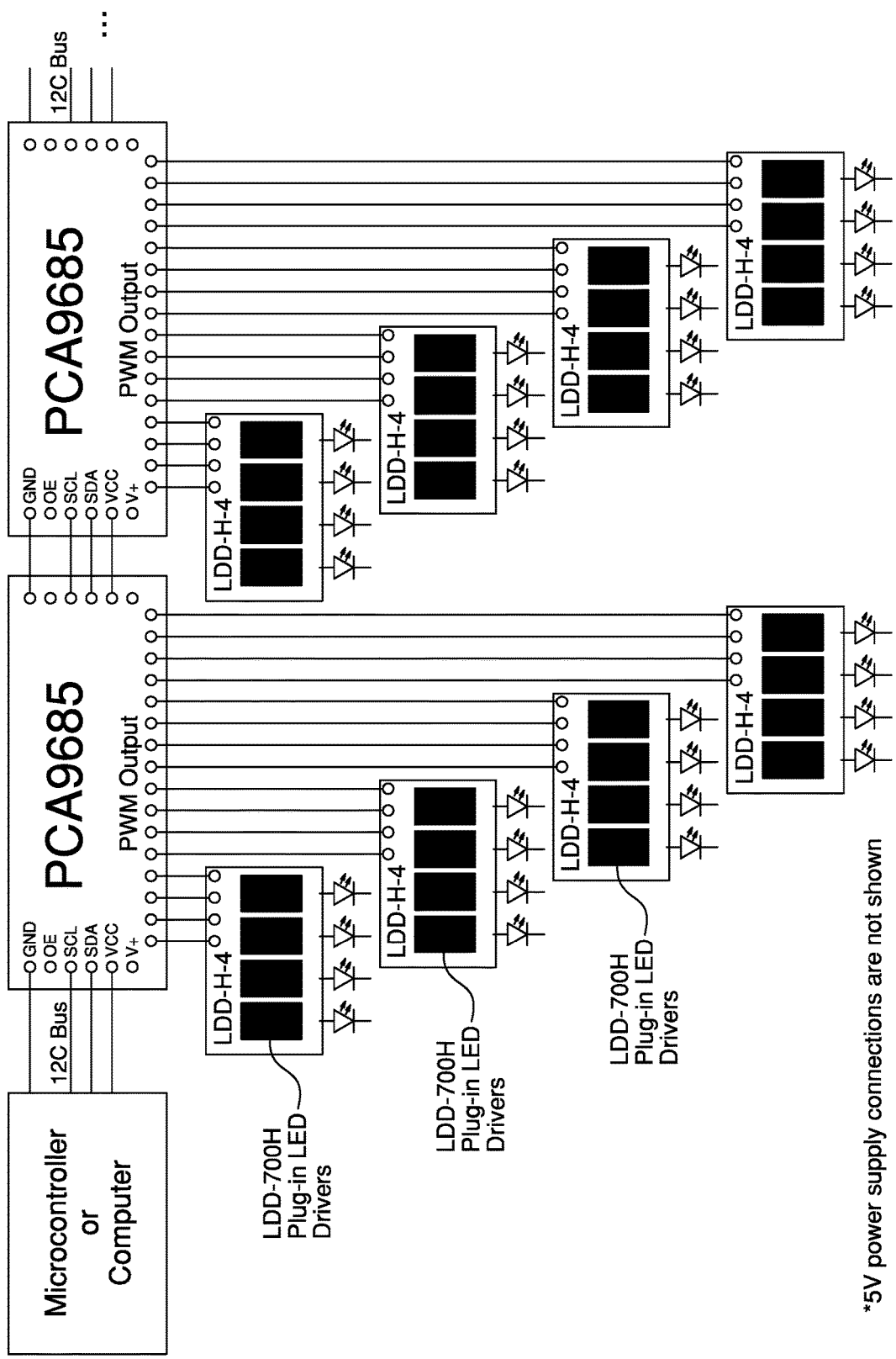
FIG. 15 shows an electronic circuit for powering LEDs in an embodiment of the invention.

To support a prototype system, an LED driver system has been assembled that provides pulse-width-modulation (PWM) power control of each LED over a single I2C bus from a microcontroller. The LED driver system employs a series of PCA9685 modules, available from multiple electronics component sources. Each PCA9685 module can provide 12-bit PWM signals for up to 16 addressable LEDs. The modules contain their own internal clock eliminating the need to continuously refresh the PWM settings. The PCA9685 modules can be assembled in a series allowing for several hundred LEDS to be controlled on one I2C bus by a single microcontroller. 6 modules are required to drive 96 LEDs. To accommodate the current needed to drive the individual 1 W LEDs, the PWM signal output for each LED from a PCA9685 is routed to a RapidLED Meanwell LDD-700H power driver mounted on a RapidLED LDD-H-4 quad driver board (Rapid LED). An LDD-700H is required for each LED. Each driver board is connected to a power supply and has connections for each LED output. FIG. 15 shows the basic arrangement of components needed to drive the LEDs. Only 32 LEDs are shown in the diagram but an assembly was designed for testing that drives 96 LEDs. This design is easily extended for an even larger number of LEDs and is a simple, inexpensive, and flexible way to drive multiple LEDs in prototype systems. Custom-designed, similar functionality, LED control circuits are also possible.

Non-Contact Temperature Sensors

To control and modulate the intensity of the LEDs, thereby regulating temperatures, it is ideal to use feedback from temperature sensors that can continuously monitor the temperatures of each liquid volume. Subtle differences in size, and composition of the reactions can cause significant variability in timing and required power levels during heating. Simple thermistors or thermocouples can be inserted into each reaction to provide this feedback temperature information. For many prototype and test systems, 0.005 inch thermocouples (Omega Engineering Inc.) were inserted into individual wells. However this presents multiple problems with contamination control, reuse of containers, and easy movement of arrays of wells for some embodiments of the system. The preferred method of temperature monitoring for most embodiments is the use of non-contact IR sensors.

Tests of multiple non-contact IR sensors have been performed. The size, shape, position/alignment, cost, accuracy, and field of view of many available discrete, single measurement, non-contact IR temperature sensors were inappropriate for successful use of these sensors in our prototype systems. Best results, to date, have been achieved with non-contact IR imaging technologies that can simultaneously report temperatures from multiple pixels in an acquired thermal image. This overcomes the need for many individual sensors and supports faster and easier acquisition and manipulation of temperature data for multiple wells. Also, by analyzing thermal images of entire areas occupied by reaction wells, precise alignment of individual discreet temperature sensors is not needed. While many available IR imaging cameras can be employed, temperature monitoring has been performed in prototype systems with the FLIR Lepton® Radiometric sensor and the FLIR Ax5-Series thermal imaging camera (FLIR Systems, Inc.). Both thermal imaging devices can be interfaced to a microcontroller or computer and can report temperatures from images of observed objects. By positioning these imaging systems above an array of reaction volumes, temperatures can be monitored while light-mediated heating is occurring. In prototype systems the pixel with the highest reported temperature corresponding to a well location was used as the temperature of the well. The temperatures reported are surface temperatures and can be a few degrees less than the temperatures reported simultaneously by thermocouples embedded closer to the gold layer. However, it has been possible to calibrate and compensate for these temperature differences as long as container sizes, configurations, and liquid volumes are maintained constant.

Fluorescence Sensors

The typical prototype system test PCR reaction mix is a two probe (bi-allelic) Taqman™ PCR reaction employing fluorescent FAM and VIC probes. Some reactions also contain an unbound ROX dye used to assess volumes and concentrations of reaction components. A full spectral excitation and emission scan of these PCR reactions showed narrow excitation and emission windows where minimal emission crosstalk between the 2 probe dyes occurred. For our specific test PCR reaction mixes, the optimal FAM excitation window was 475-500 nm with an optimal emission window between 510-525 nm. The VIC fluorescence optimal excitation window was 525-535 nm with an optimal emission window of 555-565 nm. These excitation and emission windows were used to select excitation light sources and excitation and emission optical filters in prototype systems.

Many discrete reaction optical fluorescence sensors and scanning fluorescence sensor technologies can measure fluorescence generated from individual reaction volumes, one by one. However, to provide the fast fluorescence data collection needed for real-time (cycle by cycle) fluorescence measurements and to make the overall speed of the prototype systems as fast as possible, it is desirable to simultaneously measure fluorescence from multiple wells. This can be achieved by use of fiber optics arrays and/or by parallel use of multiple fluorescence sensors. However, fluorescence imaging camera technologies have been adopted in most of the prototype systems. Sensitive ultra-low-light imaging cameras used with appropriate excitation and emission fluorescence filters are able to collect FAM and VIC fluorescence probe Taqman PCR product data from multiple reactions simultaneously in a prototype system. The sensitivity of the cameras has not been a major problem. Technological advances in this area in the last few years have made it relatively straight forward to find cameras with suitable capabilities. Several relatively low cost fluorescence microscopy and fluorescence astronomy cameras have been examined. Examples of workable cameras include the Sony A7s II (Sony Corporation), Tucsen ISH1000 (Tucsen Photonics), ToupTek E3CMOS (ToupTek Photonics), AmScope MT5000 and AmScope MF603C (United Scope LLC).

Excitation Light Sources

Excitation and emission filters and excitation light sources were engineered. For devices where only one well is observed, occupying a very small area, numerous light sources and narrow-band optical filters are possible. However, for fluorescence excitation, with illumination of a relatively large area occupied by an array of wells of PCR reaction liquids, an intense and uniform excitation light is needed. Available LED light sources have a very wide spectral output and must be heavily filtered to provide the needed narrow bandwidths needed to support clean separation of FAM and VIC fluorescence emissions. Standard narrow bandpass interference filters can be positioned over LEDs to provide the desired spectral window but the angle of incidence of light hitting an interference filter must be precisely controlled to eliminate undesirable spectral shifts. For a physical assembly with such an arrangement to evenly cover a large area occupied by an array of wells is a significant engineering challenge. To provide the needed light intensity and narrow excitation wavelengths, lasers have provided a more workable solution. Relatively safe, laser-line devices can project an intense line of light across several PCR wells simultaneously. By nature, the bandwidth of light output from a laser is very narrow. This laser line can be rapidly moved to cover additional wells or the wells can be moved under the laser line to capture fluorescence from multiple rows of wells. Two lasers, one for each desired excitation wavelength can sequentially irradiate all of the reaction volumes and still only take a few seconds. Another alternative is to use a galvo-head mirror scanner to deflect a laser point beam sequentially to each of the desired well locations. Such devices are commonly used in projecting laser patterns for shows and large audience displays. An inexpensive galvo-head mirror scanner can move to over 20 thousand points per second. For fluorescence excitation for both laser line and galvo-head scanning lasers, fluorescence light emitted by the FAM and VIC probes can be sequentially detected by a camera that can integrate over the time required to scan a desired number of wells. A single camera with a suitable 2 wavelength bandpass filter can be employed or two cameras, each with a less expensive single wavelength narrow bandpass filter can be used.

The present disclosure is illustrated by the following examples. The foregoing and following description and the example are not intended to be limiting but rather are illustrative of the described embodiments. Hence, it will be understood that the present disclosure is not limited to the specific details of the examples.

Example 1

Figure 17:
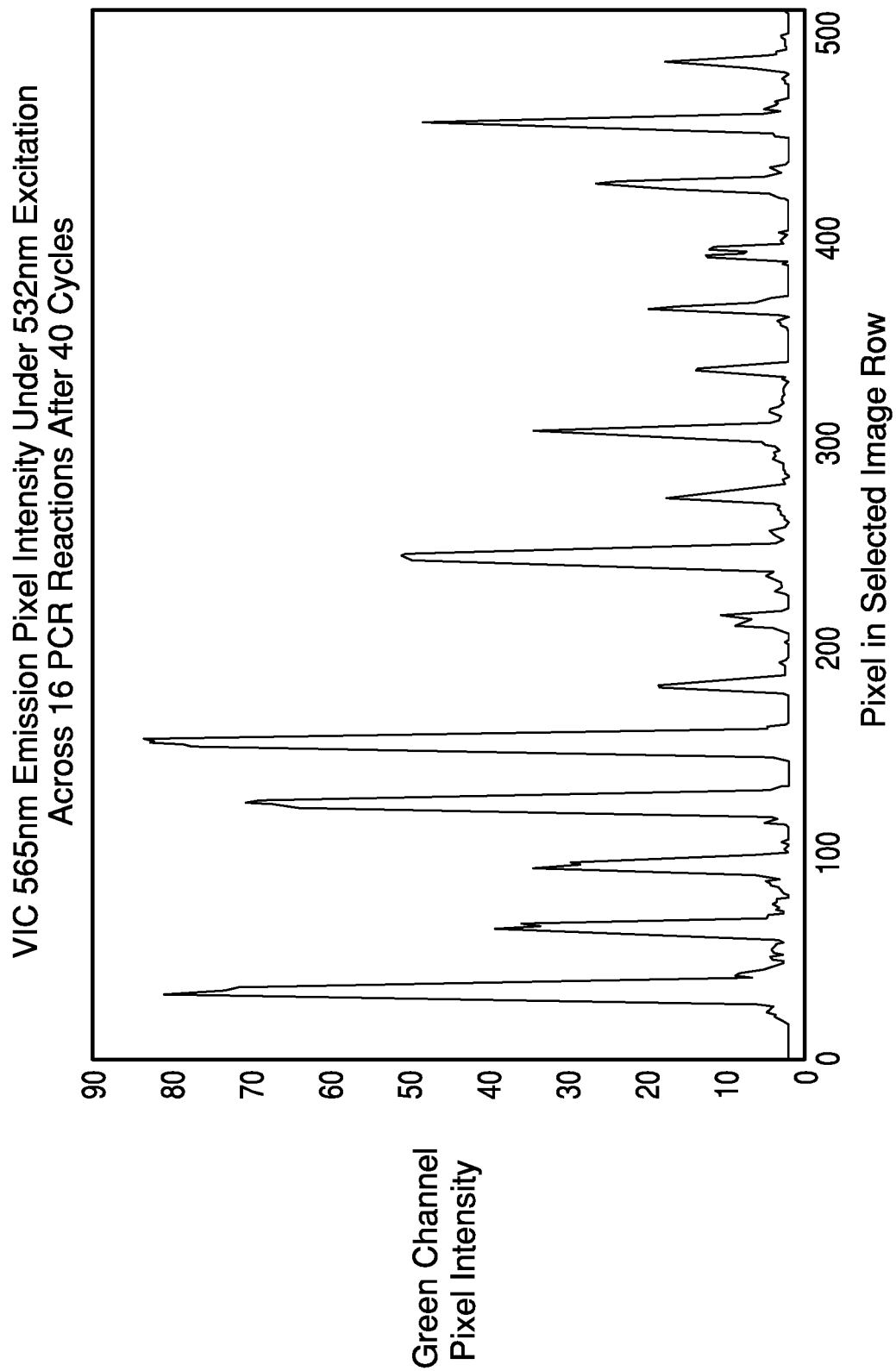
FIG. 17 shows the observed fluorescence from 16 reaction wells after 40 cycles of PCR using an embodiment of the invention.

FIG. 17 illustrates the observed fluorescence from 16 reaction wells after 40 cycles of PCR extracted from a single (200 msec exposure) image captured by a ToupTek E3CMOS camera. The fluorescence emission light was filtered through a 565 nm+/−5 nm narrow bandpass interference filter before entering the camera lens. The wells were illuminated by an inexpensive 20 mW 532 nm laser line (Laserlands, Inc.) to provide the VIC excitation light. The collection of 16 samples were a variety of genotypes with homozygous VIC, heterozygous VIC, and VIC negative samples. This variation in genotypes contribute to the variation in height of the peaks. VIC fluorescence is demonstrated here since it is more difficult to cleanly measure VIC fluorescence than FAM fluorescence in typical PCR reactions. Pixel intensity information was extracted from the acquired image using publically available ImageJ image analysis software (imageJ.nih.gov).

When fully automated, using the above camera system, acquiring fluorescence images and extracting fluorescence intensity from the pixels in the images takes only a few seconds. Multiple system embodiments to utilize this approach are feasible. A set of reaction wells could be moved from a location where heating is performed to an adjacent chamber where the cameras can measure fluorescence. Alternatively, the fluorescence detection camera(s) can be positioned next to an IR imaging camera or discrete IR sensors over the same location where wells are heated. The 450 nm 1 W LEDs used to currently provide heating light energy in prototype systems produce a very bright and wide spectral output that swamps out fluorescence detection even with the best emission blocking filters available. Therefore, in these prototype device embodiments the heating light can't be on while fluorescence measurements are being made. This results in a few seconds of additional cooling of the reaction volumes after each thermo-cycle during fluorescence measurements before the next heating cycle can begin. While temperatures of the reaction volumes fall initially very fast (generally 6 to 10 degrees per second) from the 95 degree C. denaturing temperature when the heating light is extinguished, the rate of temperature drop slows after the first few seconds as the difference between the ambient temperature and the reaction temperature lessens. Even with such a delay in starting the next heating cycle, the additional time required to bring the reaction volume back to the desired annealing temperature to start the next cycle is only 1 or 2 seconds in prototype systems with the reaction volumes specified.

The present disclosure is illustrated by the following examples. The foregoing and following description and the example are not intended to be limiting but rather are illustrative of the described embodiments. Hence, it will be understood that the present disclosure is not limited to the specific details of the examples.

Example 2

PCR Product Detection from Light-Mediated Aqueous Oil Matrix Reactions

Two TAQMAN® probes and custom-designed primer pairs forming a bi-allelic interrogation of a DNA target loci were tested with a light-mediated temperature-cycling in an aqueous oil matrix. The probes and primers were combined with typical TAQMAN® PCR enzymes and reagents in sealed wells and were run through as many as 40 PCR temperature cycles in a water bath thermocycler. After thermocycling, the PCR products were then measured in a commercial fluorescence reader at emission wavelengths for the FAM and VIC dyes that are associated with the two probes for the particular locus alleles. Elevated FAM and/or VIC fluorescence indicates the presence of amplified PCR products for the DNA alleles for which the probes and primers were designed.

For detection of light-mediated PCR products in an aqueous oil matrix, the previously extracted DNA samples were acquired from a routine genotyping production process. These samples constituted known genotypes. Sample 1 was known to produce a PCR product for the selected FAM probe. Sample 2 was known to produce a PCR product for the selected VIC probe. Sample 3 was known to produce a PCR product for both the FAM and VIC probes for the selected specific DNA locus.

A 384-well, clear flat bottom, plate was prepared with the inside bottom of the wells coated with a thin layer of gold emulsion paint. A 0.005 inch thermocouple was inserted and positioned in the painted well such that the thermocouple bead was located approximately 0.5 mm above the gold paint. Aqueous oil matrix PCR reactions were assembled for each of the samples and for a no template control (no DNA added to the reaction) in the prepared wells. Each aqueous oil matrix was composed of 2 µl of an aqueous PCR reaction mix, identical in composition to production genotyping process, in 4 µl of a silicone encapsulation oil in 4 µl of a perfluorocarbon carrier oil.

Figure 12:
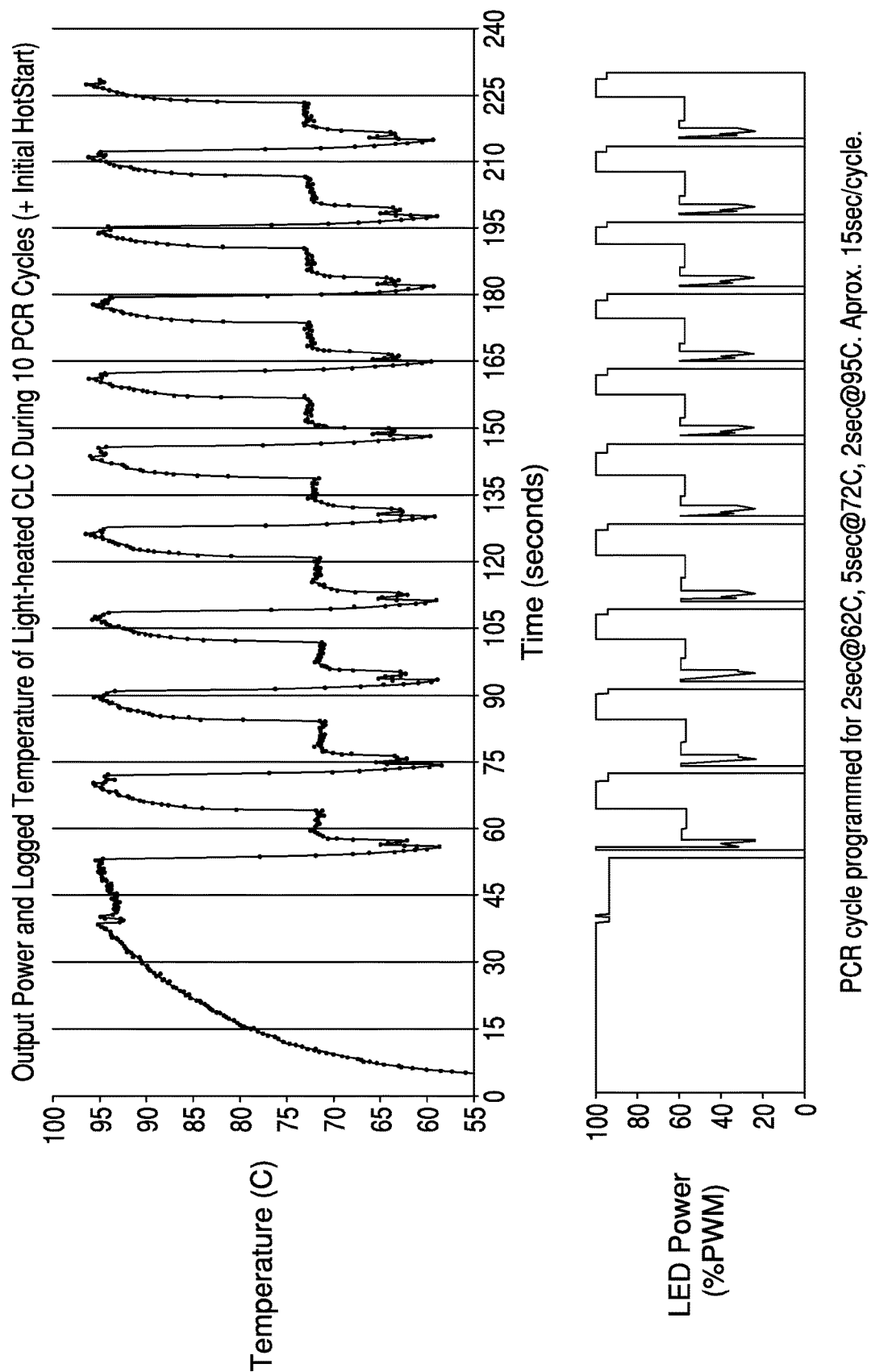
FIG. 12 shows the output power and logged temperature of a light-heated aqueous oil matrix. The top graph shows temperature over time. The y-axis represents degrees Celsius, and the x-axis represents time in seconds. The bottom graph shows LED power over time. The y-axis represents LED power in percentage pulse width modulation (PWM), and the x-axis represents time in seconds. PMW is a measure of the percentage of time per second that power is turned on, as produced by a series of power pulses during the second. Pulse frequency can be adjustable, whereas pulse length is adjustable dependent on the total energy needed per second.

One by one, the aqueous oil matrix reactions in the 384 well plate were positioned over a 200 mW 405 nm laser diode focused to irradiate an area of the gold paint approximately 1.5 mm in diameter. An Arduino microcontroller, such as those described in depth on the Arduino website, and regulated power supply were employed to drive the light source such that the light could be flashed on and off as many as 500 times per second with pulse width modulation of the power dependent on the temperature sensed by the thermocouple in the well. The microcontroller was programmed to provide two seconds at an achieved temperature of 62° C., followed by five seconds at an achieved temperature of 72° C., followed by two seconds at an achieved temperature of 95° C. The microcontroller was programmed to repeat this temperature profile 40 times to accomplish the PCR amplification. The temperature profile data from the first ten PCR temperature cycles is provided in FIG. 12.

Before and after the light-mediated PCR thermocycling, the plate was moved to a commercial fluorescence plate reader where FAM and VIC fluorescence was measured for each reaction well. Elevated fluorescence was observed for both FAM and VIC probes for samples as expected. The results of the test are shown in Table 2:

TABLE 2

Relative fluorescence of known genotype samples before and after 40 light-mediated PCR cycles

| Expected Result | FAM (before) | FAM (after) | VIC (before) | VIC (after) |
|---|---|---|---|---|
| NTC: −FAM, −VIC | 807 | 783 | 635 | 669 |
| Sample 1: +FAM, −VIC | 796 | 1008 | 580 | 712 |
| Sample 2: −FAM, +VIC | 825 | 920 | 670 | 931 |
| Sample 3: +FAM, +VIC | 770 | 1331 | 602 | 1112 |

NTC = no template control

Example 3

DNA Extraction by Heat Shock

A requirement of a PCR amplification system is a source of DNA samples that can be incorporated into the PCR reactions. It has been observed that sufficient quantities of DNA-containing organic material can be found on or in various substrates that have come into contact with various plants or plant parts. Liquid from swabs taken of plant surfaces, small volumes of culture media, or liquids rinsed over various plant parts can contain significant amounts of DNA. Such collected DNA-containing material provides a means of non-destructive DNA sampling of plants. This "shed" DNA-containing material can sometimes be used directly, without further purification, as a PCR DNA source if it is exposed to a "heat shock" to release, unravel, and/or de-compartmentalize the DNA contained within the liquid and/or denature or destroy enzymes and other materials that are detrimental to PCR amplification. Whatever the exact mode of action, a single very rapid heating and cooling treatment can make the DNA available and suitable for PCR. Two or more rapid heating and cooling cycles could potentially enhance this effect for some plant sources. By observation, a single 3 microliter volume of aqueous liquid from media surrounding a plant embryo or cultured plant tissue can contain enough DNA for many PCR reactions.

In one embodiment, heat shock is used to obtain DNA from shed material in an apparatus of the invention using the same heat source used in subsequent PCR amplification steps as described above. In another embodiment, a separate position or location employing a photonic heating apparatus is used to rapidly heat small quantities of liquid containing this shed plant material. As rapidly as possible, raising the temperature of the liquid from room temperature to 90 to 98 degrees C. and immediately lowering it again to room temperature provides the needed heat shock. This process can be further enhanced in some embodiments by lowering the temperature of the liquid to sub-zero temperatures (−20 degrees C. is frequently used) by using Peltier cooling or immersion in a cold bath before the heating treatment. This process can be further enhanced by incorporating a gentle agitation or vibration of the liquid during or after the heat shock. This agitation mixes the liquid uniformly and/or enhances release of the DNA. Such a heating (and optional cooling) apparatus could simplify setup of PCR reactions in handheld or portable devices and/or could be used to speed up a heat shock treatment of single or multiple DNA samples while also reducing energy costs.

In other embodiments, many other DNA extraction and purification processes are possible to provide DNA for photonic PCR reactions. For instance, DNA may be obtained by incubating plant material with an enzyme; the enzyme may be VISCOZYME® L, a multi-enzyme complex containing a wide range of carbohydrases, including arabanase, cellulase, 3-glucanase, hemicellulase, and xylanase. (See the Sigma Aldrich product catalog). Once the plant material is digested by the enzymes, a heat shock could be used to prepare the released DNA for PCR. Alternatively DNA may be obtained using more traditional DNA extraction techniques, such as but not limited to the use of magnetic particles that bind genetic material or any method known to one of ordinary skill in the art.

That which is claimed:
1. A polymerase chain reaction (PCR) amplification and detection apparatus, comprising:
  a) an assembly subsystem comprising:
    i) a plurality of vessels in the form of a continuous polymer strip, each such vessel having a volume of 0.2 to 20 µl and a vessel diameter of 0.5 to 4 mm;
    ii) said plurality of vessels each comprising an aqueous oil matrix, each aqueous oil matrix comprising:
      1) an aqueous reaction mix comprising a polynucleotide sample and reagents, the reagents comprising a first reagent capable of excitation by a fluorescence excitation light having a first spectral wavelength when the first reagent hybridizes to the polynucleotide sample; and
      2) one or two non-miscible oils selected from the group consisting of an encapsulation oil, a carrier oil, and both an encapsulation oil and a carrier oil; wherein components of the aqueous reaction mix do not mix with the one or two non-miscible oils;
  b) a plurality of heating positions, temperature monitoring positions, and PCR product detection positions defining a plurality of alternating first vessels stations and second vessels stations where the plurality of vessels may be stationed, and wherein each of the first vessels stations comprises a heating position, and each of the second vessels stations comprises a PCR product detection position;
  c) a reaction-by-reaction, light-driven photonic heating subsystem comprising a plurality of electromagnetic radiation sources, wherein, when the plurality of vessels are in the heating position, each vessel is in optical communication with an electromagnetic radiation source, and the electromagnetic radiation source emits electromagnetic radiation to that vessel;
  d) a reaction-by-reaction temperature monitoring subsystem comprising a plurality of thermal detection devices, wherein each vessel corresponds to a thermal detection device the thermal detection device is configured to provide a measuring signal dependent on the temperature of the aqueous oil matrix contained in the vessel;
  e) a microcontroller temperature feedback and light source control subsystem communicatively connected to both the photonic heating subsystem and the temperature monitoring subsystem, wherein the microcontroller temperature feedback and light source control subsystem is configured to regulate an energy input required for controlling an output and a duration of an electromagnetic energy emitted by each electromagnetic radiation source through a cycle of reaction temperatures;
  f) a fluorescence detection subsystem comprising:
    i) one or more fluorescence excitation light sources;
    ii) one or more fluorescence emission light sensing devices;
    iii) a plurality of first optical members in optical communication with the one or more fluorescence excitation light sources, wherein, when the vessels are in the PCR detection positions, each first optical member is configured to provide an optical path for fluorescence excitation light having the first spectral wavelength from the one or more fluorescence excitation light sources to one of said vessels containing the aqueous oil matrix, and wherein each first optical member is further configured to provide an optical path for fluorescence emission light from the aqueous reaction mix to the one or more fluorescence emission light sensing devices; and
    iv) an active or passive cooling mechanism at the PCR product detection positions whereby each of the vessels in the PCR product detection positions are cooled; and
  g) a mechanical and electronic control system communicatively connected to a moveable belt and to the assembly subsystem, wherein the mechanical and electronic control system causes the assembly subsystem to assemble the aqueous oil matrices in the plurality of vessels, and wherein the mechanical and electronic control system causes the moveable belt to move the plurality of vessels with the aqueous oil matrix in a step-by-step movement through the assembly subsystem in order to align the plurality of vessels with the aqueous oil matrix with the plurality of alternating first vessels stations and second vessels stations.

2. The apparatus of claim 1, wherein each of the first vessels stations comprise a heating position and a temperature monitoring position, and wherein each of the second vessels stations comprise a PCR product detection position.

3. The apparatus of claim 1, wherein each of the first vessels stations comprise a heating position, and wherein each of the second vessel stations comprise a PCR product detection position and a temperature monitoring position.

4. The apparatus of claim 1, wherein each electromagnetic radiation source is configured to uniformly heat the volume of the aqueous reaction mix in each corresponding vessel when the vessel is in the heating position through the cycle of reaction temperatures comprising: (i) an annealing temperature in the range from about 50° C. to about 65° C.; (ii) an elongation temperature in the range from about 65° C. to about 75° C.; and (iii) a denaturation temperature in the range from about 90° C. to about 99° C.; and wherein the active or passive cooling mechanism is configured to cool each of the vessels to a temperature range from about 55° C. to about 65° C. when the vessel is in the PCR product detection position.

5. The apparatus of claim 4, wherein the aqueous reaction matrix is heated through the cycle of temperatures (i), (ii), and (iii), in less than or equal to 20 seconds, and wherein the volume of the aqueous reaction mix portion of the aqueous reaction matrix is less than or equal to 10 µL.

6. The apparatus of claim 5, wherein the aqueous reaction matrix is heated through the cycle of temperatures (i), (ii), and (iii), in less than or equal to 15 seconds, and wherein the volume of the aqueous reaction mix portion of the aqueous reaction matrix is less than or equal to 10 µL.

7. The apparatus of claim 6, wherein the aqueous reaction matrix is heated through the cycle of temperatures (i), (ii), and (iii), in less than or equal to 10 seconds, and wherein the volume of the aqueous reaction mix portion of the aqueous reaction matrix is less than or equal to 10 µL.

8. The apparatus of claim 6, wherein the cycle of reaction temperatures in (i), (ii), and (iii) is repeated for an additional 1 to 60 cycles.

9. The apparatus of claim 1, wherein the fluorescence detection subsystem further comprises:
v) a first excitation filter which receives light from the one or more fluorescence excitation light sources and allows passage of the fluorescence excitation light having the first spectral wavelength;
vi) a first emission filter for allowing transmission therethrough of fluorescence emission light to the one or more fluorescence emission light sensing devices from the aqueous reaction mix in response to the fluorescence excitation light having the first spectral wavelength and for substantially blocking transmission of wavelengths other than the wavelengths of the emitted light; or
vii) both v) and vi).

10. The apparatus of claim 1, wherein each first optical member is further configured to provide an optical path for fluorescence excitation light having a second spectral wavelength from the one or more fluorescence excitation light sources to one of said vessels containing the aqueous oil matrix when the vessel is in a PCR product detection position, wherein the volume of the aqueous reaction mix comprises a second reagent capable of excitation by the fluorescence excitation light having the second spectral wavelength when the second reagent hybridizes to the DNA sample, and wherein each first optical member is further configured to provide an optical path for fluorescence emission light from the aqueous reaction mix to the one or more fluorescence emission light sensing devices.

11. The apparatus of claim 10, wherein the first reagent, the second reagent, or both the first reagent and the second reagent comprises a nucleic acid probe covalently linked to a fluorophore.

12. The apparatus of claim 1, wherein the one or more fluorescence emission light sensing devices is a charged-coupled device (CCD) camera, complimentary metal-oxide semiconductor (CMOS) camera, sensor array, or a combination thereof.

13. The apparatus of claim 1, wherein each vessel comprises the aqueous reaction mix, the carrier oil, and the encapsulation oil, wherein the carrier oil is non-miscible with both the encapsulation oil and the components of the aqueous reaction mix.

14. The apparatus of claim 13, wherein the carrier oil has a density ranging from about 1,200 kg/m$^3$ to about 2,000 kg/m$^3$, the encapsulation oil has a density ranging from about 700 kg/m$^3$ to about 990 kg/m$^3$, and the aqueous reaction mix has a density ranging from about 900 kg/m$^3$ to about 1,200 kg/m$^3$.

15. The apparatus of claim 1, wherein the electromagnetic radiation sources are laser diodes emitting infrared light having a spectral wavelength in the range from about 1,300 nm to about 2,200 nm.

16. The apparatus of claim 1, wherein the electromagnetic radiation sources are laser diodes emitting infrared light having a spectral wavelength in the range from about 1,300 nm to about 1,500 nm.

17. The apparatus of claim 1, further comprising one or more hot start heating positions prior to the plurality of heating positions.

18. The apparatus of claim 1, wherein the photonic heating subsystem further comprises a lens that focuses the electromagnetic radiation of the photonic heating subsystem onto a metallic film disposed between the bottom of the vessel and the oil.

19. The apparatus of claim 1, wherein the vessels are uncovered.

20. The apparatus of claim 19, wherein the fluorescence detection subsystem is positioned in optical communication with the top of the vessel.

21. The apparatus of claim 20, wherein the photonic heating subsystem is positioned above or below the vessel.

* * * * *